United States Patent
Clark et al.

(10) Patent No.: US 11,712,388 B2
(45) Date of Patent: Aug. 1, 2023

(54) DEVICE FOR BLOOD LOSS MEASUREMENT FOLLOWING CHILDBIRTH TO DETECT POSTPARTUM HEMORRHAGE

(71) Applicant: THE REGENTS OF THE UNIVERSITY OF MICHIGAN, Ann Arbor, MI (US)

(72) Inventors: Celia Clark, Newport, MI (US); Katie Munson, Rochester Hills, MI (US); Shriya Suresh, West Bloomfield, MI (US); Yvonne Wu, Naperville, IL (US); Sanghamithra Kalimi, Troy, MI (US); Nisha Bharat, Charlotte, NC (US); Jeffrey Stephen Plott, Algonac, MI (US); Chun Hei So, Grand Blanc, MI (US); Gene Philip Parunak, Saline, MI (US); Jahnavi Nalamolu, Farmington Hills, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/910,235

(22) PCT Filed: Mar. 10, 2021

(86) PCT No.: PCT/US2021/021779
§ 371 (c)(1),
(2) Date: Sep. 8, 2022

(87) PCT Pub. No.: WO2021/183692
PCT Pub. Date: Sep. 16, 2021

(65) Prior Publication Data
US 2023/0120481 A1      Apr. 20, 2023

Related U.S. Application Data

(60) Provisional application No. 62/987,636, filed on Mar. 10, 2020.

(51) Int. Cl.
*A61G 13/10*     (2006.01)
*A61B 46/20*     (2016.01)
(Continued)

(52) U.S. Cl.
CPC ........... *A61G 13/102* (2013.01); *A61B 46/30* (2016.02); *A61J 1/12* (2013.01); *A61B 2090/063* (2016.02); *A61J 2200/76* (2013.01)

(58) Field of Classification Search
CPC ........... A61G 13/102; A61B 2046/201; A61B 2046/236; A61B 2090/063; A61B 46/30; A61J 2200/76
See application file for complete search history.

(56) References Cited

U.S. PATENT DOCUMENTS 4,076,017 A  *  2/1978  Haswell .............. A61G 13/102
                                              600/580
4,559,937 A     12/1985  Vinson
(Continued)

FOREIGN PATENT DOCUMENTS

CN    211750052 U    10/2020
EP    2364667 A1     9/2011
RU    2373961 C2  *  11/2009 ................ A61J 1/10

OTHER PUBLICATIONS

Wang F, Lu N, Weng X, Tian Y, Sun S, Li B. Measurement of postpartum blood loss using a new two-set liquid collection bag for vaginal delivery: a prospective, randomized, case control study. Medicine. 2021;100:19(e25906). (Year: 2021).*

(Continued)

*Primary Examiner* — Ariana Zimbouski
(74) *Attorney, Agent, or Firm* — Harness, Dickey & Pierce, P.L.C.

(57) ABSTRACT

A device for detecting postpartum hemorrhage is provided. A mat defines a proximal end and a distal end. The mat is (Continued)

configured to be disposed between a support and a patient and has a surface with a fluid flow region configured to direct flow of bodily fluids from the patient towards the distal end of the mat. A first detachable and optionally sealable bag is configured to receive the bodily fluids from the patient in a first operational mode of the device. A second sealable bag is configured to receive the bodily fluids from the patient in a second operational mode of the device. The second sealable bag comprises a visual volume indicator to measure the bodily fluids collected in the second sealable bag.

28 Claims, 58 Drawing Sheets

(51) Int. Cl.
    *A61J 1/12*         (2006.01)
    *A61B 46/00*      (2016.01)
    *A61B 90/00*      (2016.01)

(56) References Cited

U.S. PATENT DOCUMENTS

| | | | |
|---|---|---|---|
| 5,618,278 A | | 4/1997 | Rothrum |
| 5,916,202 A | * | 6/1999 | Haswell ............ A61B 5/150305 |
| | | | 128/853 |
| 5,961,503 A | * | 10/1999 | Simmet ................ A61D 19/021 |
| | | | 604/347 |
| 11,471,234 B2 | * | 10/2022 | Carranza ................ A61B 90/06 |
| 2016/0166323 A1 | * | 6/2016 | Tylka ..................... A61B 46/00 |
| | | | 128/852 |

OTHER PUBLICATIONS

International Search Report and Written Opinion regarding International Application No. PCT/US2021/021779, dated Jul. 15, 2021; ISA/US.

* cited by examiner

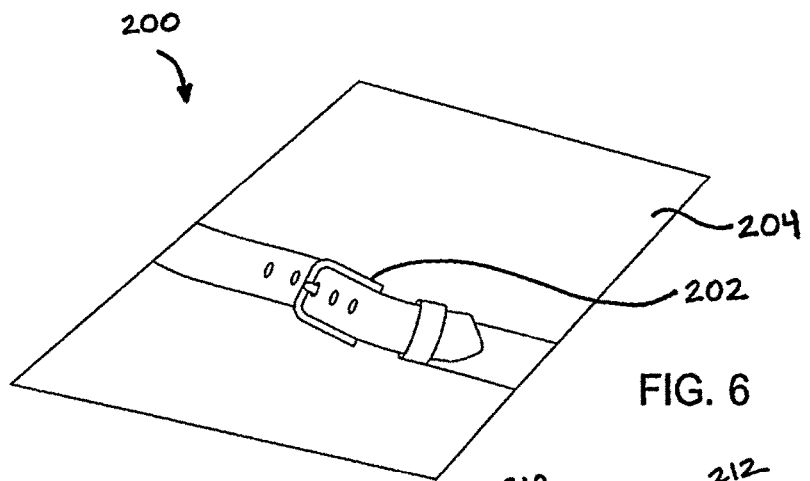
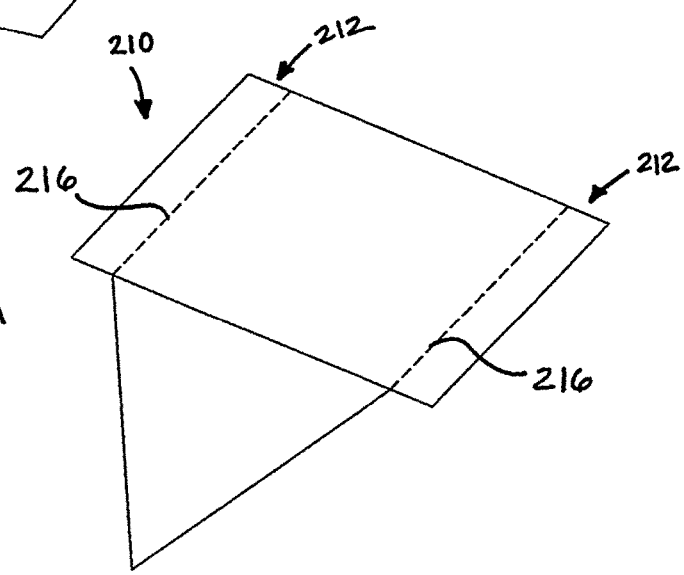
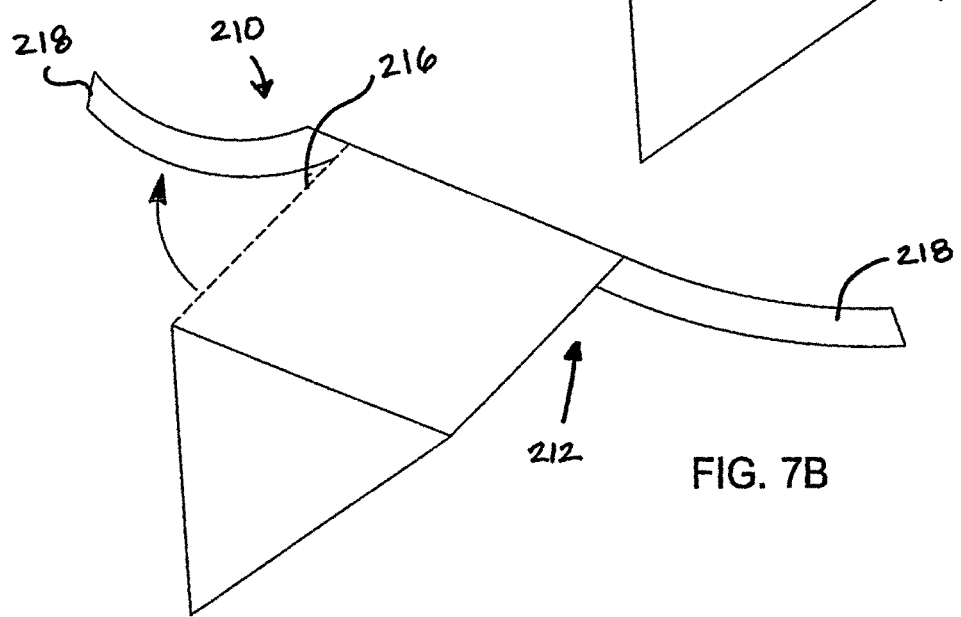
FIG. 6
FIG. 7A
FIG. 7B

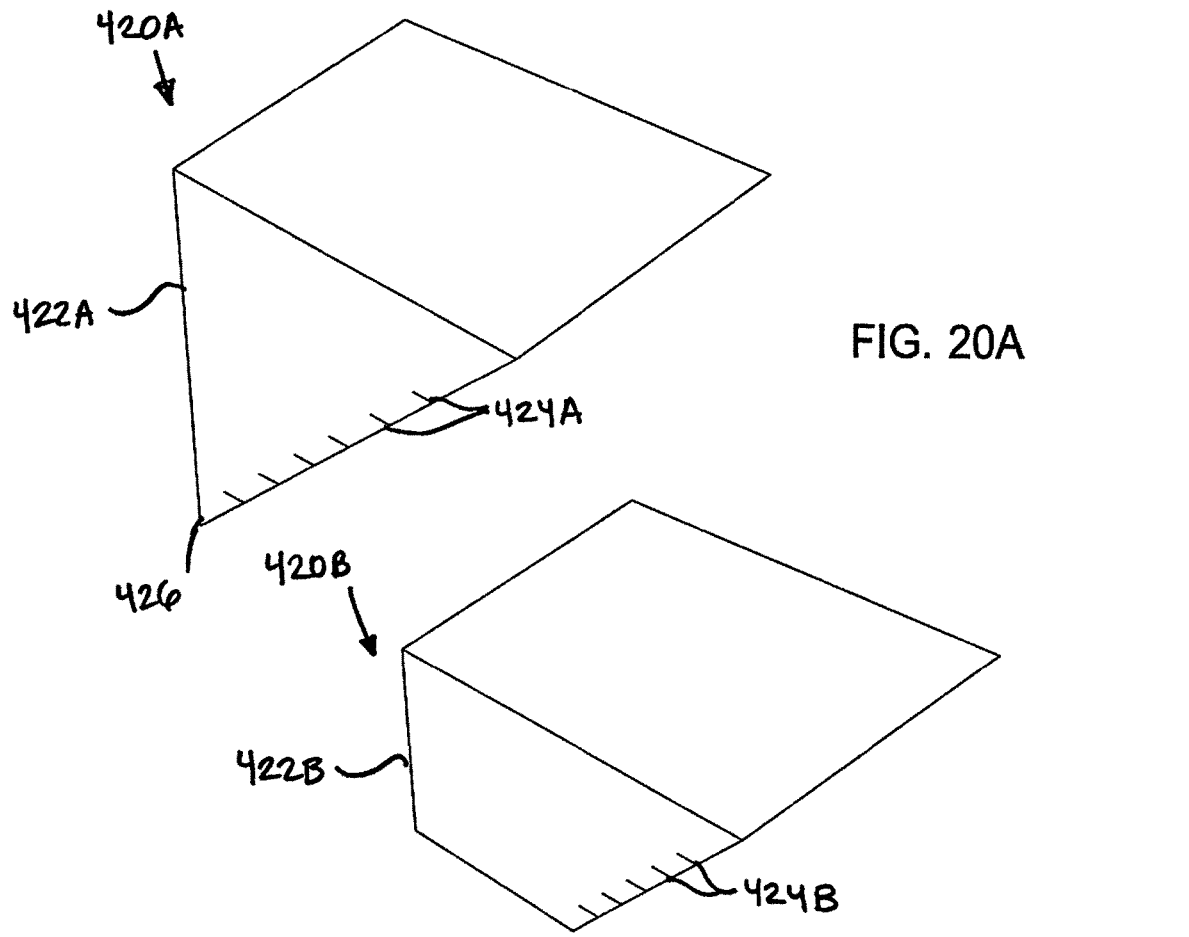
FIG. 20A
FIG. 20B
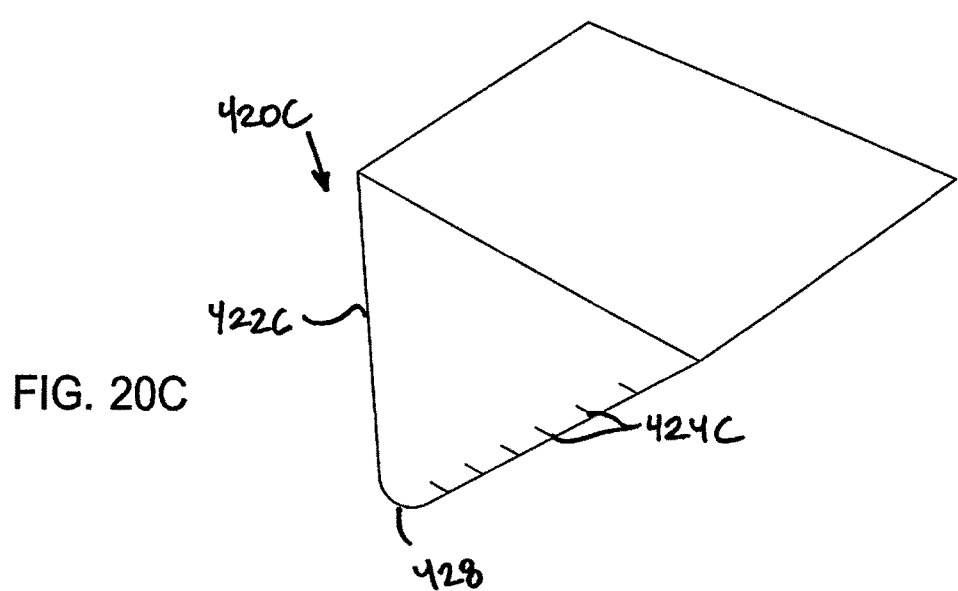
FIG. 20C

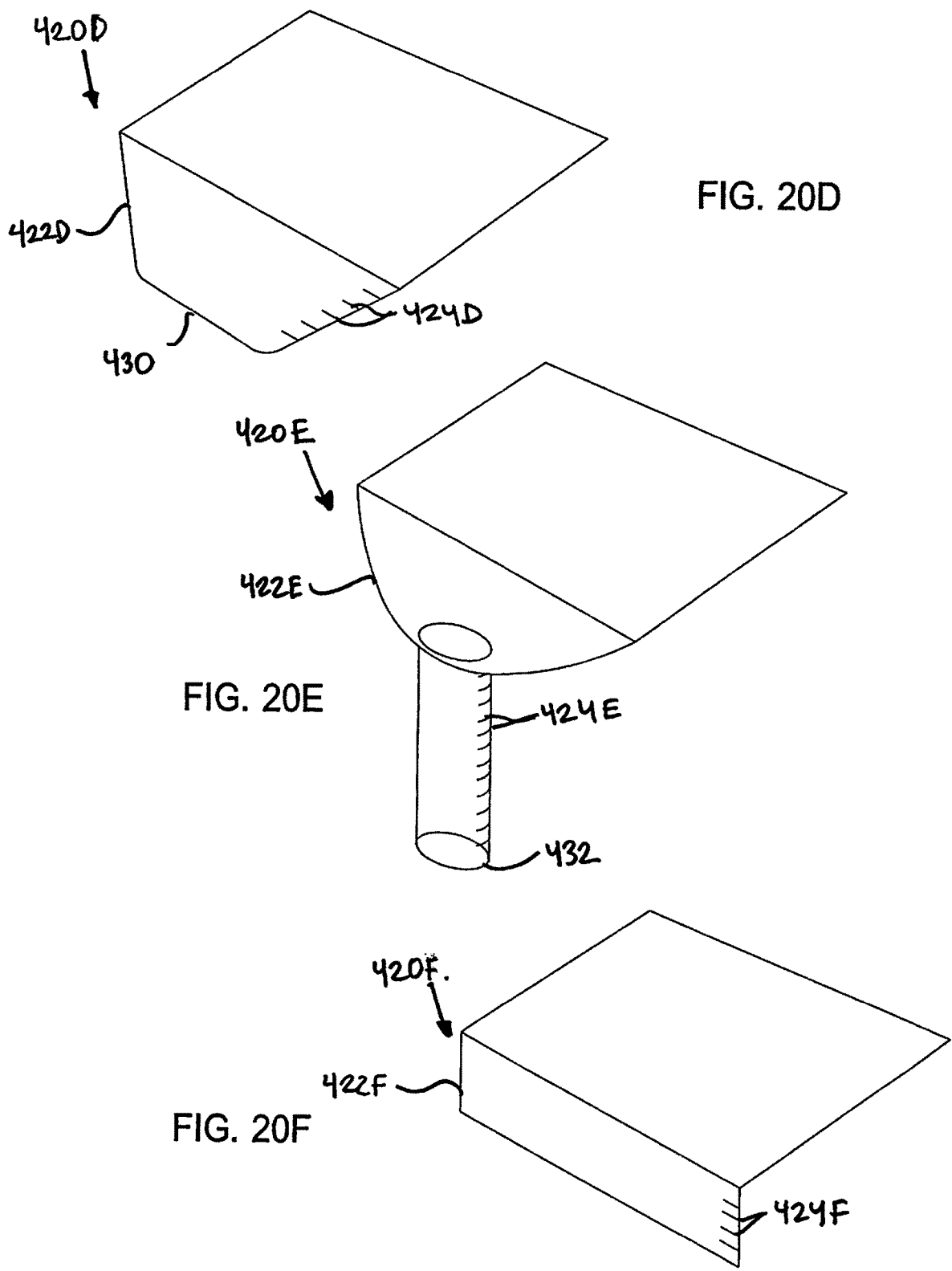

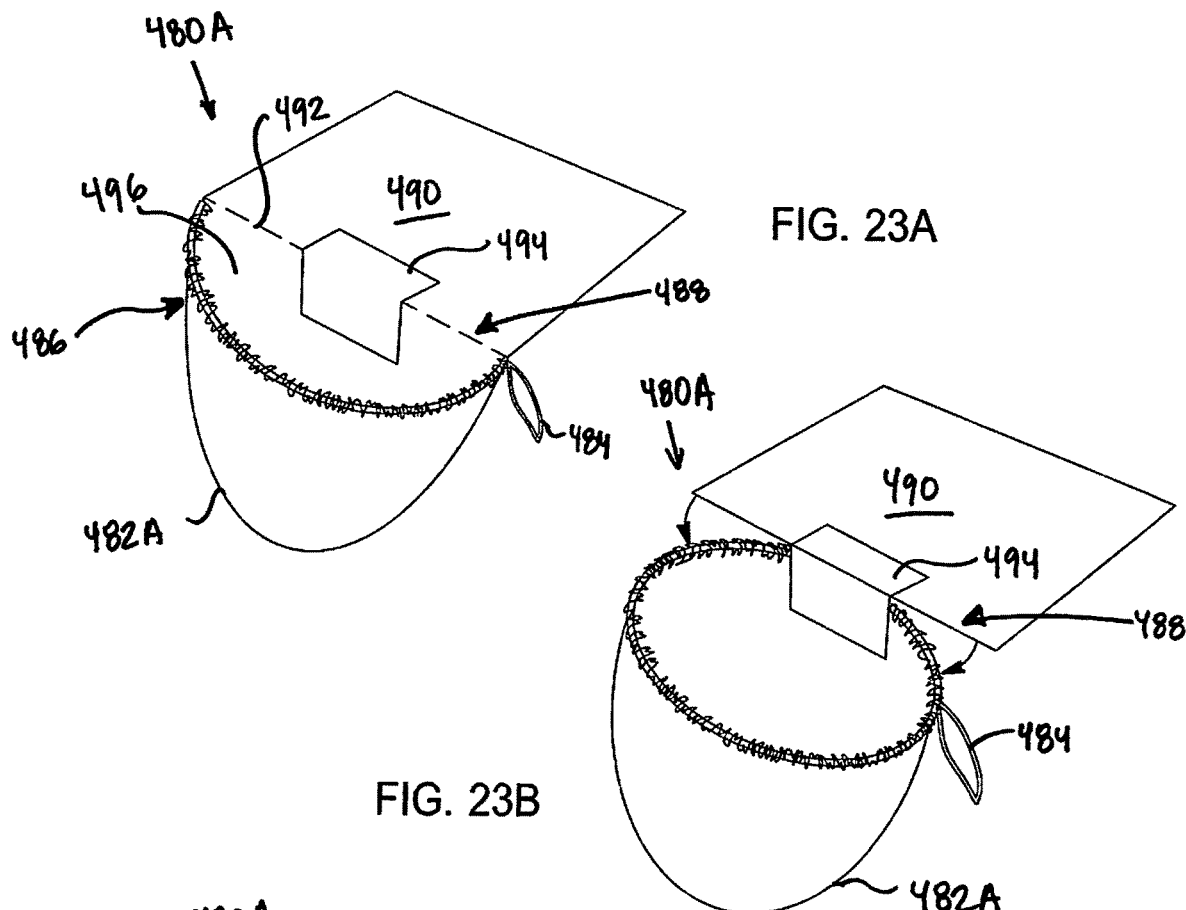
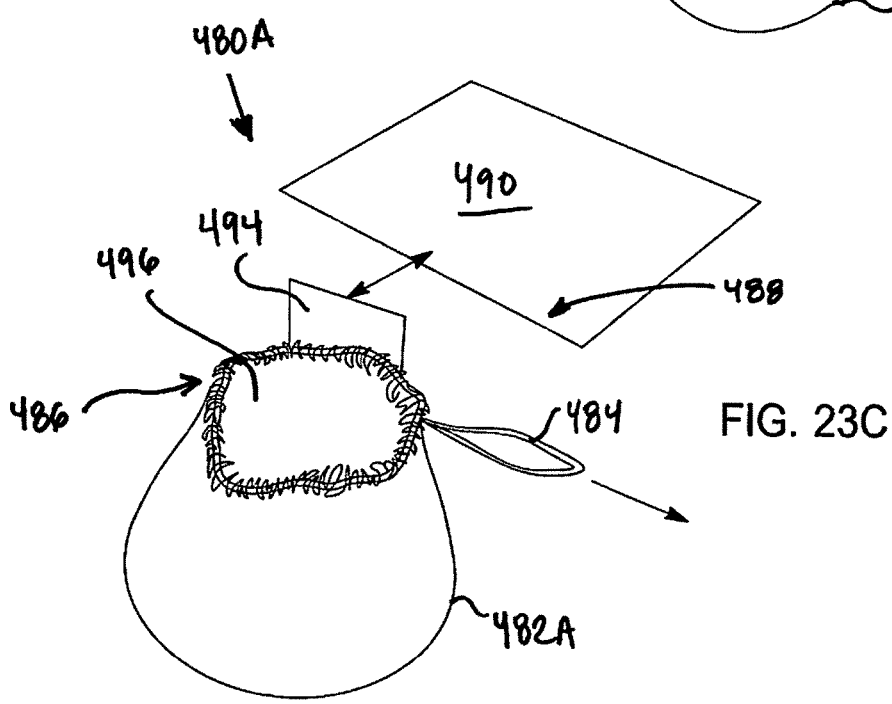
FIG. 23A
FIG. 23B
FIG. 23C

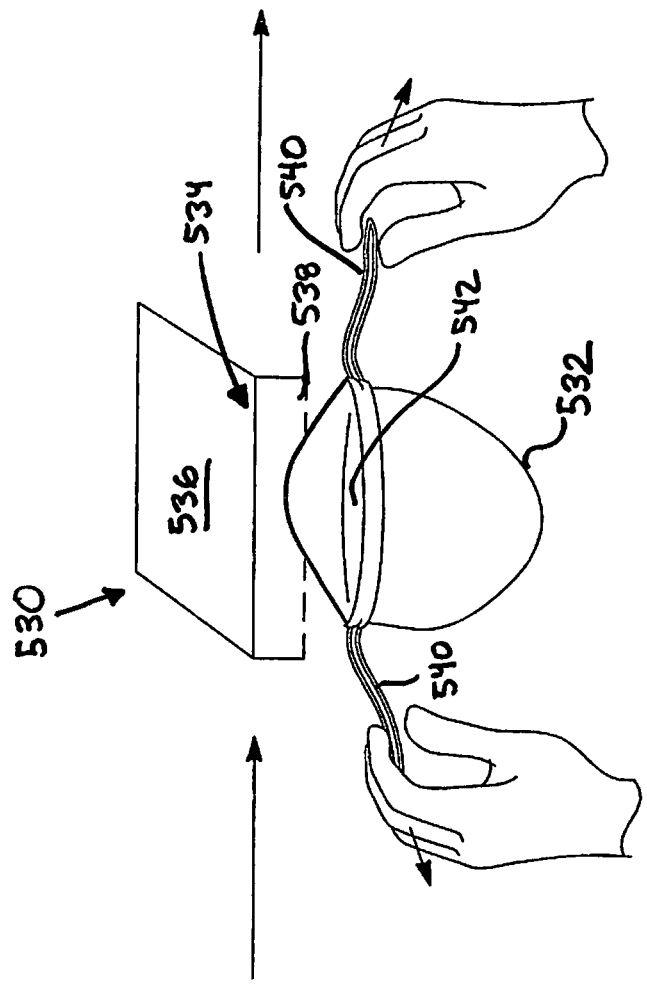
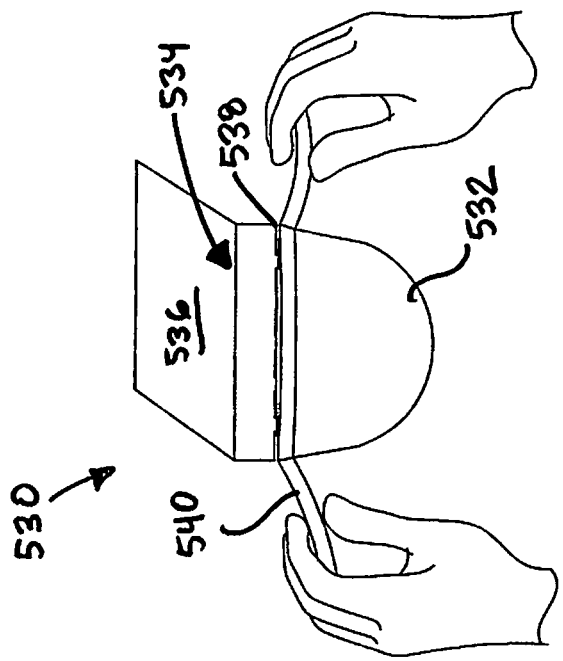
FIG. 25B
FIG. 25A

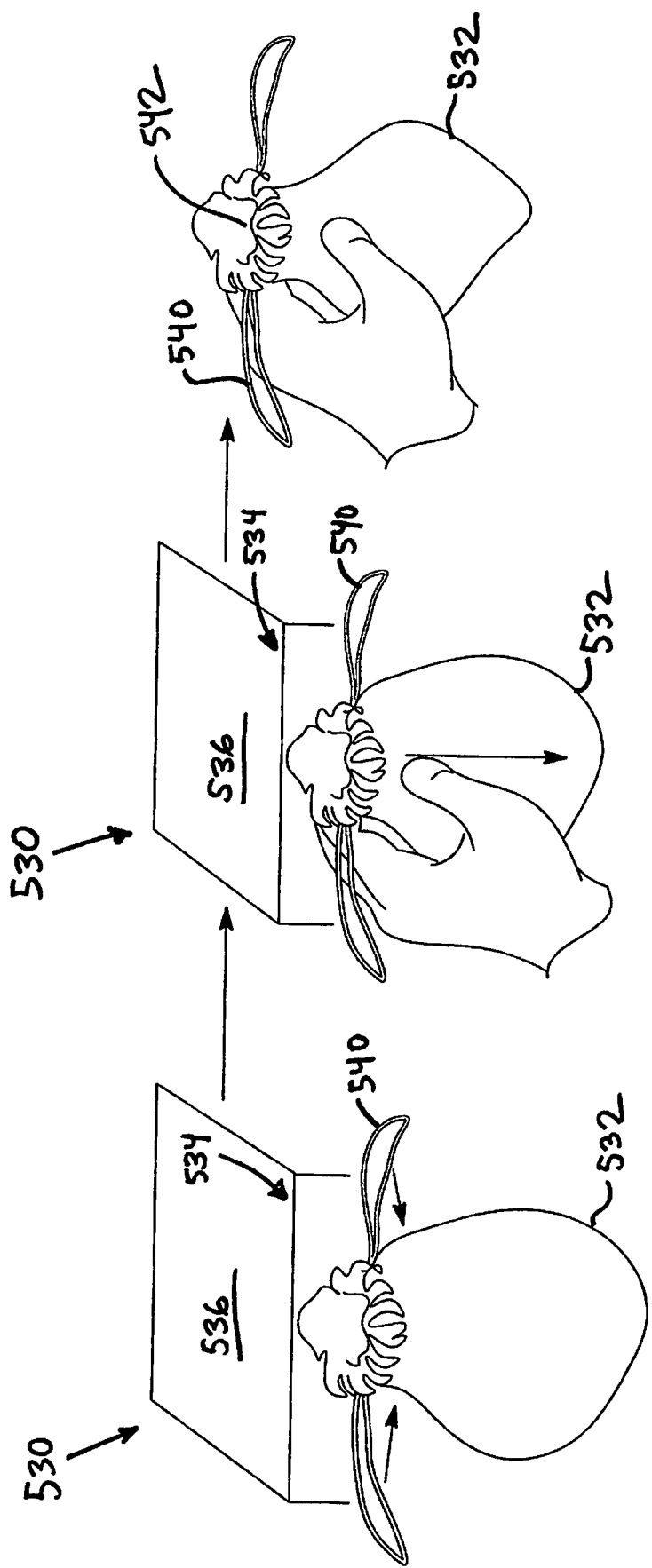

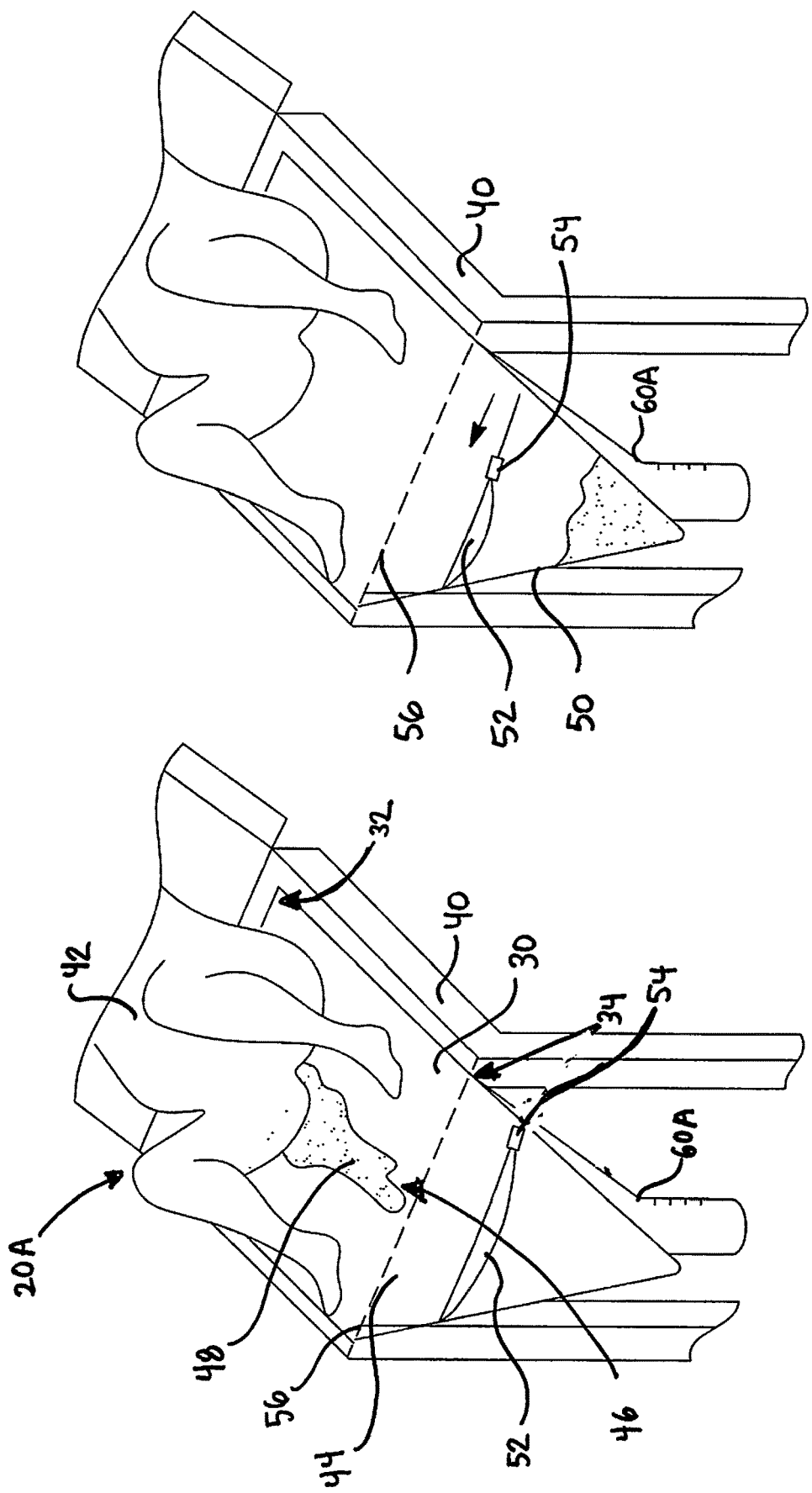

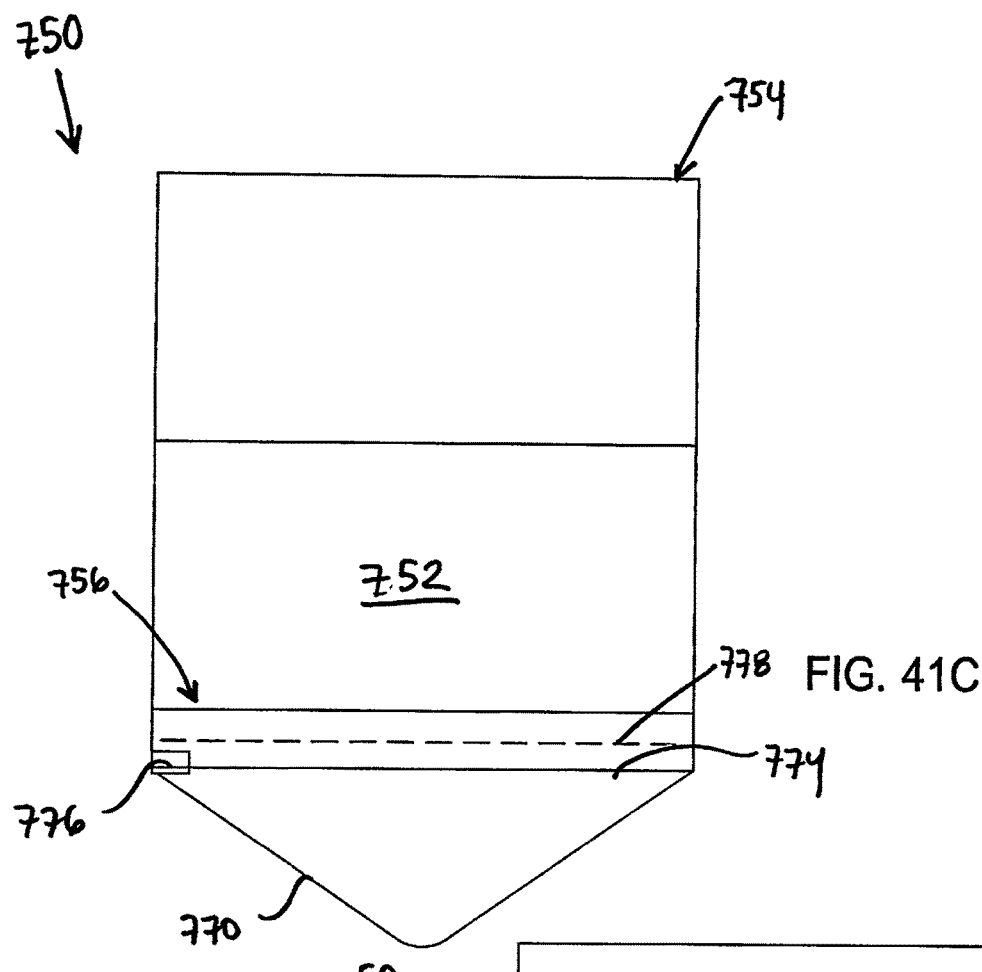
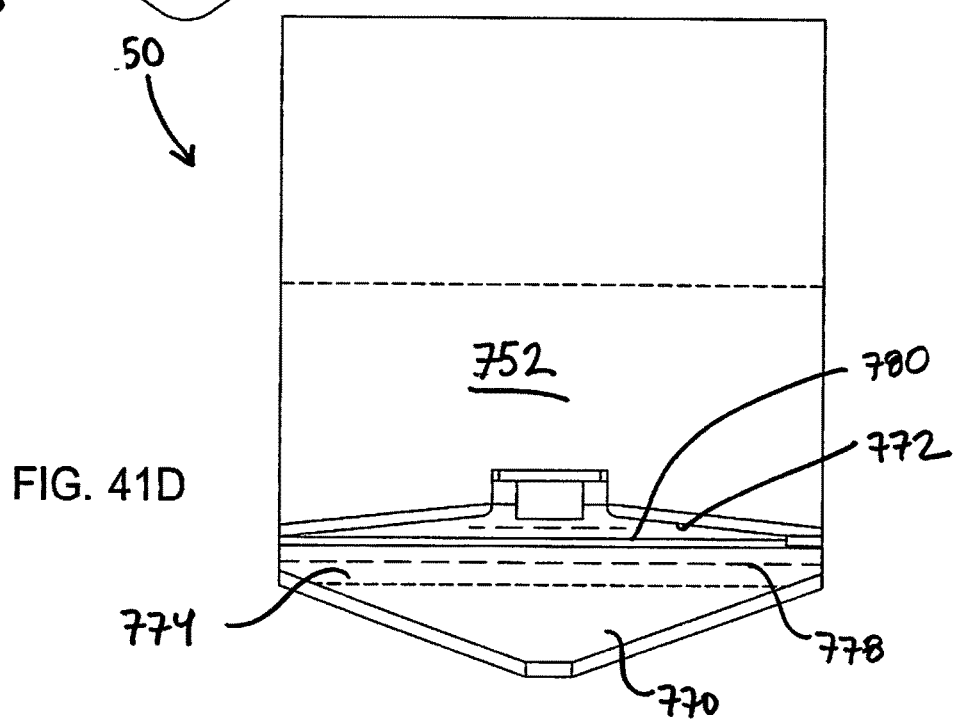

DEVICE FOR BLOOD LOSS MEASUREMENT FOLLOWING CHILDBIRTH TO DETECT POSTPARTUM HEMORRHAGE

CROSS-REFERENCE TO RELATED APPLICATIONS

This application is a U.S. National Phase Application under 35 U.S.C. 371 of PCT International Application PCT/US2021/021779 filed on Mar. 10, 2021, which claims the benefit of U.S. Provisional Application No. 62/987,636, filed on Mar. 10, 2020. The disclosures of the above applications are incorporated herein by reference in its entirety.

FIELD

The present disclosure relates to a device for measuring blood loss from a patient following childbirth to detect postpartum hemorrhage.

BACKGROUND

This section provides background information related to the present disclosure which is not necessarily prior art.

Postpartum hemorrhage (PPH) is the leading cause of maternal mortality worldwide, accounting for up to 30% of maternal deaths every year, and particularly afflicts low resource settings. Primary PPH is defined as blood loss following a vaginal delivery that exceeds 500 mL, or any amount of blood loss that could pose a potential health risk to the patient within 24 hours of delivery of the child. The accurate measurement of blood loss is an important tool in order to diagnose PPH and initiate appropriate treatment, such as blood transfusions. Clinical symptoms can delay in presentation, therefore being able to quantify an amount of blood loss quickly can facilitate early diagnosis and permit appropriate and timely administration of blood transfusions or other treatments. Furthermore, underestimations of blood loss may result in over-transfusions of blood product, leading to the waste of a resource that can be scarce in low resource areas.

Current methods used to assess postpartum blood loss in low resource areas rely heavily on visual estimation. Providers are able to estimate the amount of blood lost by visually examining the blood that has spilled onto the floor, around the bed, and by counting the number of saturated pads, gauze, and bed mats used throughout labor. The accuracy of these assessments varies between healthcare personnel based on experience level and thus can be very subjective. Studies have shown that current visual estimation methods result in underestimation of blood loss by up to 50%. This can result in delay of treatment of PPH if attending healthcare personnel wait for other clinical symptoms to appear, which can result in an increased risk of complications from PPH. Healthcare personnel understand this and therefore have very little faith in their own estimation.

It would be desirable to have a device that can accurately quantify blood loss after childbirth to diagnose primary postpartum hemorrhage, especially within a window of 4 hours after vaginal delivery, as this is when most deaths occur. Such a device could desirably provide the following advantageous features: minimal or no interference with the delivery process and not impeding access of a clinician to the patient, an ability to distinguish blood from other fluids, comfort to the patient, durable, safe and sterile, accurate, easy to maintain, and inexpensive.

SUMMARY

This section provides a general summary of the disclosure, and is not a comprehensive disclosure of its full scope or all of its features.

In certain aspects, the present disclosure relates to a device for detecting postpartum hemorrhage in a patient. The device comprises a mat, which may be a polymeric mat. The mat defines a proximal end and a distal end and is configured to be disposed between a support and a patient. The mat comprises a surface defining a fluid flow region configured to direct flow of bodily fluids from the patient towards the distal end of the polymeric mat. A first detachable and optionally sealable bag has a first opening in fluid communication with the distal end of the fluid flow region and is configured to receive the bodily fluids from the patient in a first operational mode of the device. A second sealable bag has a second opening in fluid communication with the distal end of the fluid flow region and is configured to receive the bodily fluids from the patient in a second operational mode of the device. The second sealable bag comprises a visual volume indicator to measure the bodily fluids collected in the second sealable bag.

In one aspect, the first detachable bag is disposed over the second sealable bag.

In one aspect, the first detachable bag is removable from the mat such that, in a detached state, it is not directly or indirectly coupled to the distal end of the mat or the second sealable bag. In one aspect, the first detachable bag and the second sealable bag are separable from each other.

In one aspect, the first detachable bag has a first volumetric capacity and the second sealable bag has a second volumetric capacity. The first volumetric capacity and the second volume capacity are equal to one another and each is less than or equal to about 2,000 mL.

In one aspect, the visual volume indicator comprises a minimum volumetric unit of 250 mL.

In one aspect, the first detachable bag has a first shape and the second sealable bag has a second shape. The first shape and the second shape are the same and selected from one of an isosceles triangle and an isosceles trapezoid. Alternatively, the first shape and the second shape may comprise different shapes.

In one aspect, the mat defines two peripheral edges that define a region selected from one of a bumper, a raised portion, a roll, or a channel to create the fluid flow region and configured to prevent egress of bodily fluids beyond the two peripheral edges.

In one aspect, the device further comprises a fastener to couple the mat to the support.

In one further aspect, the fastener is selected from one or more of: a belt or a strap that extends around a circumference of the support; an adhesive that adheres to a surface of the support; buttons to couple to a surface of the support; magnets to couple to a surface of the support; hook and eye material to couple to a surface of the support; or a snap to couple to a surface of the support.

In one aspect, the distal end of the mat extends over a terminal edge of the support.

In one aspect, the device further comprises fasteners to couple the mat to the patient, wherein the fasteners comprise at least two straps.

In one aspect, the mat defines two peripheral edges that each extend over lateral edges of the support.

In one aspect, the first detachable bag and the second sealable bag comprise a closure mechanism selected from one or more of a zipper, a slide, an adhesive, or a cinching string.

In one aspect, the closure mechanism is disposed in a protective sleeve.

In one aspect, the first detachable bag, the second sealable bag, and the mat are independently formed of a polymer selected from the group consisting of: polypropylene, polyethylene, polyetheretherketone (PEEK), polyvinylchloride (PVC), polyurethane (PU), metallocene catalyzed thermoplastic polymers, siloxane, elastomers, shape memory elastomers, and combinations thereof.

In one aspect, the first detachable bag and the second sealable bag are disposable.

In one aspect, the mat is reusable and the first detachable bag and the second sealable bag each comprises at least one connector to reversibly couple with the mat.

In one aspect, the second sealable bag further comprises a filter configured to filter blood from other substances generated by the body, such as blood clots or other bodily fluids.

In one aspect, the mat has a shape selected from a rectangle, a trapezoid, or a hemisphere.

In one aspect, the first detachable bag and the second sealable bag comprise a handle.

In one aspect, the first detachable bag and/or the second sealable bag further each comprises an internally disposed reinforcement to retain a shape and maintain patency of the first opening and/or the second opening.

In one aspect, the distal end of the mat defines a shape selected from a trapezoid, a triangle, and a rectangle.

In one aspect, at least one of the first detachable bag and the second sealable bag comprises a port.

In one aspect, the proximal end of the mat comprises a flap or folded region.

In one aspect, the first detachable and sealable bag has a first shape and the second sealable bag has a second shape. The first shape is optionally selected from one of an isosceles triangle and an isosceles trapezoid and the second shape comprises a portion in the form of a graduated cylinder.

In one further aspect, the second shape further includes an entry region defining a triangular, quadrilateral, or pentagon shape connected to the graduated cylinder.

In one aspect, the second sealable bag has a back wall that is dark and a front wall that is transparent and the visual volume indicator is on the front wall.

In one aspect, the visual volume indicator includes a portion indicated in a dark color and a portion indicated in a light color.

In certain aspects, the present disclosure contemplates a new, original and ornamental design for a device for blood loss measurement following childbirth to detect postpartum hemorrhage, as shown in FIGS. 41A-41G.

In certain aspects, the present disclosure contemplates a new, original and ornamental design for a device for blood loss measurement following childbirth to detect postpartum hemorrhage, as shown in FIGS. 42A-42B.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1B show a device for collecting bodily fluids from a patient during and after childbirth prepared in accordance with certain aspects of the present disclosure. More specifically, FIG. 1A shows a perspective view of the device on a support (e.g., an articulated hospital bed) for a patient, where collection bags have a triangular or conical shape. FIG. 1B is an image of a prototype of the device for collecting bodily fluids from a patient during and after childbirth prepared in accordance with certain aspects of the present disclosure.

FIGS. 2A-2D show a device for collecting bodily fluids from a patient during and after childbirth prepared in accordance with certain aspects of the present disclosure. FIG. 2A shows a first operational mode of the device where the device is disposed between a patient and a support (e.g., hospital bed) and collects bodily fluids from the patient. FIG. 2B shows a first detachable and sealable bag being sealed. FIG. 2C shows a transition between the first operational mode and a second operational mode of the device. FIG. 2D shows the device collecting bodily fluids from the patient during the second operational mode.

FIGS. 3A-3D are illustrations of a representative device with dimensions for collecting bodily fluids from a patient during and after childbirth prepared in accordance with certain aspects of the present disclosure, where collection bags have a triangular shape. FIG. 3A is a top view, FIG. 3B is an isometric view, FIG. 3C is a side view of the collection bags, and FIG. 3D is a side view of the device.

FIGS. 4A-4C are illustrations of a device for collecting bodily fluids from a patient during and after childbirth prepared in accordance with certain aspects of the present disclosure, where a mat has raised edges and collection bags have a trapezoidal shape. FIG. 4A is a top view of a mat region. FIG. 4B is a side view of a collection bag. FIG. 4C is a side view of the device with two collection bags.

FIG. 6 is an illustration of a device for collecting bodily fluids from a patient during and after childbirth prepared in accordance with certain aspects of the present disclosure that includes a belt configured to be extended around a circumference of a support that may mechanically secure the device to the support structure.

FIGS. 7A-7E illustrate variations of a device for collecting bodily fluids from a patient during and after childbirth prepared in accordance with certain aspects of the present disclosure that includes perforated edge regions of a mat that can be torn to form strips that can be tied and secured around the support structure or a patient.

In FIG. 14A, the bag is open, while in FIG. 14B, the bag is closed between the second and third stage of labor.

Figure 15A:
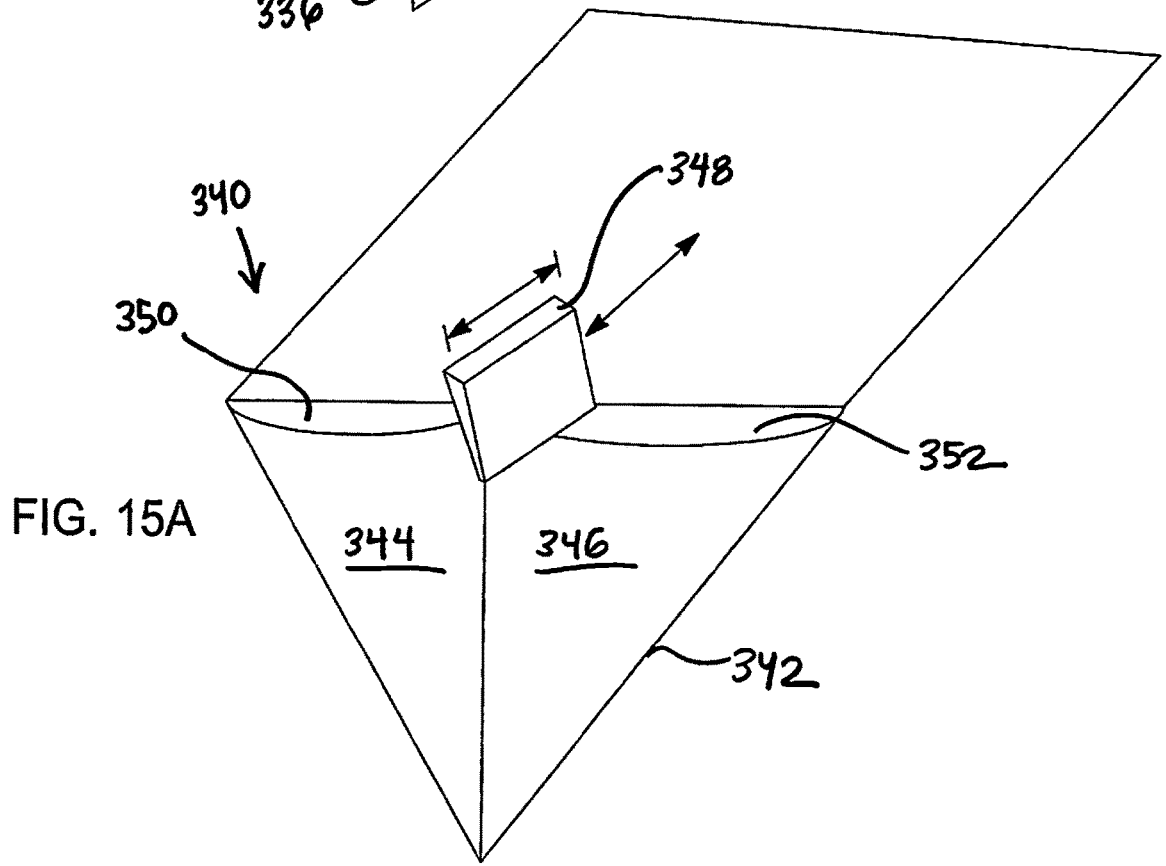
Figure 15B:
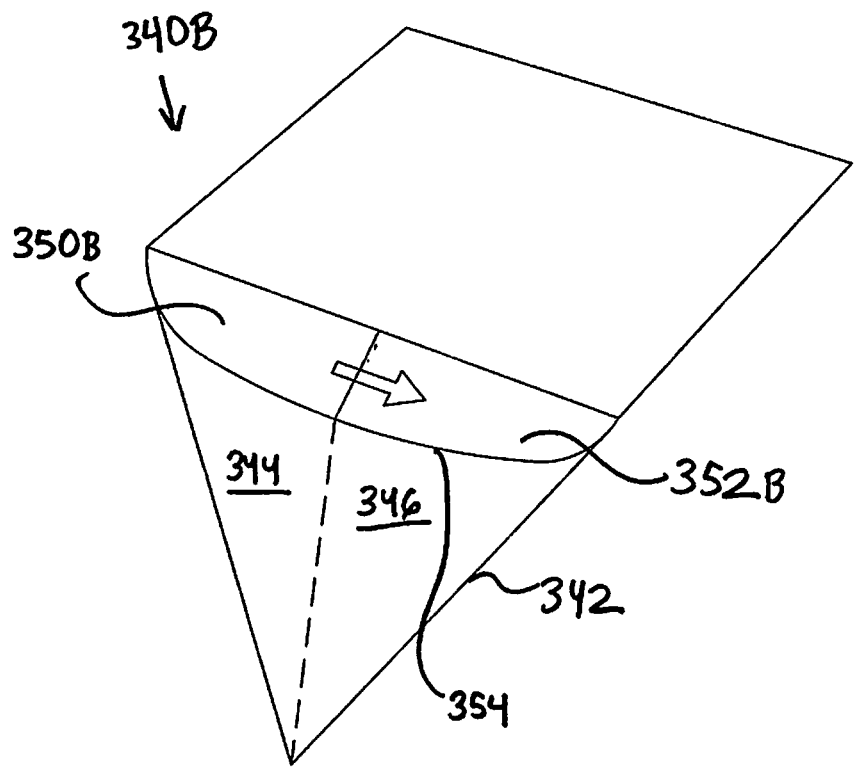

FIGS. 15A-15B are illustrations of a variation of devices for collecting bodily fluids from a patient during and after childbirth prepared in accordance with certain aspects of the present disclosure where a collection bag has two distinct compartments. FIG. 15A is adjustable between openings of the two compartments via a slider mechanism, while FIG. 15B is adjustable between openings of the two compartments via a sliding/folding lid.

Figure 16A:
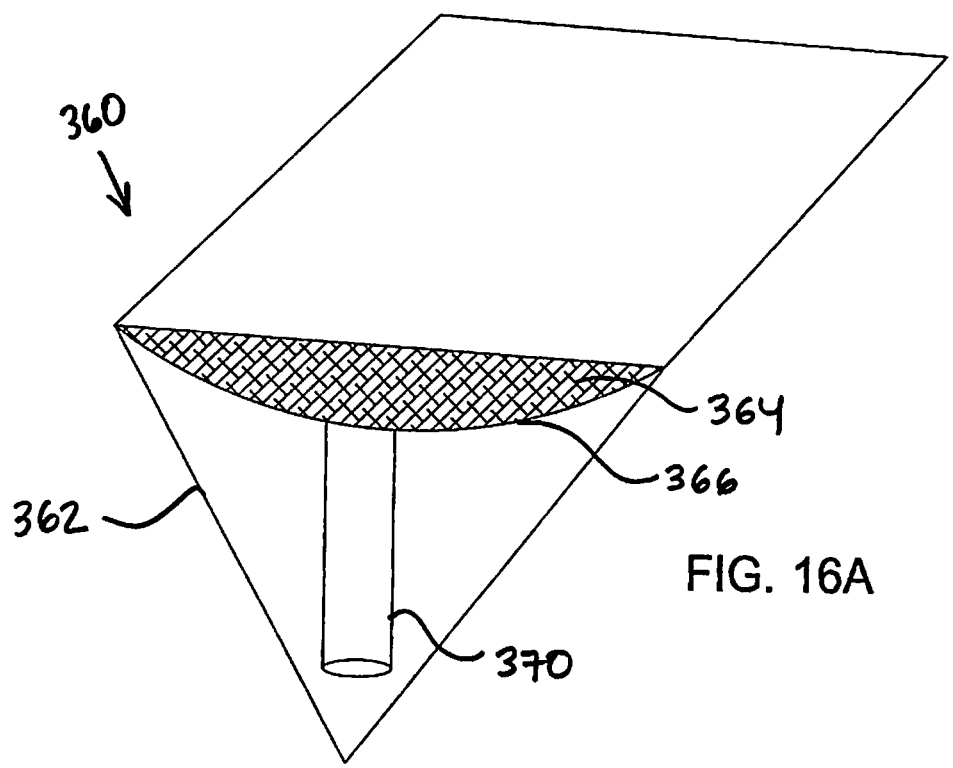
Figure 16B:
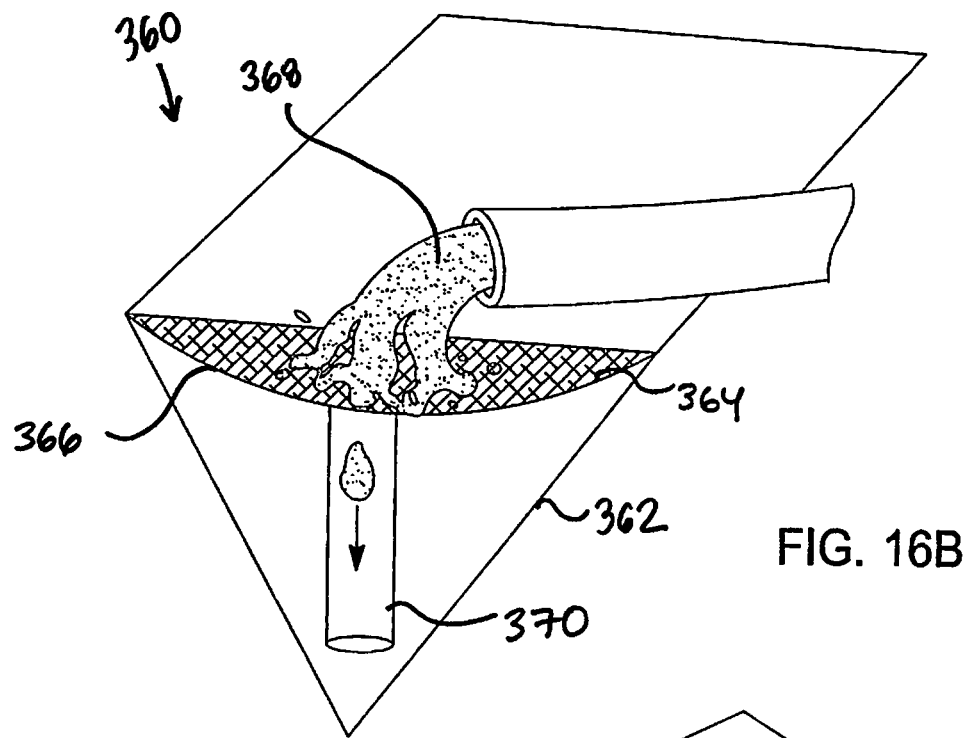

FIGS. 16A-16B are illustrations of another variation of a device for collecting bodily fluids from a patient during and after childbirth prepared in accordance with certain aspects of the present disclosure where a collection bag has a filter device at the opening. In FIG. 16B, when blood is collected, extra blood clots can fall through tube filter to be collected.

Figure 17:
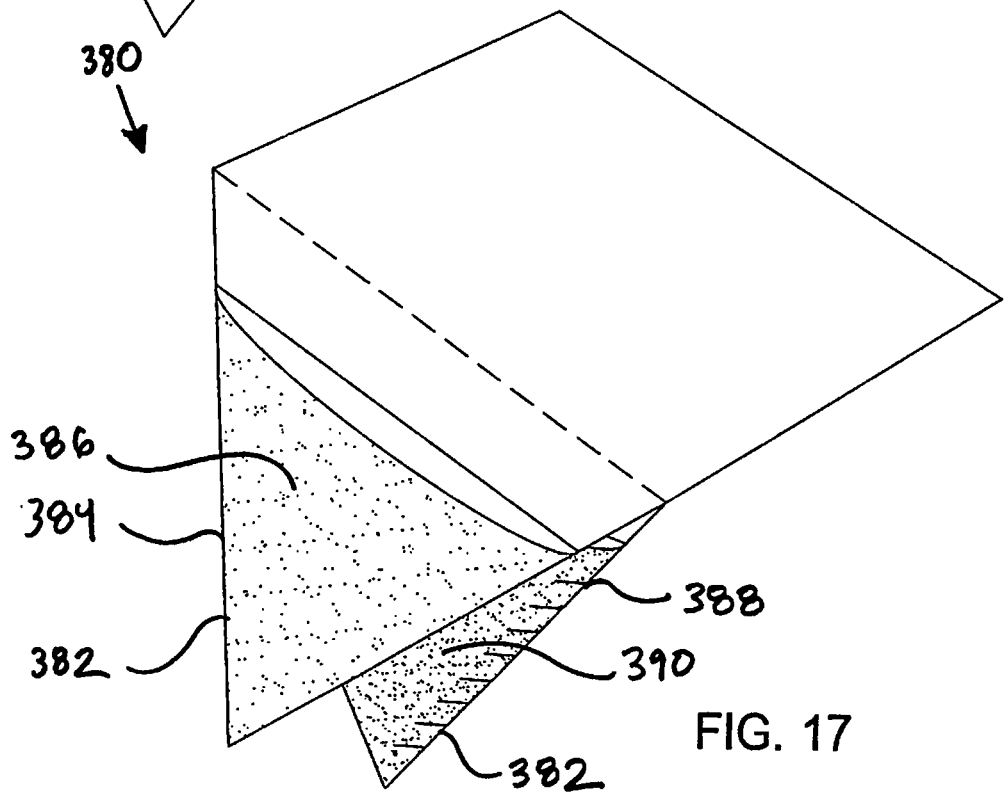

FIG. 17 is an illustration of yet another variation of a device for collecting bodily fluids from a patient during and after childbirth prepared in accordance with certain aspects of the present disclosure, where the device includes two detachable and sealable collection bags.

Figure 18A:
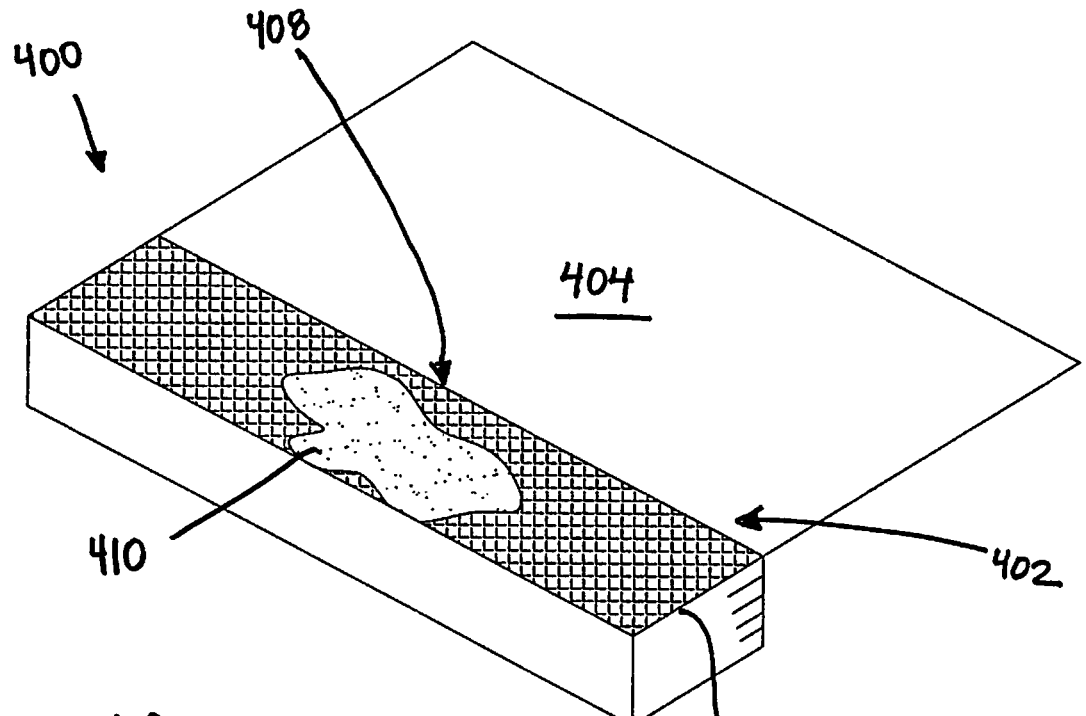
Figure 18B:
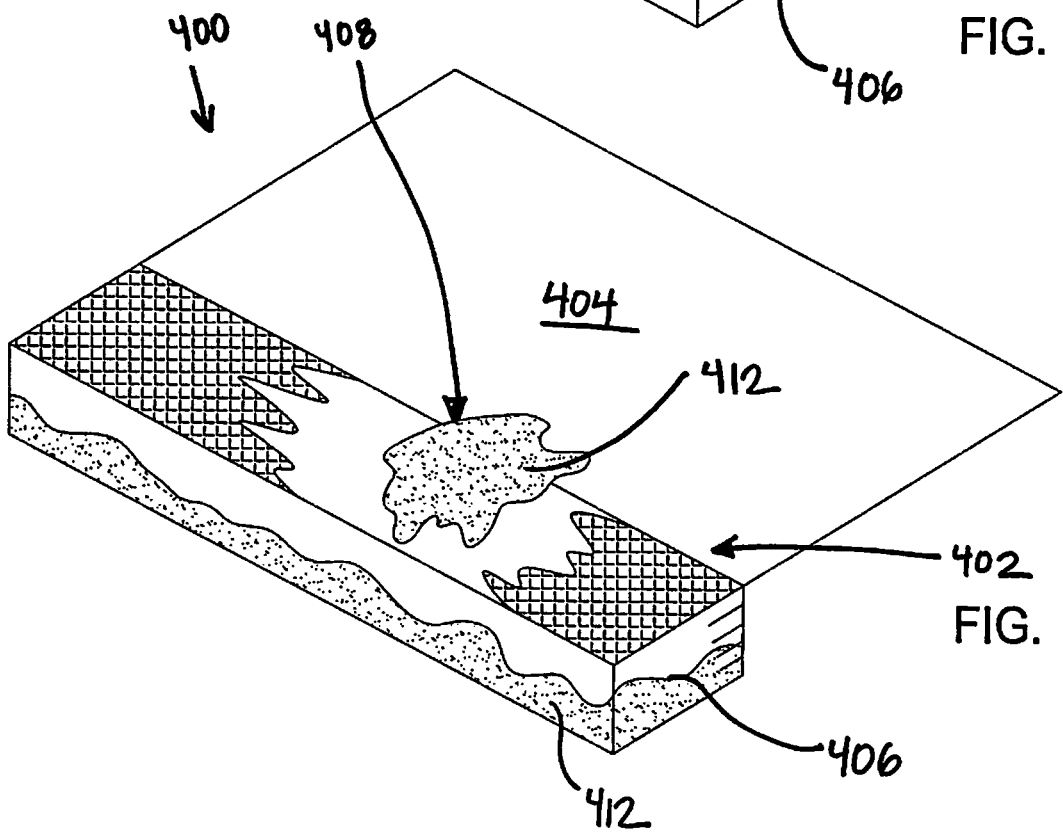

FIGS. 18A-18B are an illustration of one variation of a device for collecting bodily fluids from a patient during and after childbirth prepared in accordance with certain aspects of the present disclosure where a distal end of a mat has a specialized material disposed within the flow field that processes the bodily fluids. FIG. 18A shows non-blood fluid, like amniotic fluid, on the specialized material, while FIG. 18B shows blood soaking through into a measuring container below.

Figure 19A:
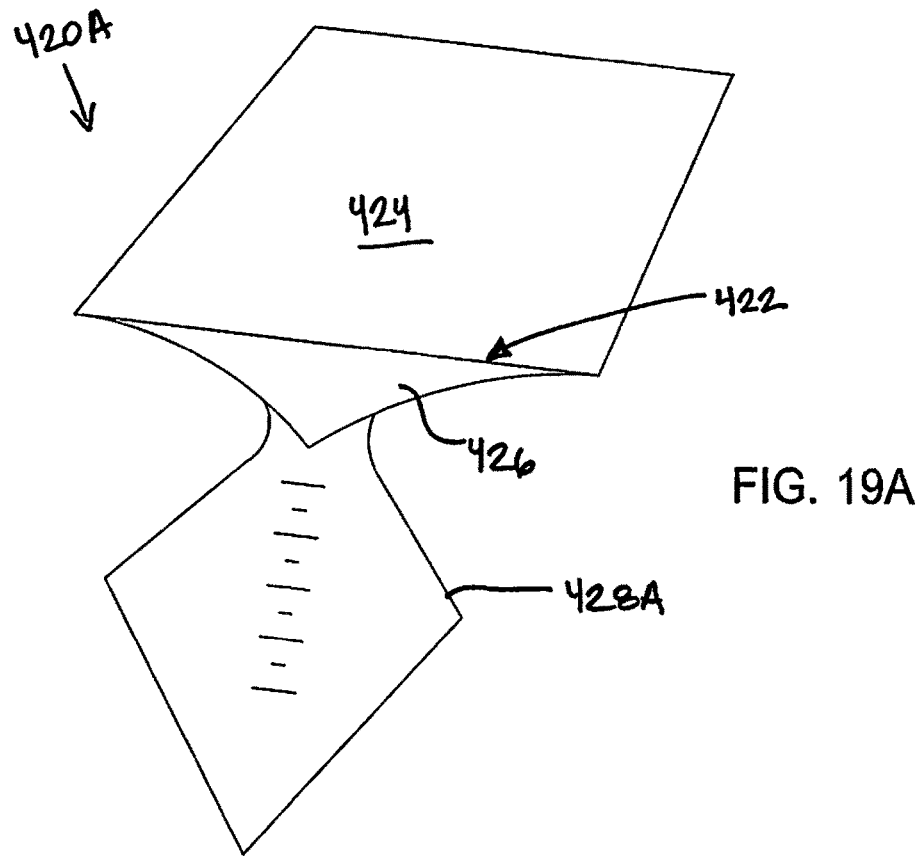
Figure 19B:
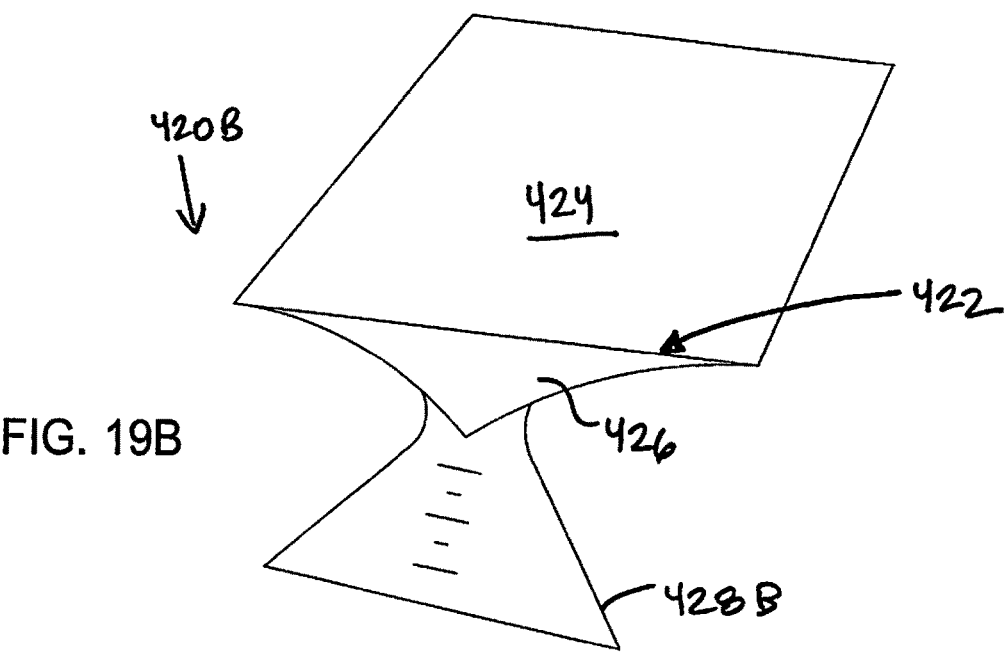

FIGS. 19A-19B are illustrations of variations of a device for collecting bodily fluids from a patient during and after childbirth prepared in accordance with certain aspects of the present disclosure where a distal end of a mat has a tongue region defining a triangular shape attached to a collection bag having a diamond shape (FIG. 19A) or a triangular shape (FIG. 19B).

Figure 20G:
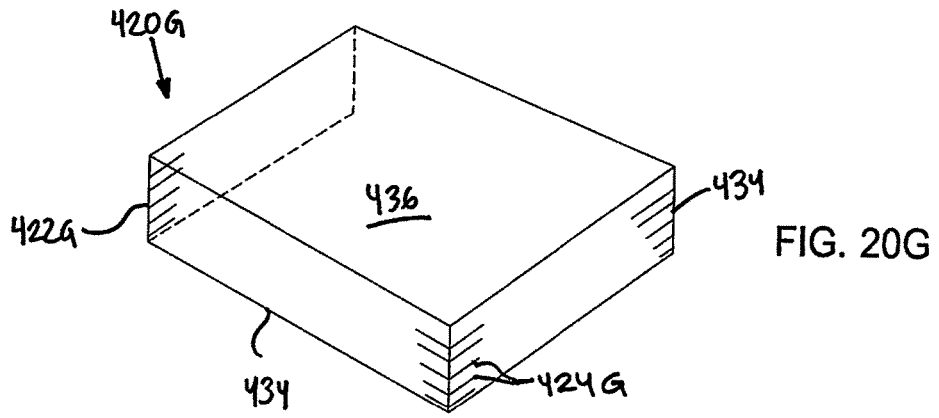

FIGS. 20A-20I are illustrations of various representative examples of devices for collecting bodily fluids from a patient during and after childbirth prepared in accordance with certain aspects of the present disclosure, where a second collecting bag or vessel for a second operational mode may have a variety of different shapes or designs. FIGS. 20A and 20B show triangular shaped second collection bags. FIGS. 20B and 20D show trapezoidal shaped second collection bags. FIG. 20E shows the second collection vessel is in the form of a graduated cylinder.

FIGS. 20F-20I show various embodiments of rectangular second collection bags.

Figures 21A, 21B, 21C:
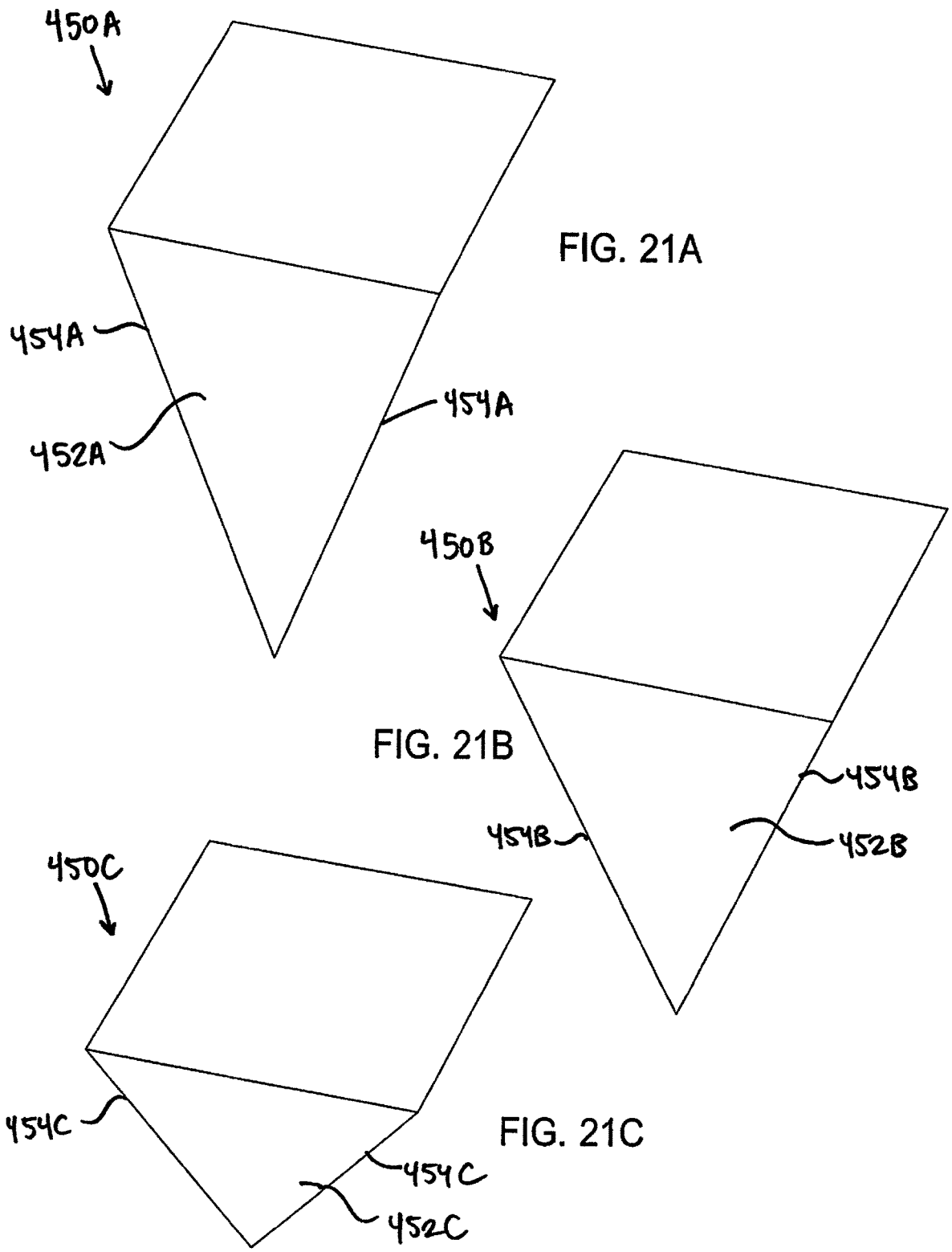

FIGS. 21A-21C show various representative examples of devices for collecting bodily fluids from a patient during and after childbirth prepared in accordance with certain aspects of the present disclosure, where a collecting bag for either first or second operational modes are triangular, but have different sizes (FIG. 21A shows a large-sized triangle, FIG. 21B shows a medium-sized triangle, and FIG. 21C shows a small-sized triangle collection bag).

Figure 22:
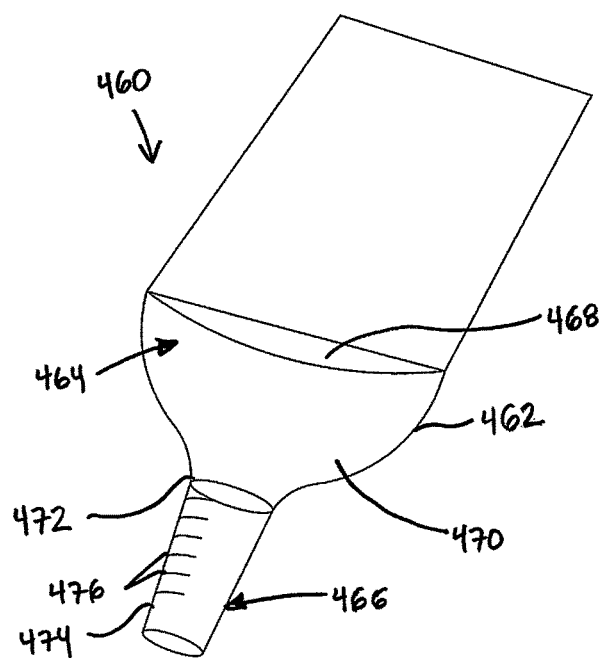

FIG. 22 illustrates another example of a device for collecting bodily fluids from a patient during and after childbirth prepared in accordance with certain aspects of the present disclosure, where a collecting bag has a wine glass shape with a cylindrical collection vessel.

Figure 23D:
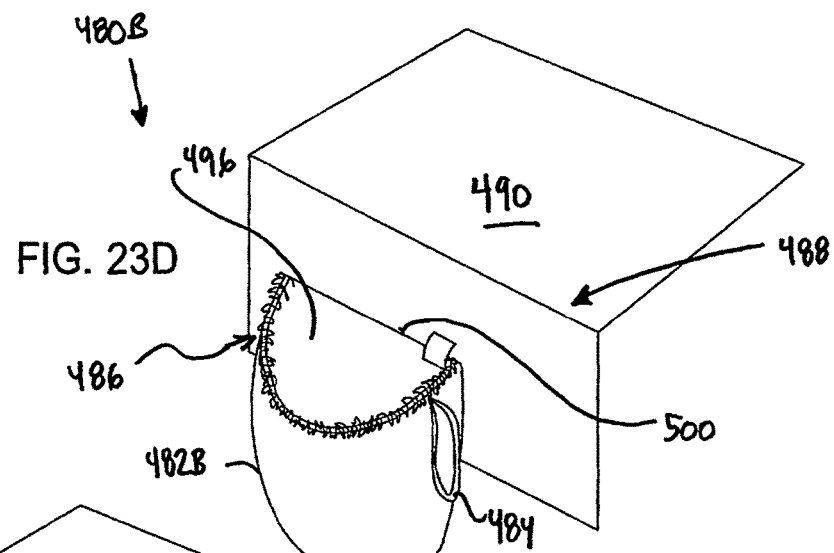

FIGS. 23A-23F illustrate variations of devices for collecting bodily fluids from a patient during and after childbirth prepared in accordance with certain aspects of the present disclosure, where the collection bags have a closure mechanism that involves cinching. FIGS. 23A-23C show steps of using a perforated edge and adhesive tape to cinch and remove the collecting bag after use. FIGS. 23D-23D show use of a zipper to hold the bag that is unzipped to remove the collecting bag after use.

Figures 24A, 24B, 24C:
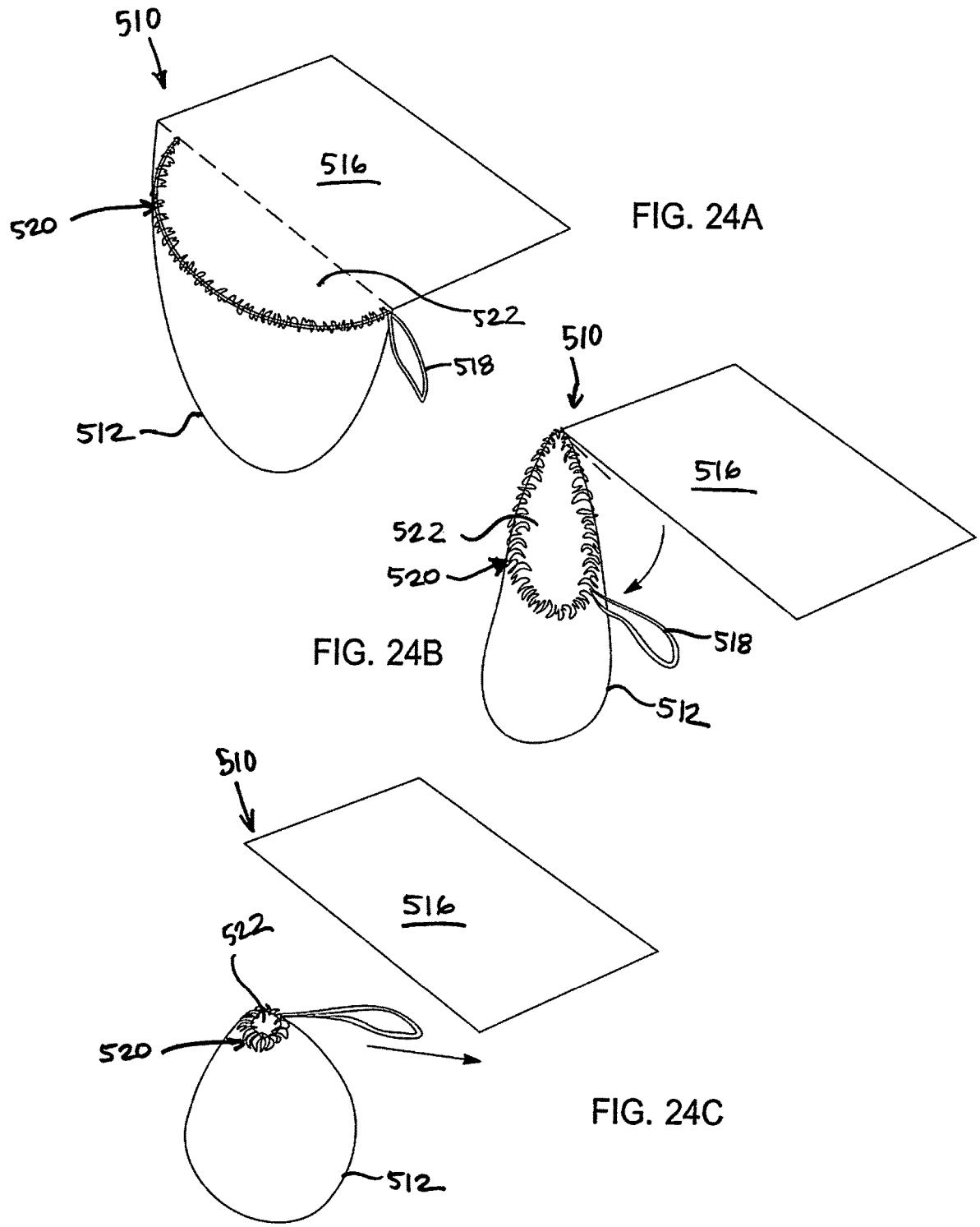

FIGS. 24A-24C illustrate another variation of a device for collecting bodily fluids from a patient during and after childbirth prepared in accordance with certain aspects of the present disclosure, where a collection bag has a closure mechanism for cinching. FIG. 24A shows the collection bag attached to the mat, FIG. 24 B shows the cinching and collection bag removal starting to occur, while FIG. 24C shows the collection bag being removed and fully cinched.

FIGS. 25A-25E illustrate another variation of a device for collecting bodily fluids from a patient during and after childbirth prepared in accordance with certain aspects of the present disclosure, where a collection bag has two tabs and a cinching closure mechanism for a collecting bag. FIGS. 25A-25E show a sequence of detaching, removing, and cinching the collection bag.

Figure 26A:
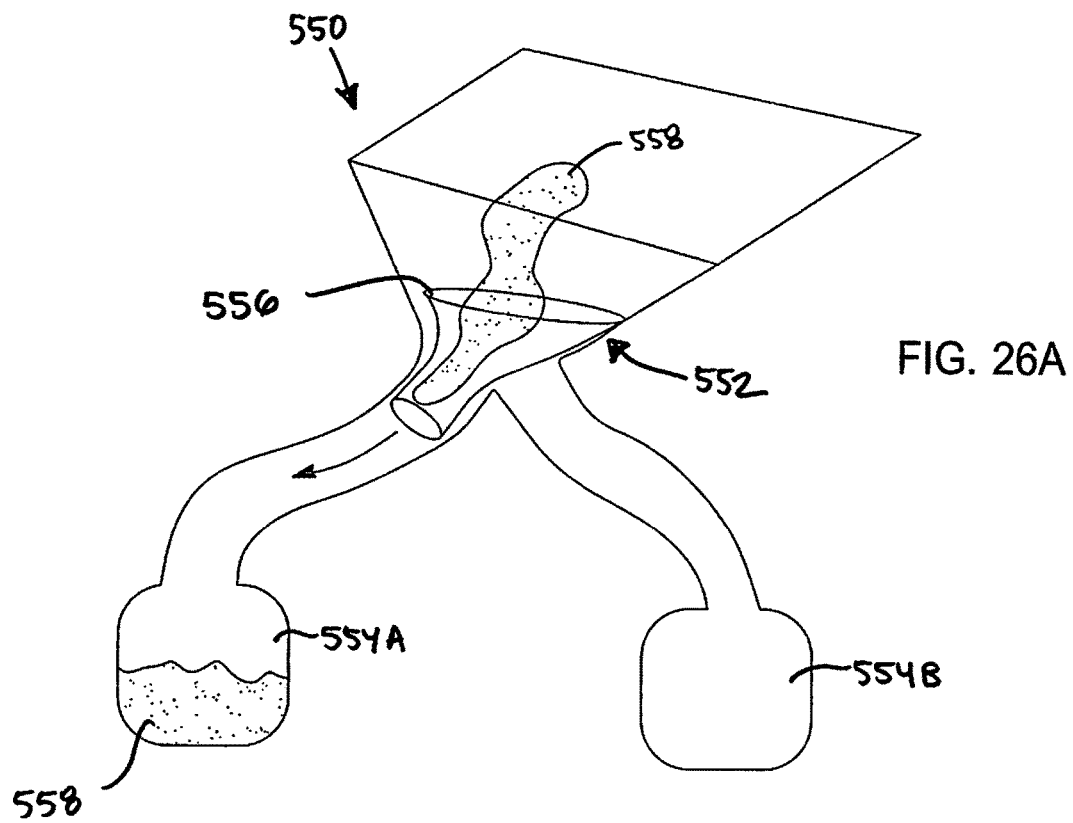
Figure 26B:
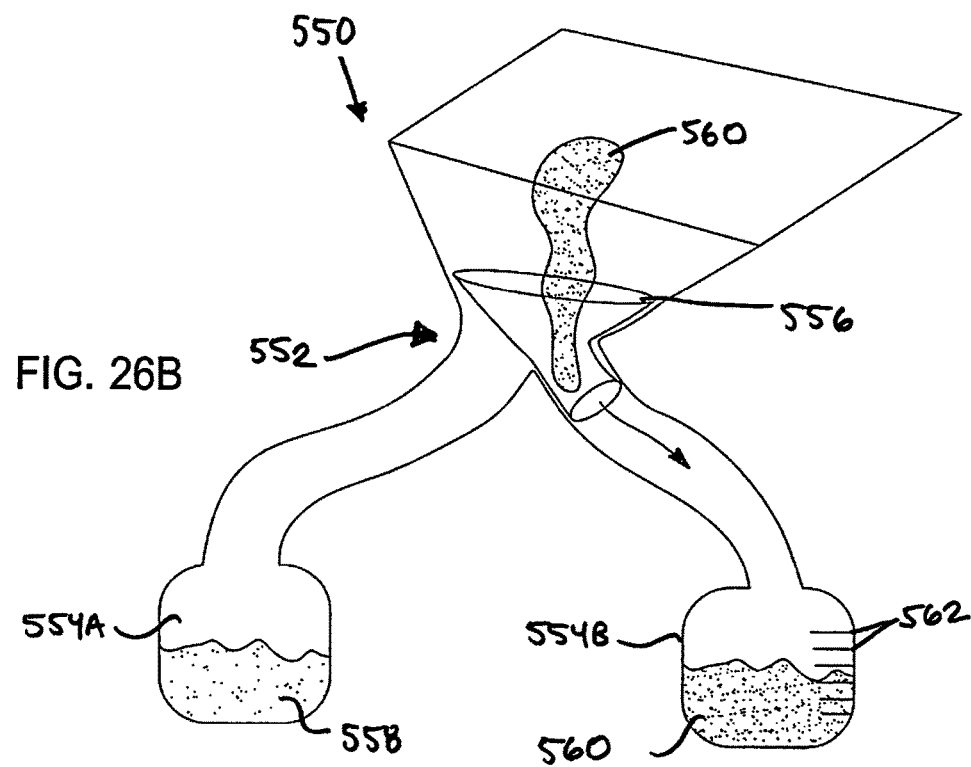

FIGS. 26A-26B illustrate another variation of a device for collecting bodily fluids from a patient during and after childbirth prepared in accordance with certain aspects of the present disclosure, where a collection region includes two distinct collection chambers and a valve or funnel is used to switch between the distinct collection chambers in a first operational mode (shown in FIG. 26A) versus a second operational mode of the device (shown in FIG. 26B).

Figure 27A:
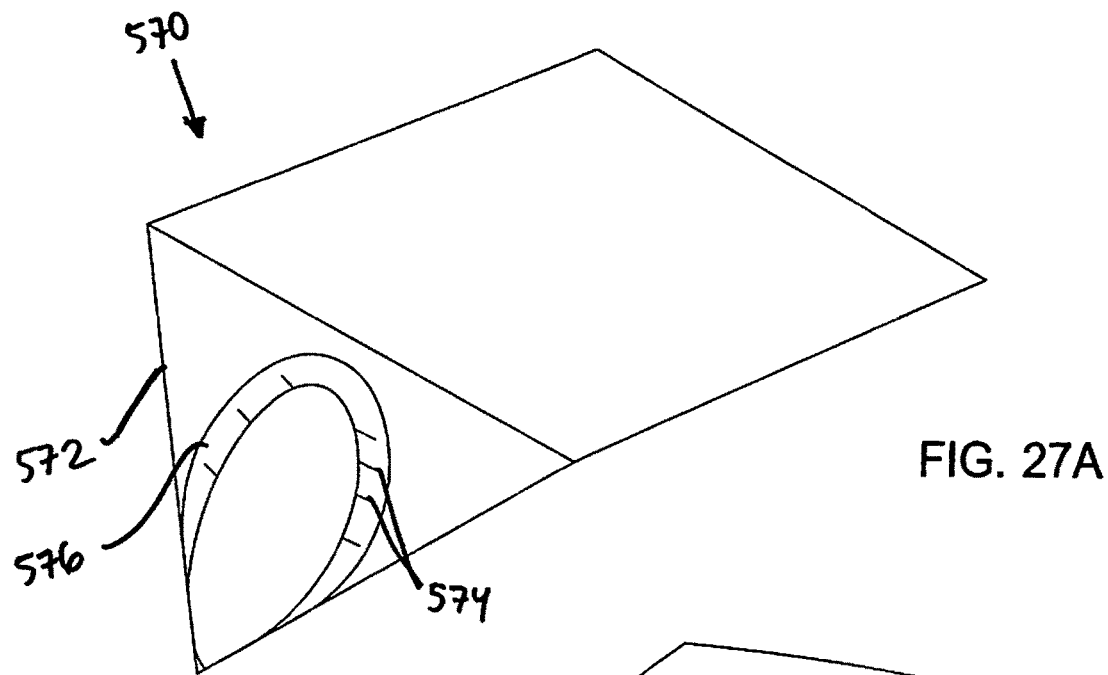
Figure 27B:
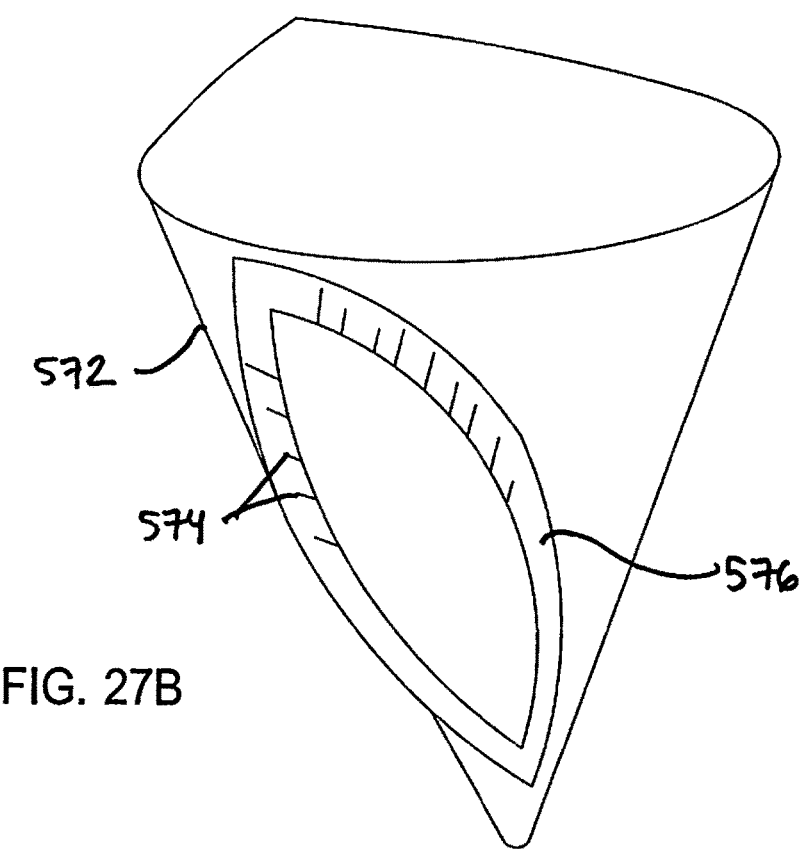

In FIGS. 27A-27B, a device for collecting bodily fluids from a patient during and after childbirth prepared in accordance with certain aspects of the present disclosure has a collecting bag with a visual volume indicator in the form of a ring to measure the bodily fluids collected in the second sealable bag. FIG. 27A shows an isometric view, while FIG. 27B shows a side view.

Figure 28:
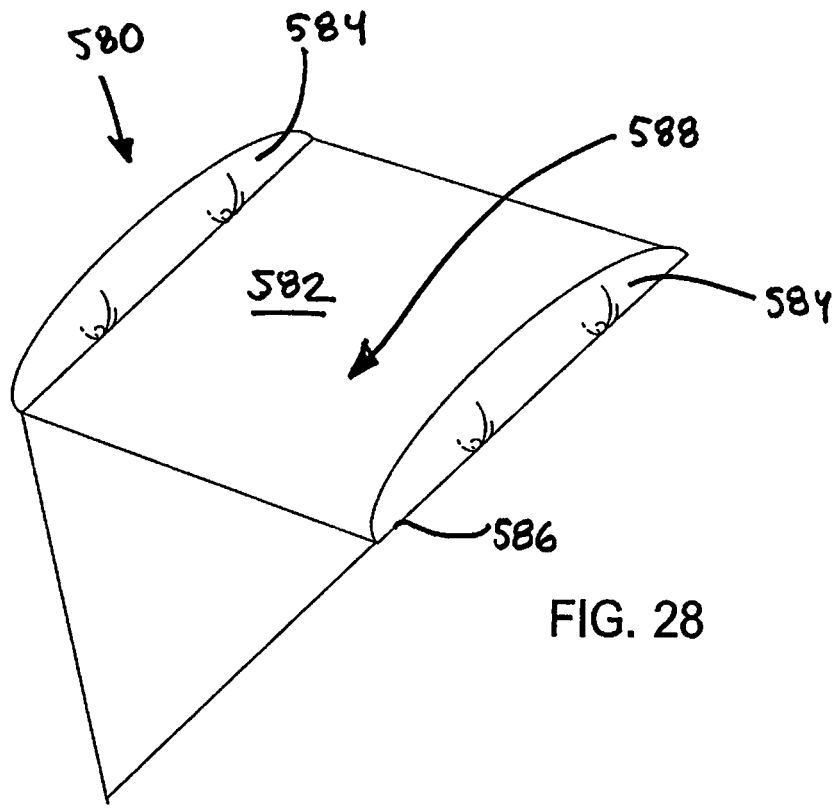

In FIG. 28, a device for collecting bodily fluids from a patient during and after childbirth prepared in accordance with certain aspects of the present disclosure has a mat portion with inflatable dams along peripheral edges to define bumpers.

Figure 29A:
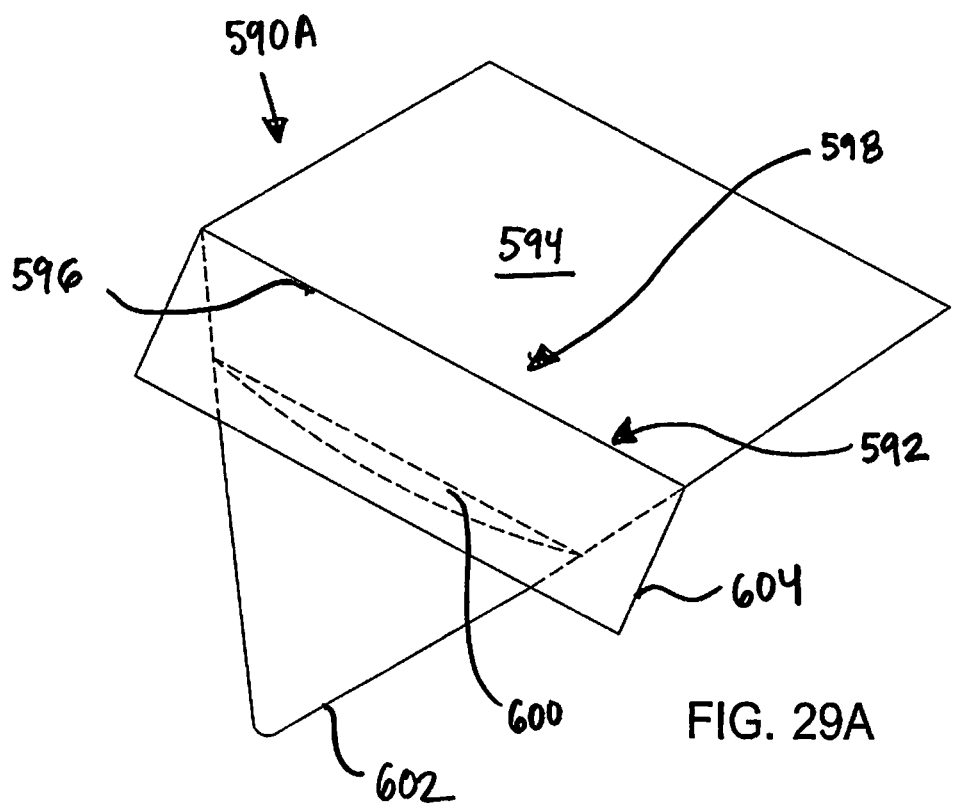
Figure 29B:
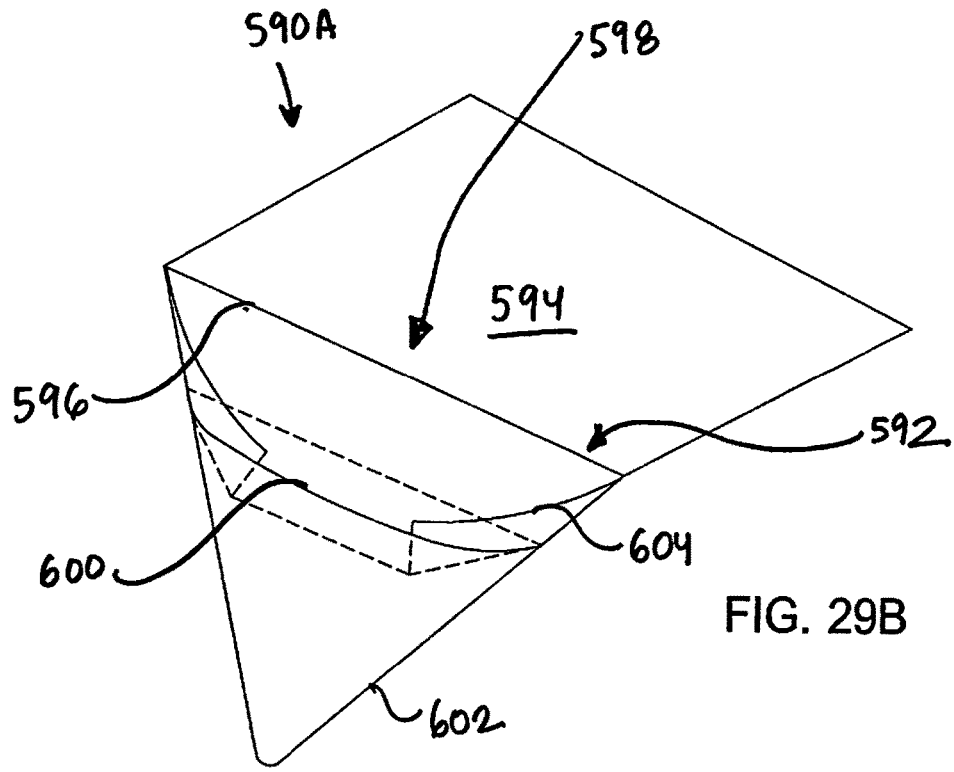
Figure 29C:
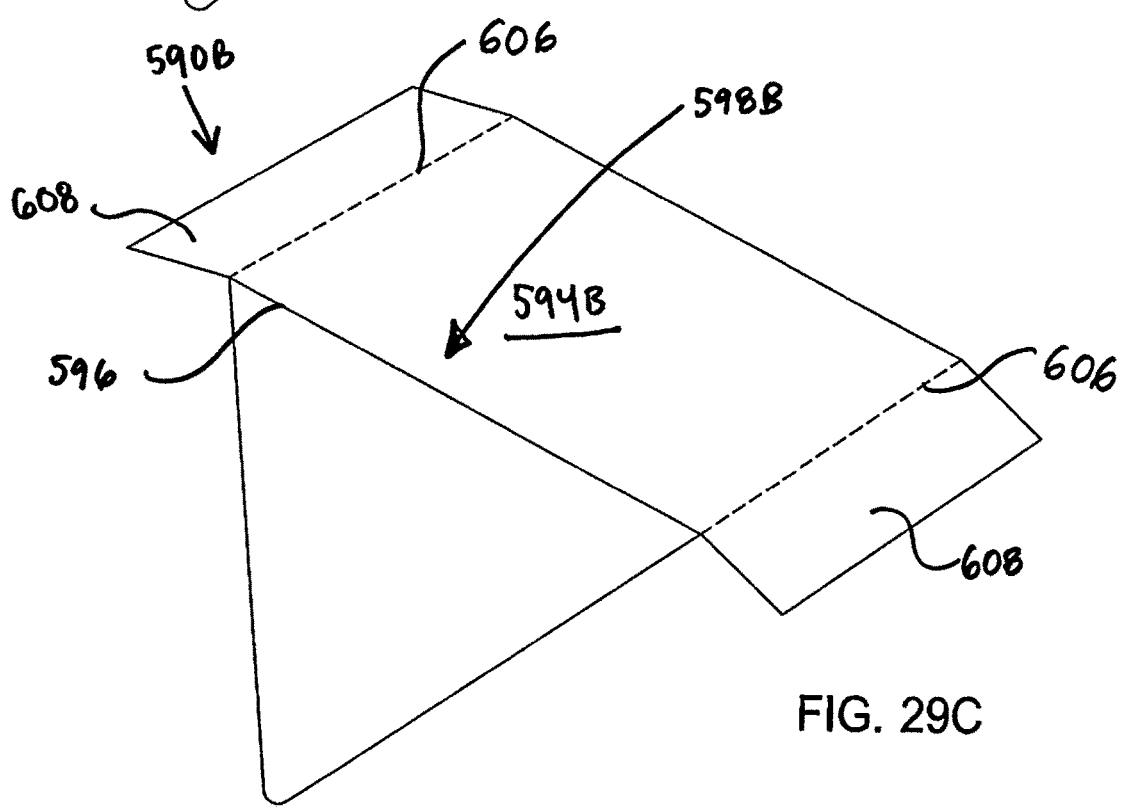
Figure 29D:
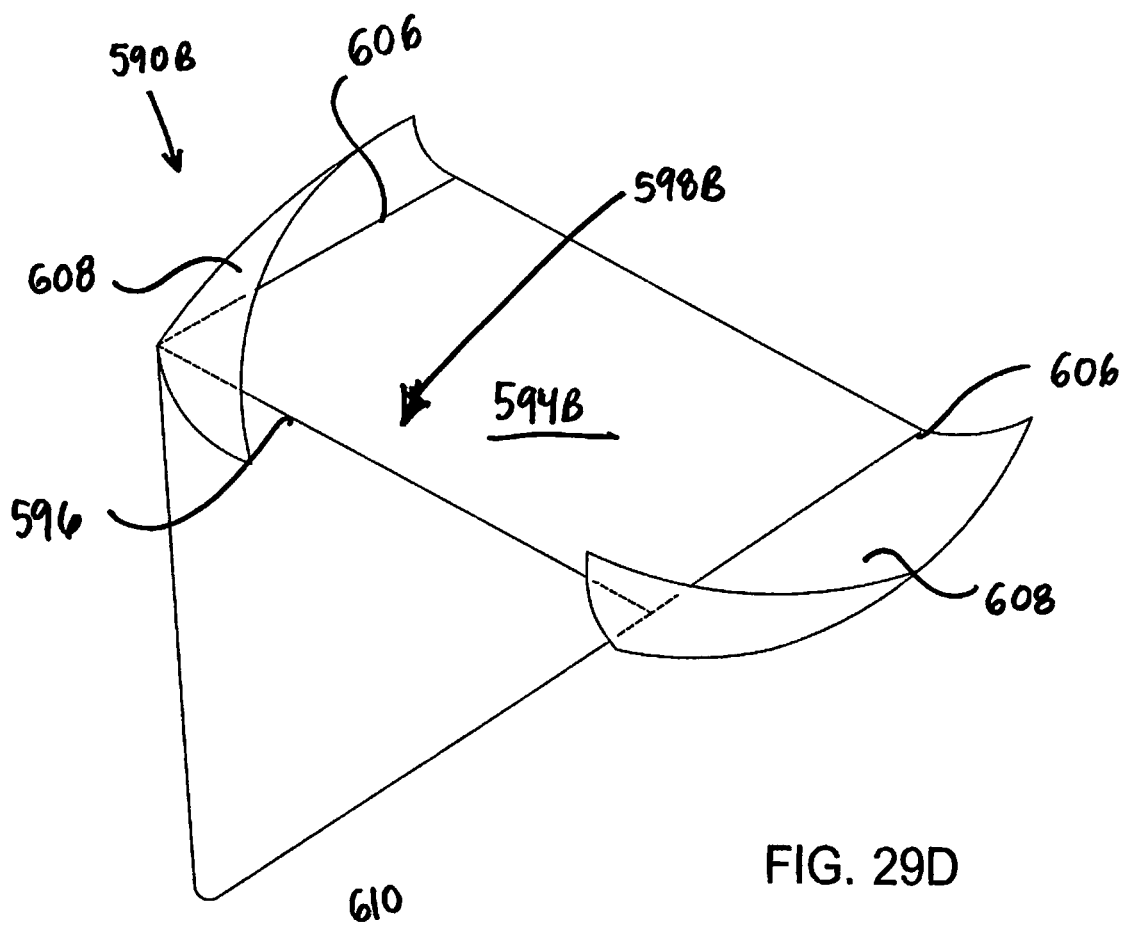

In FIGS. 29A-29D, various embodiments of devices for collecting bodily fluids from a patient during and after childbirth prepared in accordance with certain aspects of the present disclosure have a mat portion incorporating a shape memory material, such as a shape memory polymer. FIGS. 29A-29B show a shape memory material in a tongue portion to guide fluid into a collection bag. FIGS. 29C-29D show a shape memory material used in lateral sides of a mat portion of the device.

Figure 30:
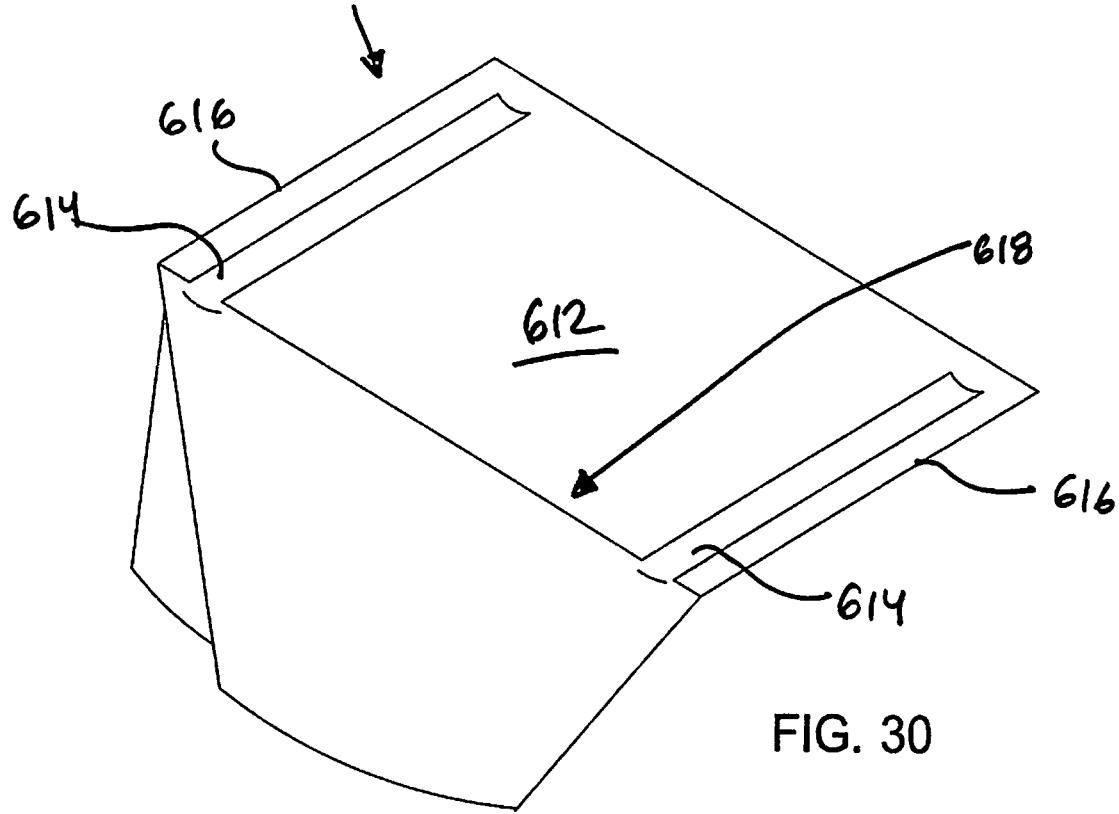

In FIG. 30, a device for collecting bodily fluids from a patient during and after childbirth prepared in accordance with certain aspects of the present disclosure has a mat portion with recessed channels formed along peripheral edges to define fluid flow channels.

Figure 31:
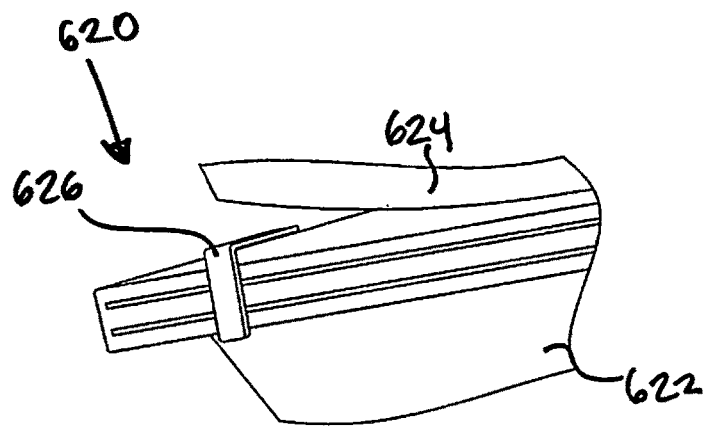

FIG. 31 illustrates an example of a device for collecting bodily fluids from a patient during and after childbirth prepared in accordance with certain aspects of the present disclosure, where a closure mechanism for a collecting bag is capable of both sealing and tearing the collecting bag from a mat portion.

Figure 32:
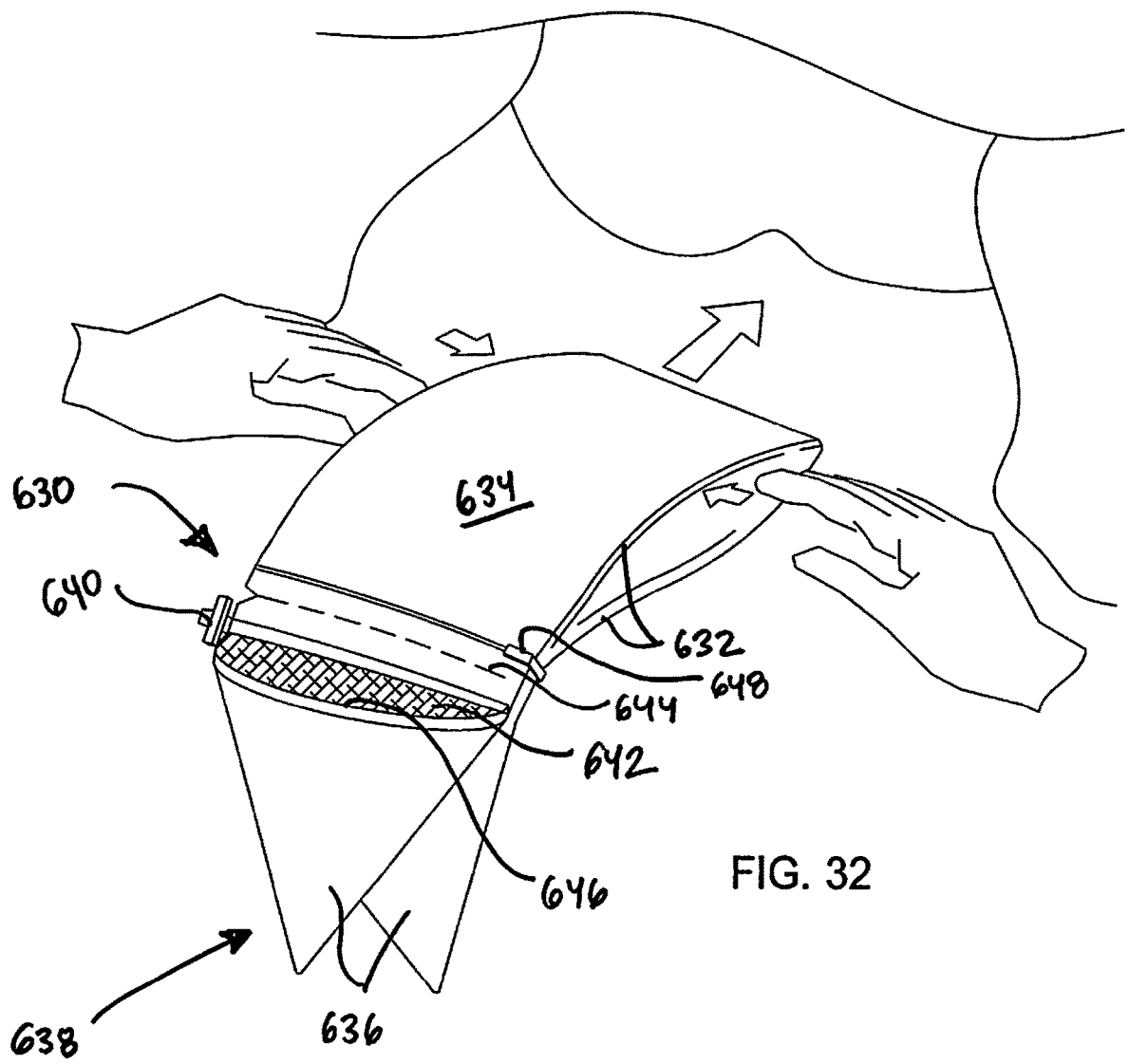

FIG. 32 illustrates an example of a device for collecting bodily fluids from a patient during and after childbirth prepared in accordance with certain aspects of the present disclosure, where a single sheet may be used during manufacturing and heat sealed to itself.

Figure 33:
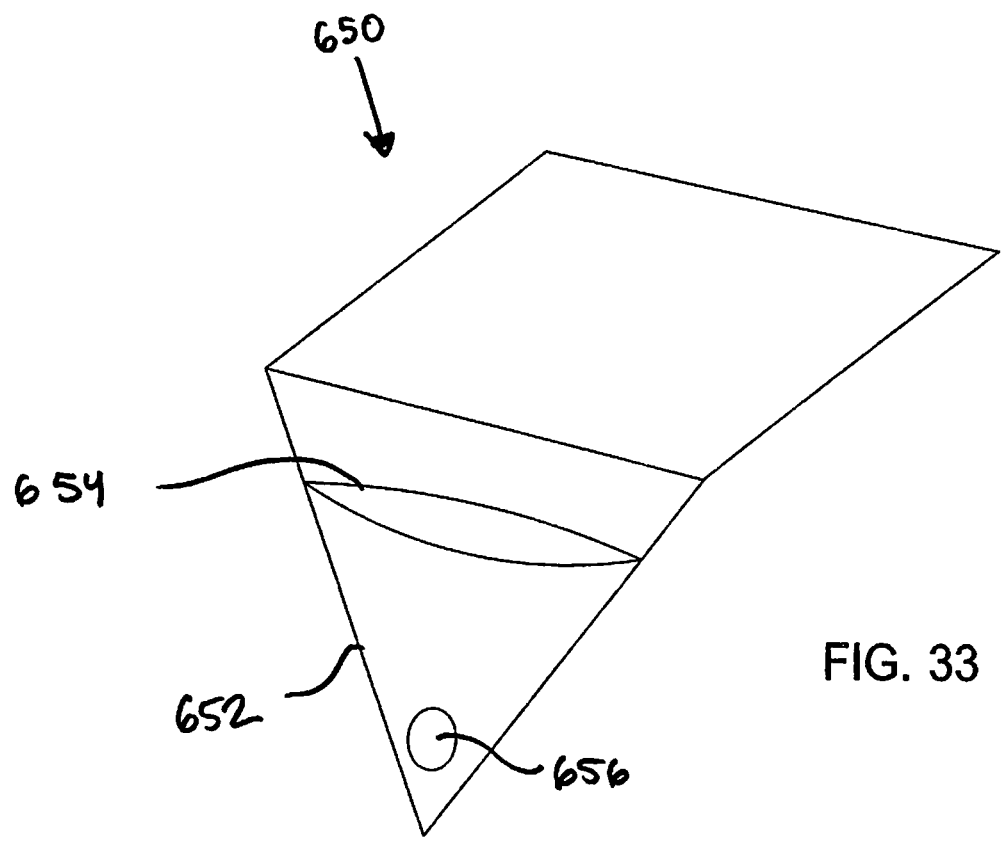

FIG. 33 illustrates another variation of a device for collecting bodily fluids from a patient during and after childbirth prepared in accordance with certain aspects of the present disclosure, where a collection bag comprises an opening to receive bodily fluids and a port for drawing fluids out of the collection bag.

Figure 34A:
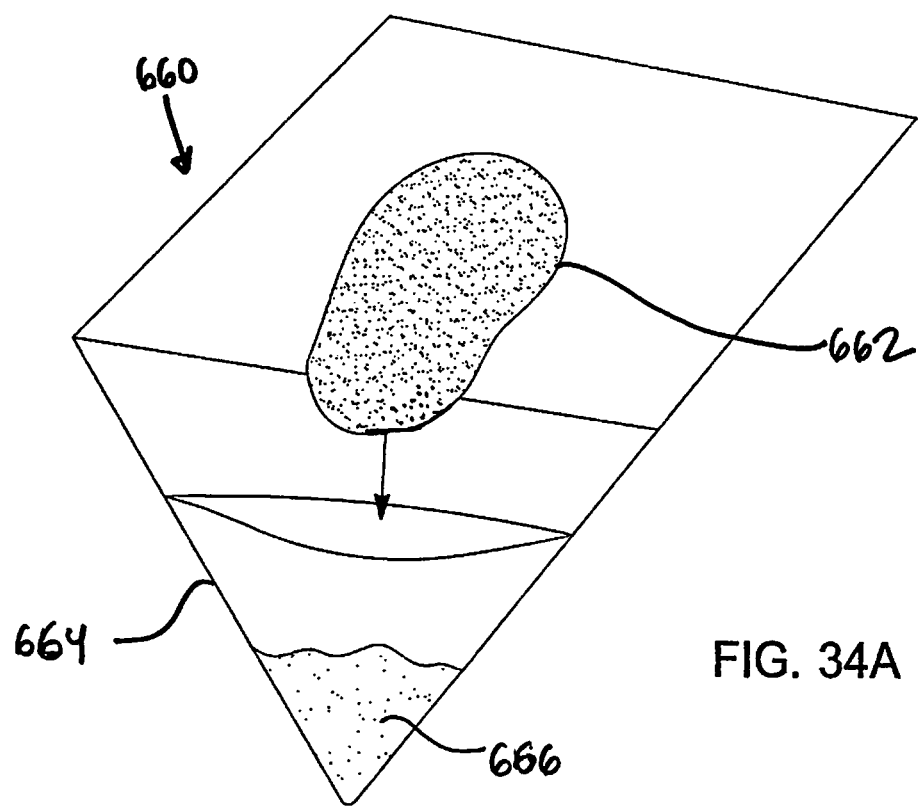
Figure 34B:
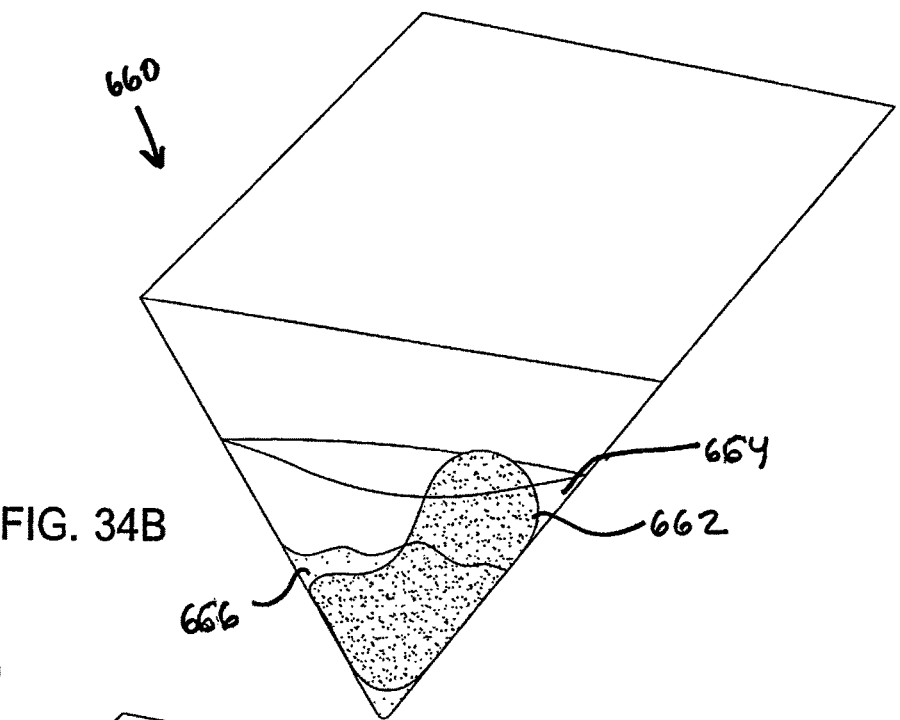
Figure 34C:
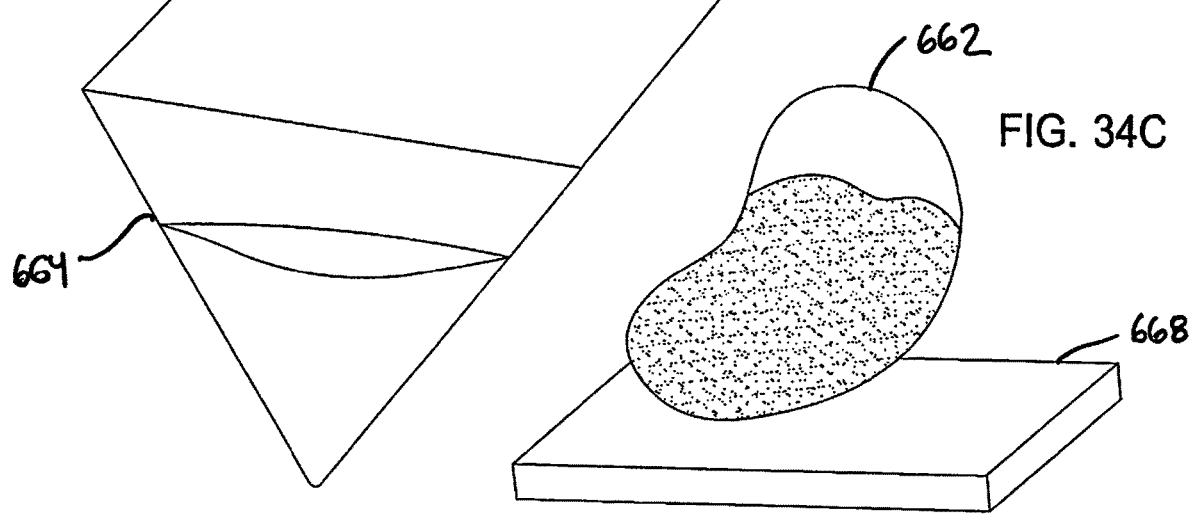

FIGS. 34A-34C illustrate yet another variation of a device for collecting bodily fluids from a patient during and after childbirth prepared in accordance with certain aspects of the present disclosure, where an absorbent material can be used to capture blood from a collection bag. FIG. 34A shows introducing an absorbent material into a collection bag prior to use. FIG. 34B shows blood being captured in the absorbent material. FIG. 34C shows the absorbent material being removed from the collection bag and being weighed.

Figure 35:
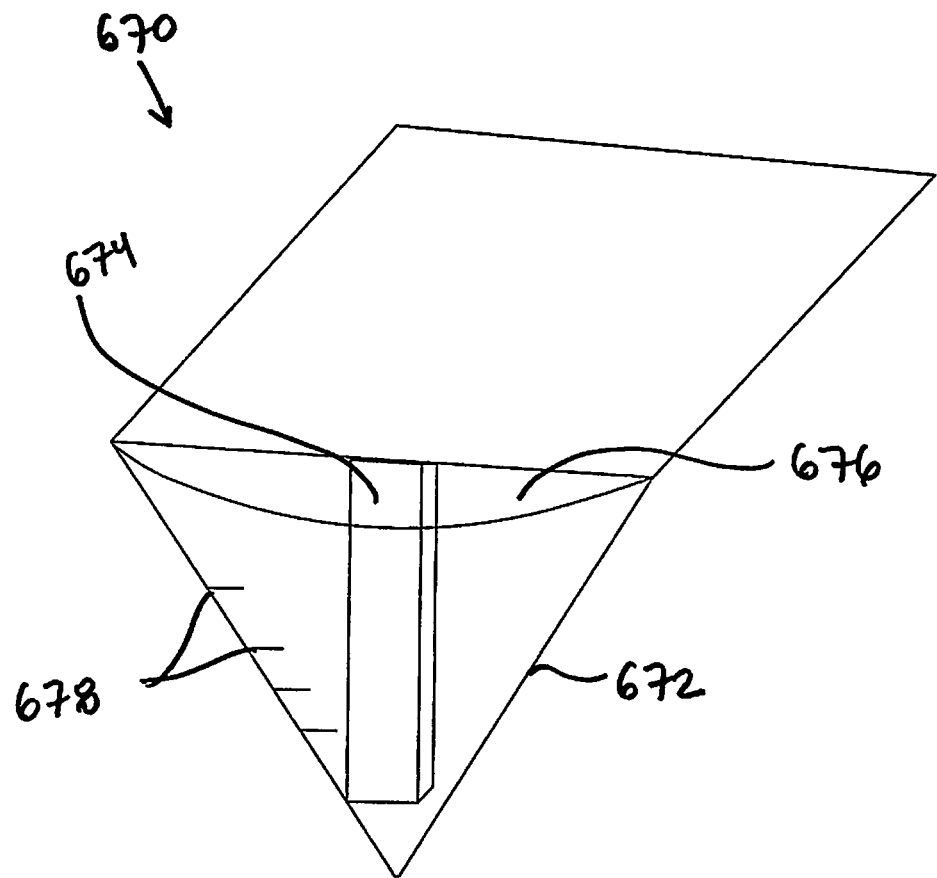

FIG. 35 is another variation of a device for collecting bodily fluids from a patient during and after childbirth prepared in accordance with certain aspects of the present disclosure, where a collection bag has a stiffening or rigid component on a back side of a second collection bag to enhance visibility of a visual volume indicator.

FIGS. 36A-36D show two other variations of devices for collecting bodily fluids from a patient during and after childbirth prepared in accordance with certain aspects of the present disclosure. In one variation shown in FIGS. 36A-36B, a mat portion can be unrolled beneath the patient by pulling a tab. In another variation shown in FIGS. 36C-36D, a mat portion can be unrolled beneath the patient by pulling two straps on terminal edges of the rolled mat portion.

Figure 37A:
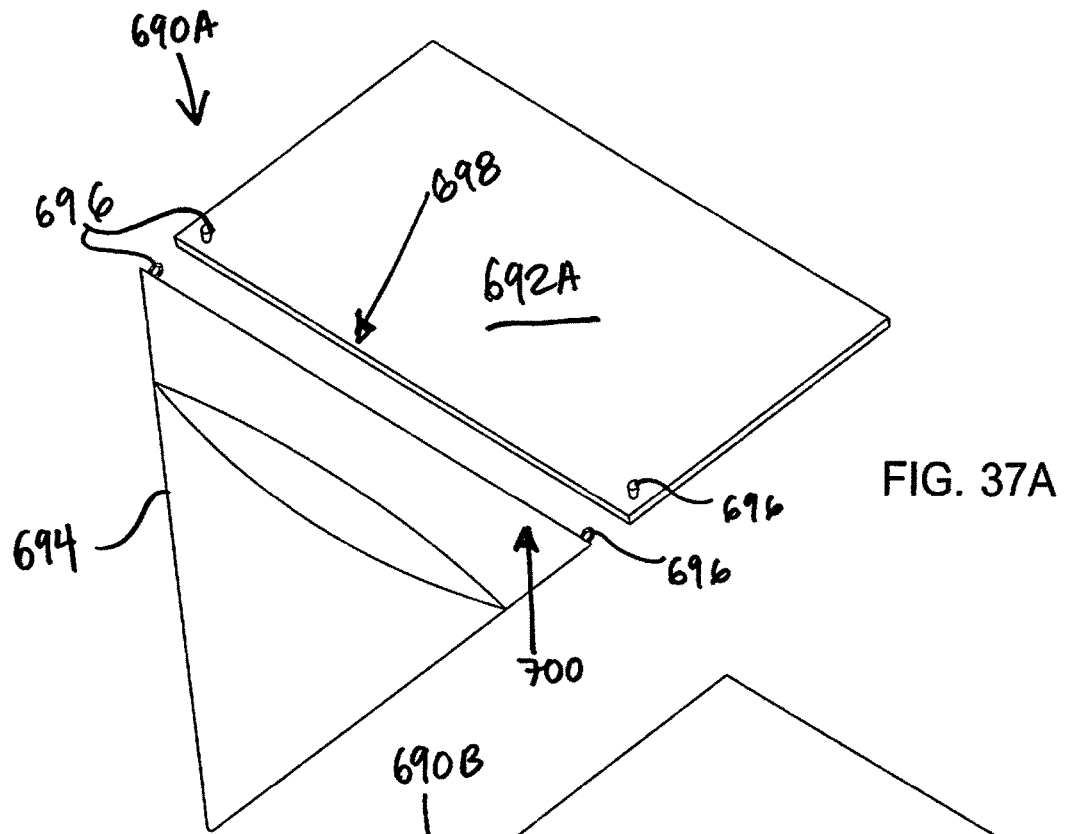
Figure 37B:
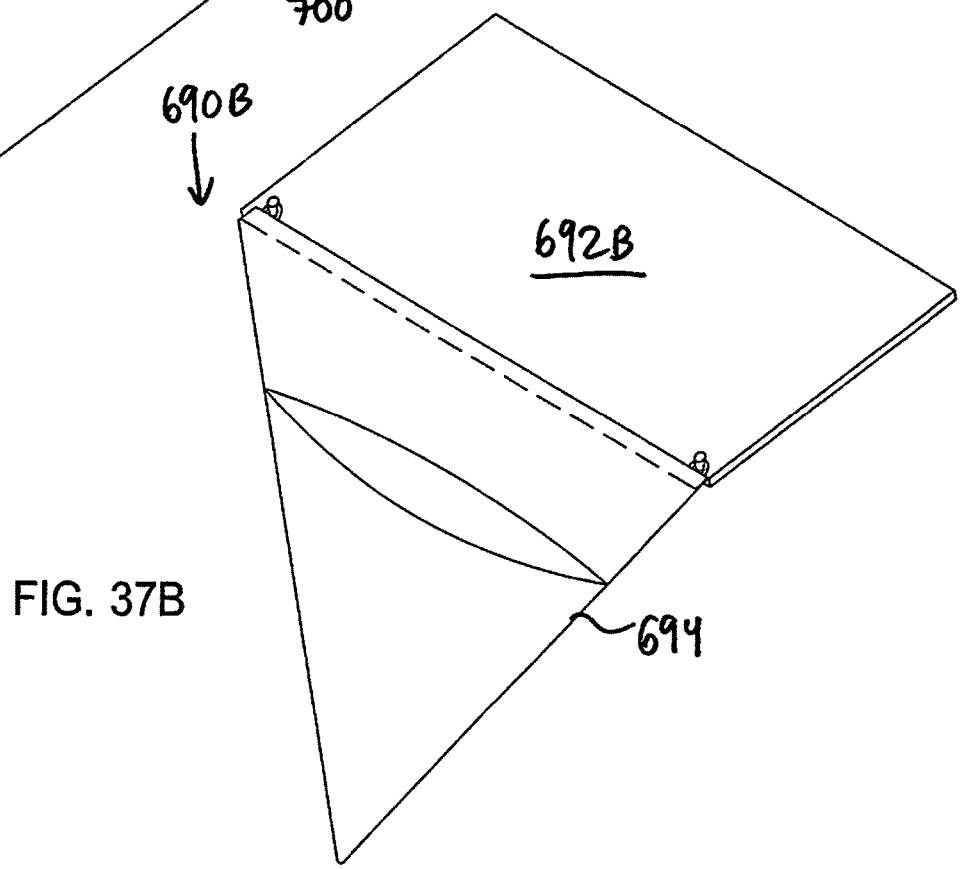

FIGS. 37A-37B shows another variation of a device for collecting bodily fluids from a patient during and after childbirth prepared in accordance with certain aspects of the present disclosure, where a mat portion is reusable and first and second collection bags are disposable. FIG. 37A shows the removal of the collection bag from the reusable mat. FIG. 37B shows another variation of multiple attachable reusable compartments.

Figure 38:
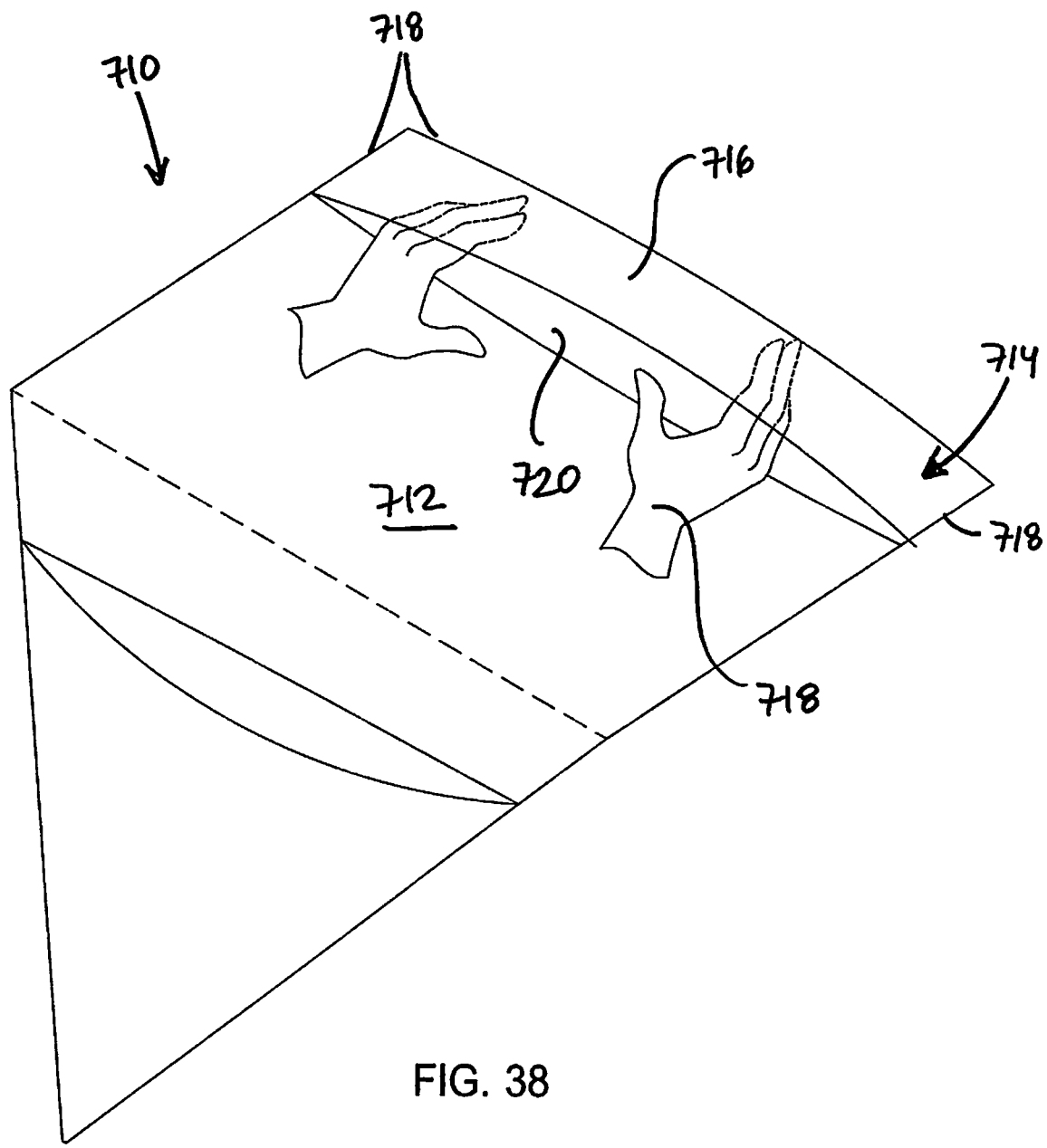

FIG. 38 is an example of a device for collecting bodily fluids from a patient during and after childbirth prepared in accordance with certain aspects of the present disclosure having a mat portion with a proximal end including a flap or folded region.

Figure 39D:
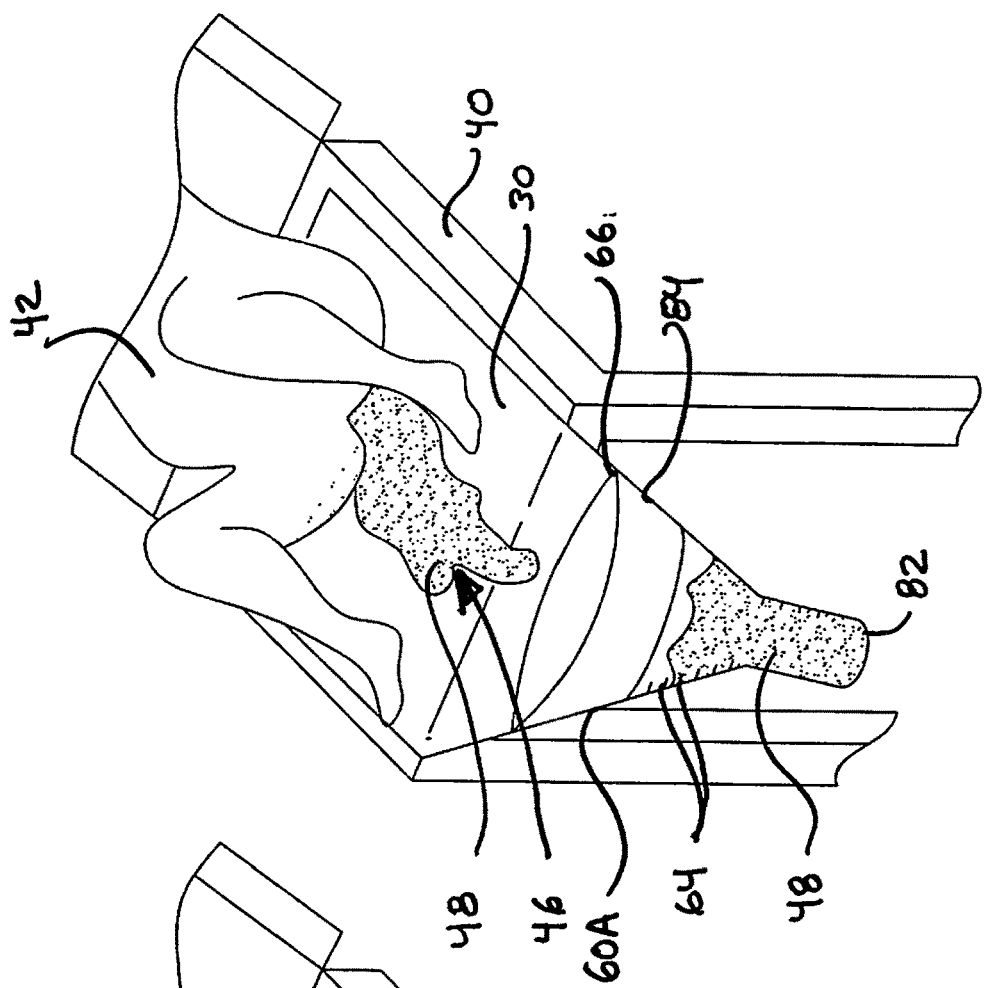
Figure 39C:
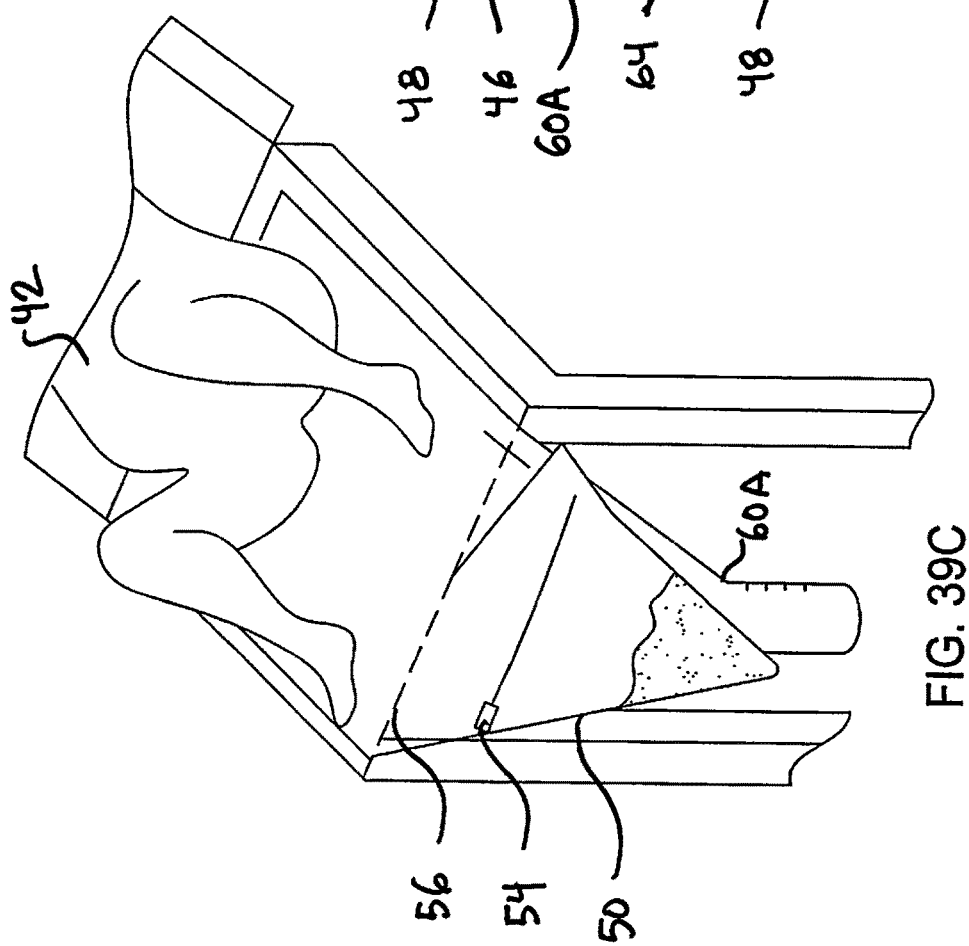
Figure 39E:
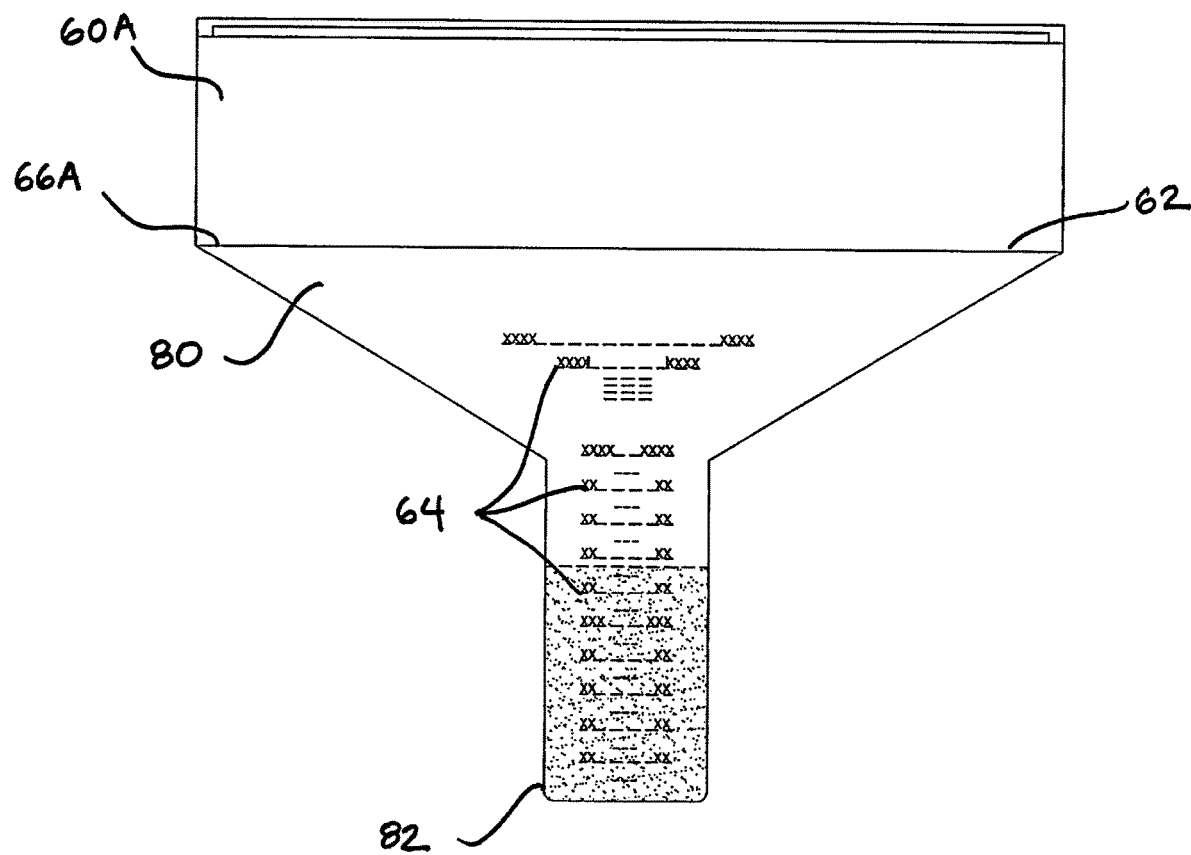

FIGS. 39A-39E show a device for collecting bodily fluids from a patient during and after childbirth prepared in accordance with certain aspects of the present disclosure, where a first detachable collection bag has a first shape, shown to be a triangular (or conical) shape for a first operational mode of the device, while a second collection bag for a second operational mode may have a different shape from the first collection bag, here shown to be a wineglass or a shape having an entry regions that is hemispherical or cone shaped connected to a rectangular or cylinder vessel for volumetric measurement. FIG. 39A shows a first operational mode of the device where the device is disposed between a patient and a support (e.g., hospital bed) and collects bodily fluids from the patient. FIG. 39B shows a first detachable and sealable bag being sealed. FIG. 39C shows a transition between the first operational mode and a second operational mode of the device. FIG. 39D shows the device collecting bodily fluids from the patient during the second operational mode. FIG. 39E shows a second collection bag having the a shape having an entry regions that is hemispherical or cone shaped connected to a rectangular or cylinder vessel for volumetric measurement.

Figure 40:
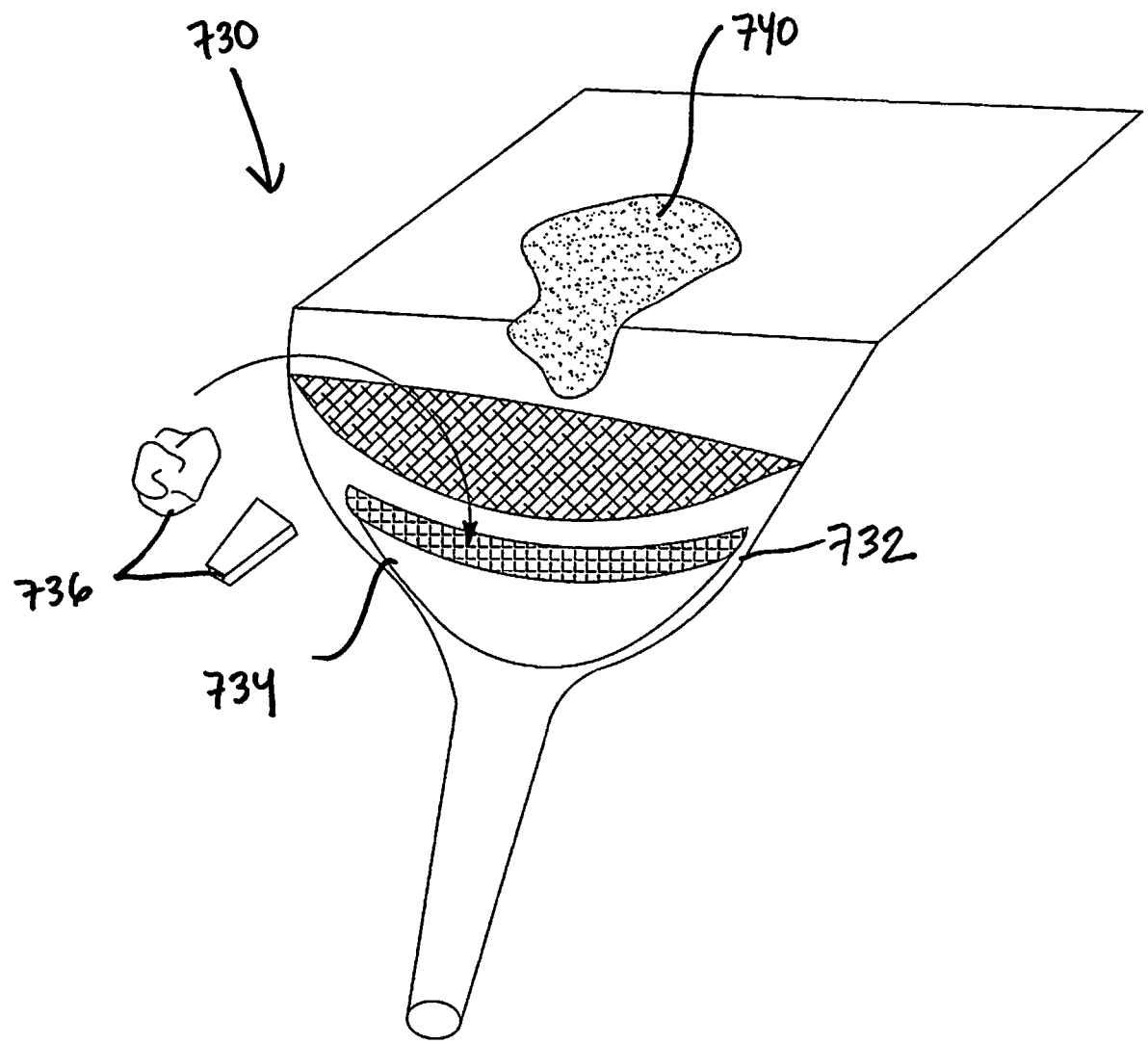

FIG. 40 shows a device for collecting bodily fluids from a patient during and after childbirth prepared in accordance with certain aspects of the present disclosure, where a collection bag has an additional compartment to hold dry waste.

FIGS. 41A-41G show a device for collecting bodily fluids from a patient during and after childbirth prepared in accordance with certain aspects of the present disclosure. In FIG. 41A-41G, a first detachable collection bag has a first shape for a first operational mode of the device, while a second collection bag for a second operational mode may have a distinct second shape. In certain variations, the first shape may be triangular (or conical). The first shape may be selected from one of an isosceles triangle and an isosceles trapezoid. A portion of the second shape may include an entry region defining a triangular, quadrilateral, or pentagon shape connected to the graduated cylinder. A lower portion of the second shape may be a rectangle from a two dimensional perspective that is in the form of a graduated cylinder in three dimensions.

Figure 41A:
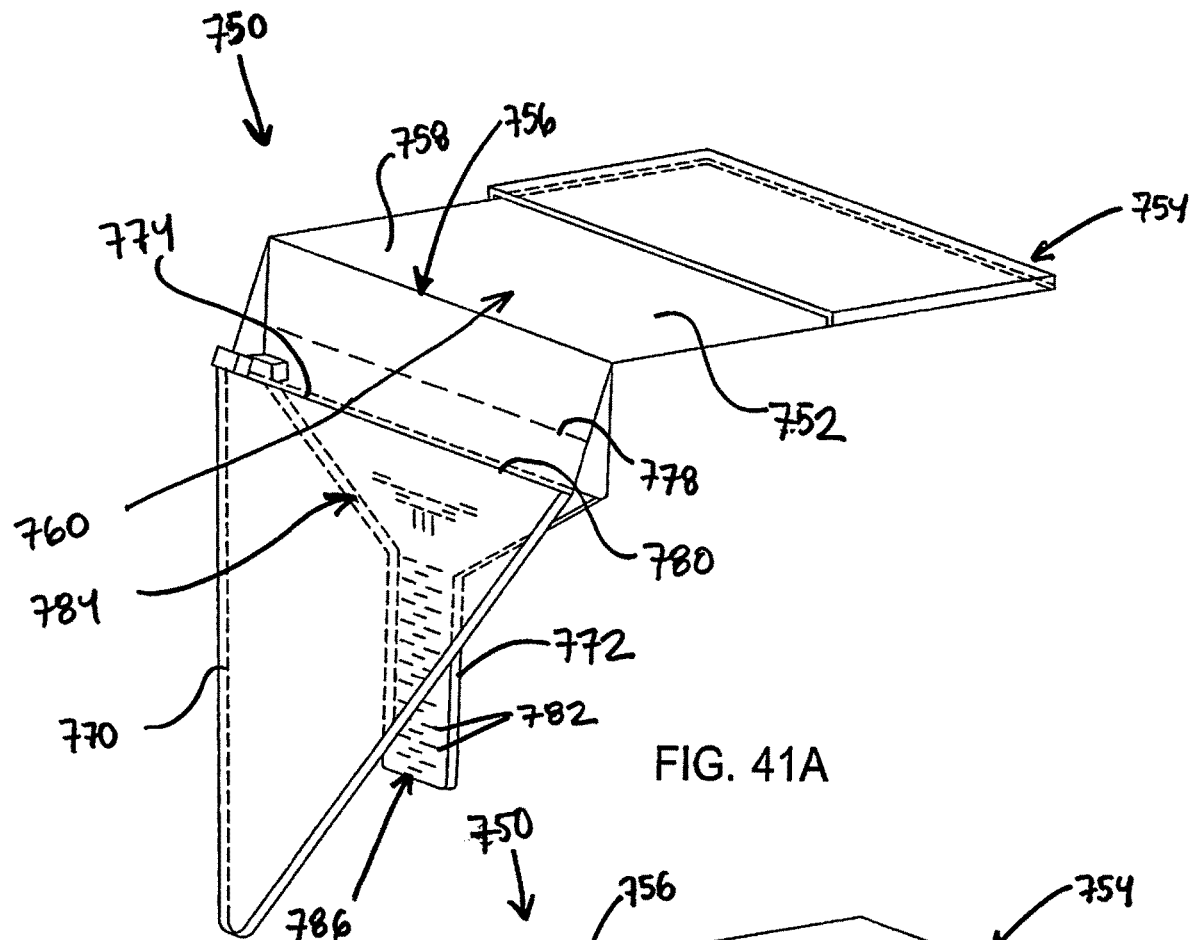
Figure 41B:
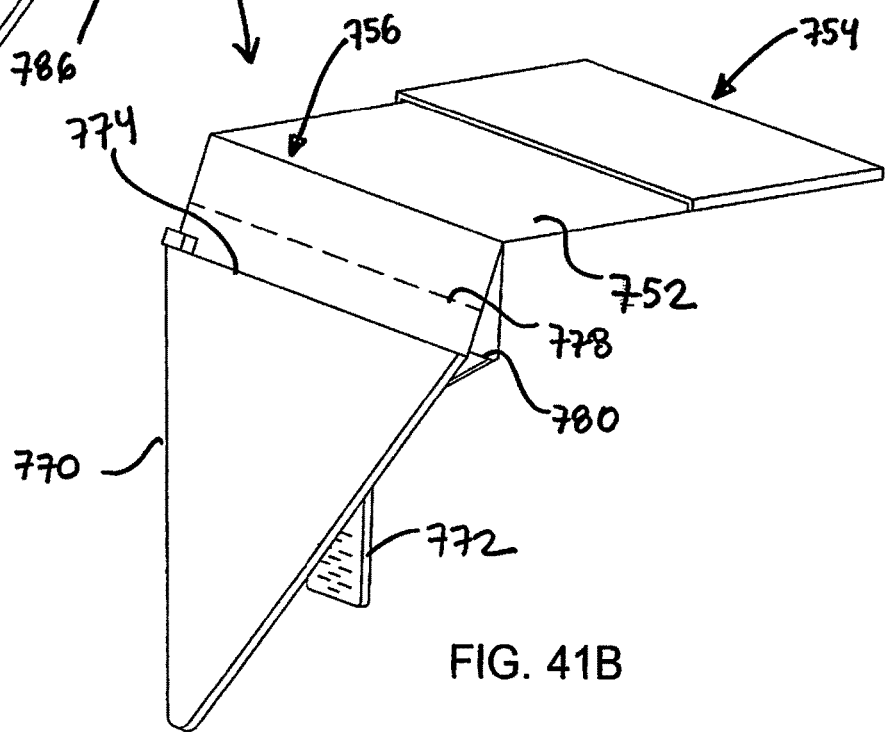
Figure 41F:
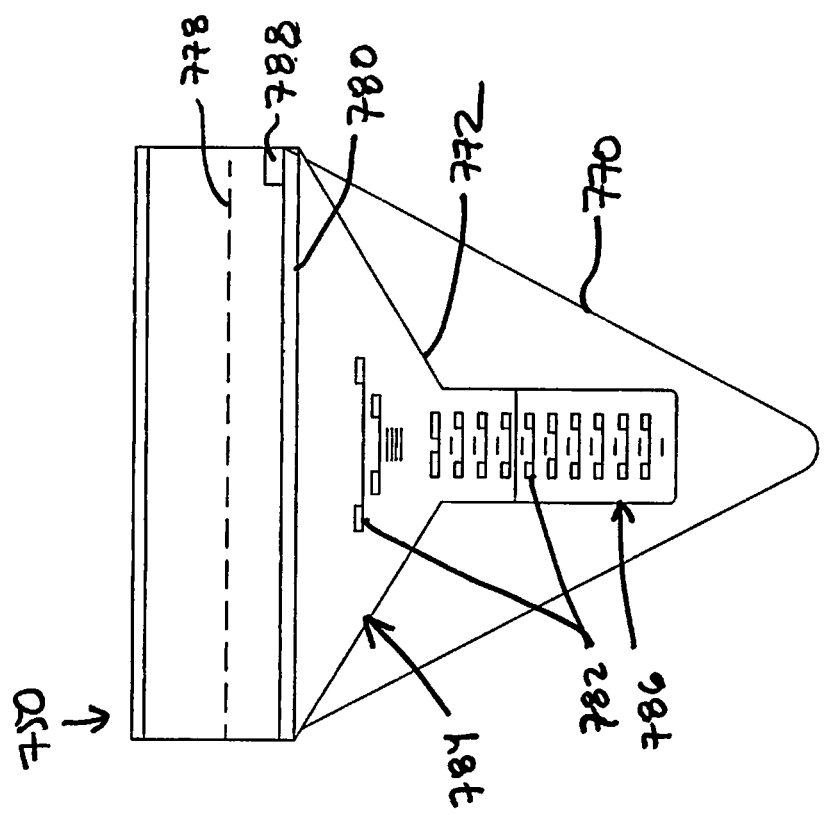
Figure 41E:
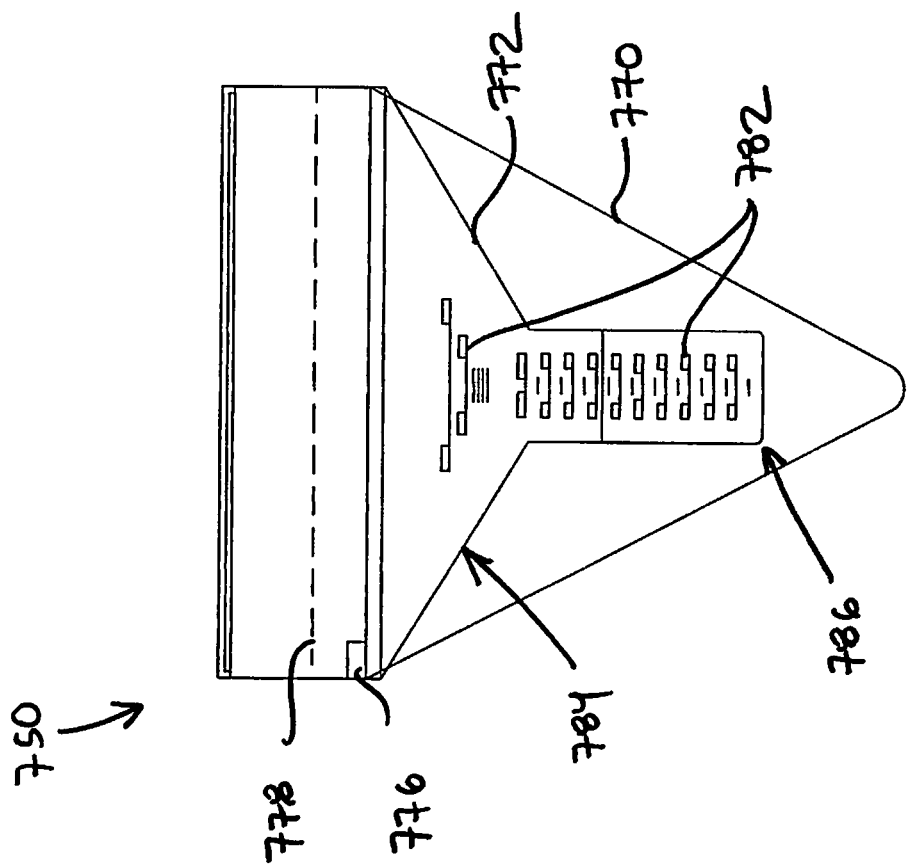
Figure 41G:
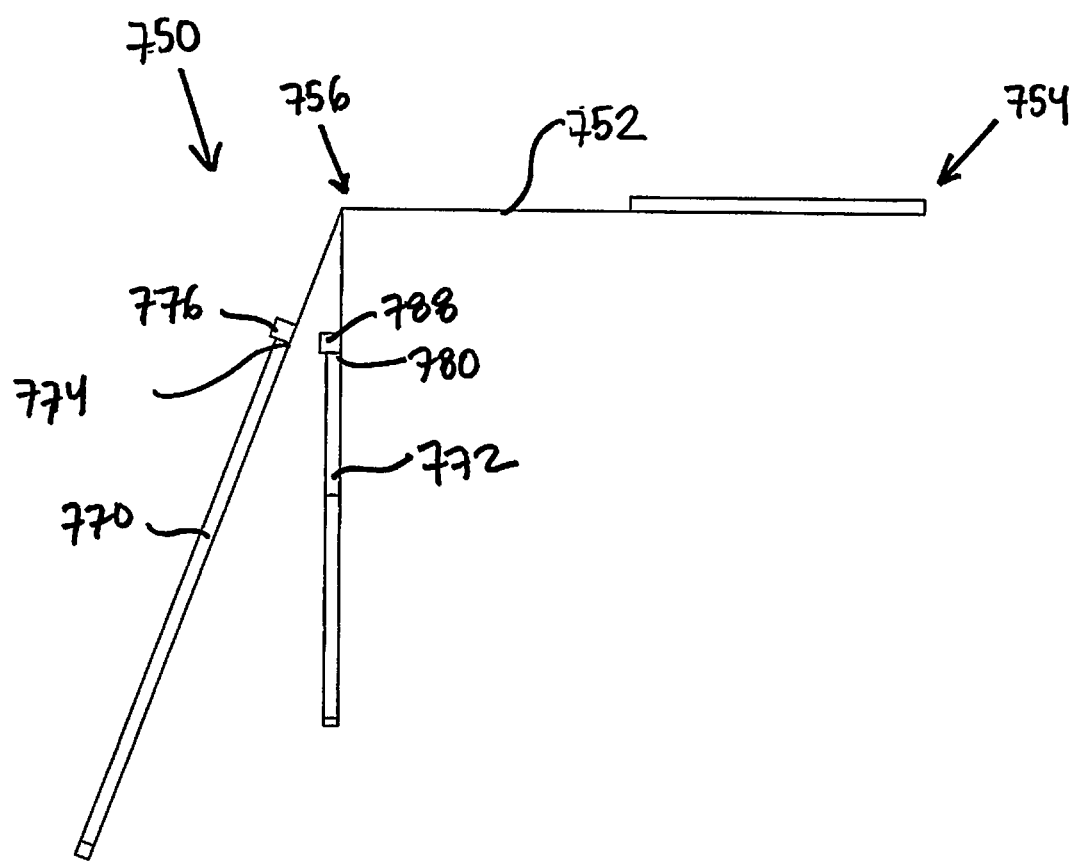

Thus, as shown in FIGS. 41A-41G, the second collection bag may have a triangular (conical) upper region that transforms to a rectangular (cylinder) lower region having indicia to measure volume of fluids collected. FIG. 41A is a perspective view of the device for collecting bodily fluids from a patient during and after childbirth prepared in accordance with certain aspects of the present disclosure, including details of a first collection bag having a first triangular shape and a second collection bag having a distinct shape disposed behind the first collection bag. FIG. 41B is a perspective view of the device showing the first collection bag and visible regions of the second collection bag disposed behind the first collection bag. FIG. 41C is a top view of the device showing the first collection bag. FIG. 41D is a bottom view of the device showing the second collection bag visible and separated from the first collection bag. FIG. 41E is a front planar view of the first collection bag and second collection bag disposed behind the first collection bag. FIG. 41F is a back planar view of the second collection bag disposed behind the first collection bag. FIG. 41G is a side view of the device for collecting bodily fluids from a patient during and after childbirth prepared in accordance with certain aspects of the present disclosure.

Figure 42A:
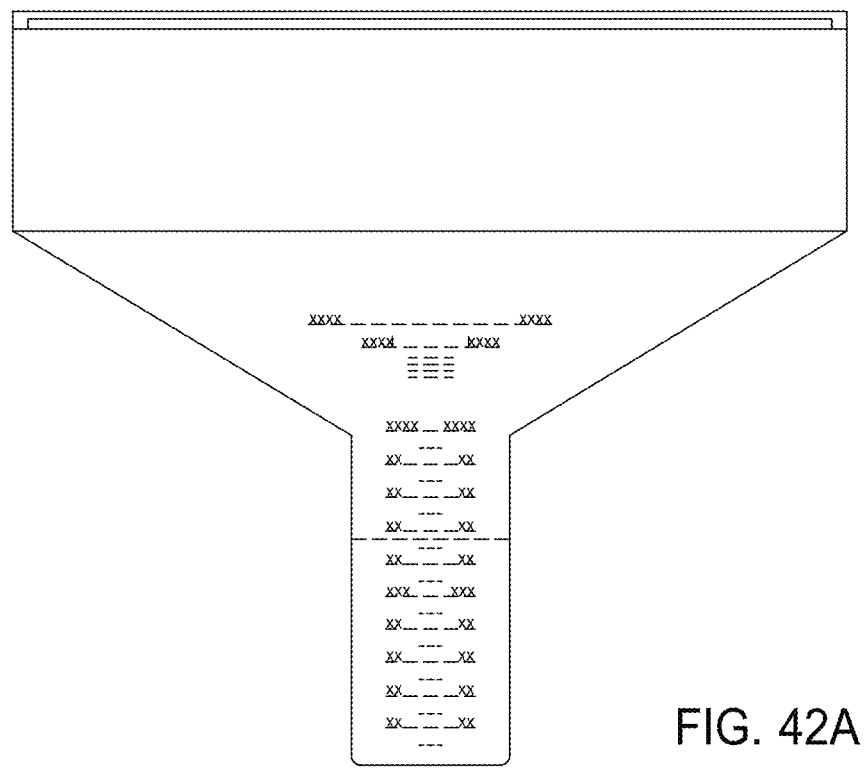
Figure 42B:
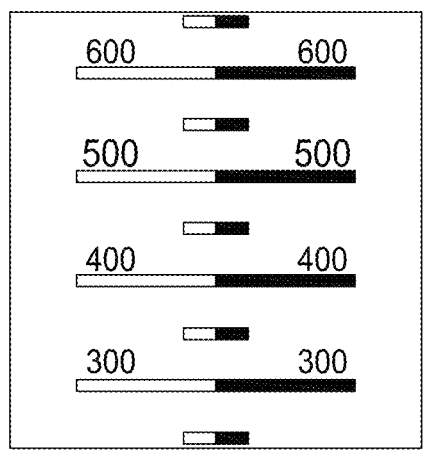

FIGS. 42A-42B show a variation of a design of a second collection bag for a device according to the present disclosure having a triangular (or conical) upper region that transforms to a cylinder lower region having indicia to measure volume of fluids collected. FIG. 42B shows a detailed view of the indicia to measure volume of fluids, including one half of each marking and volumetric amount being a light color (e.g., white text and lines) and one half of each marking and volumetric amount being a dark color (e.g., black text and lines). The second collection bag with marked gradations can be collected and can quantify hemorrhaging blood accurately after the placenta is delivered.

Figure 43A:
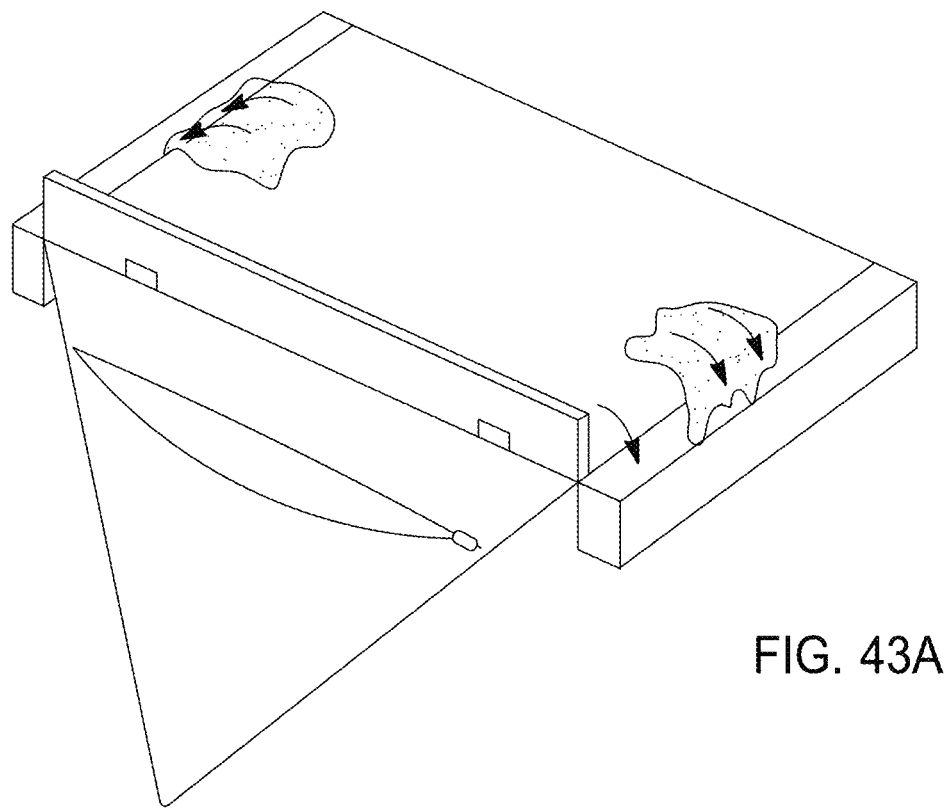
Figure 43B:
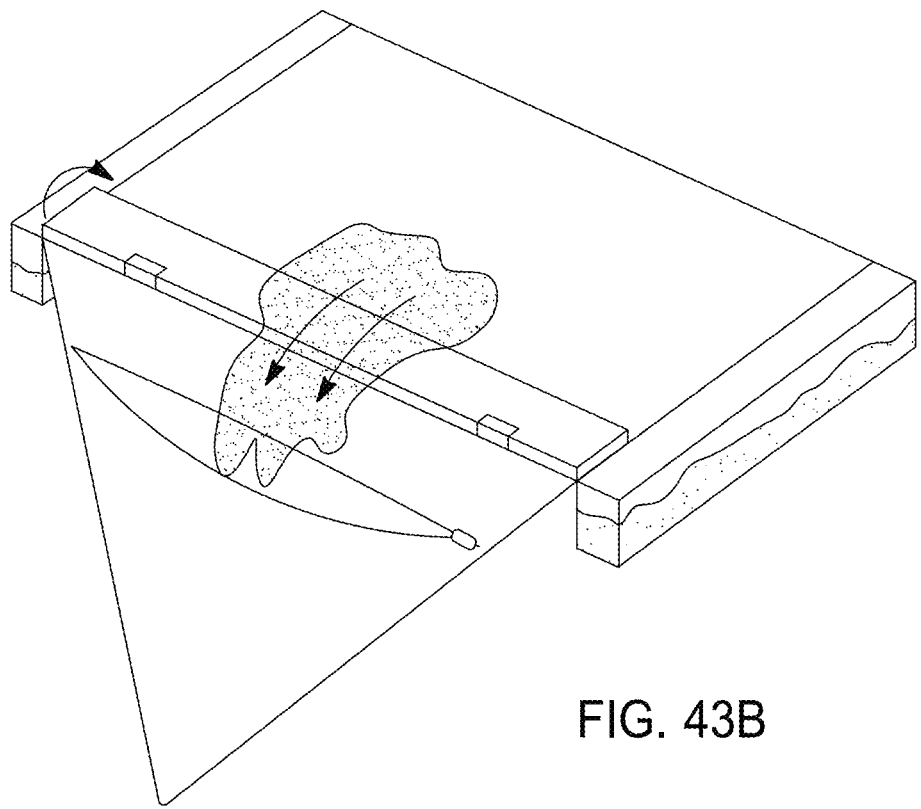

FIGS. 43A-43B show a device for collecting bodily fluids from a patient during and after childbirth prepared in accordance with certain aspects of the present disclosure where a distal region of the mat can be used to distinguish and separate fluids.

Figure 44:
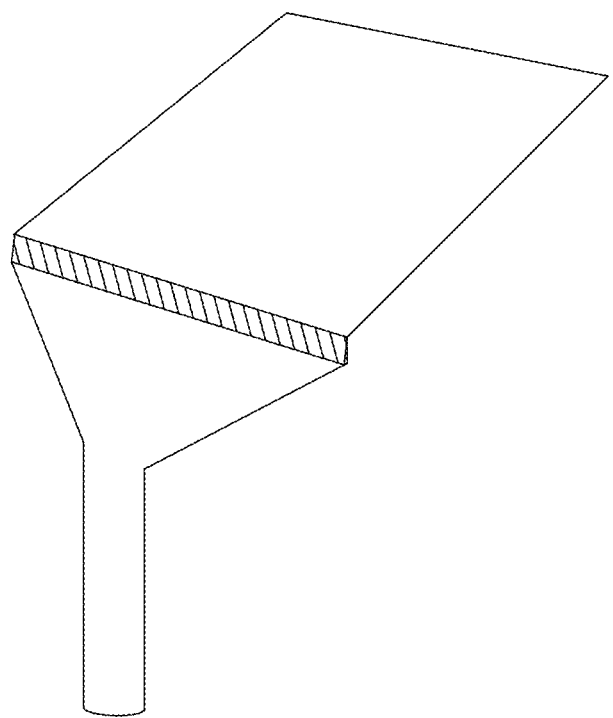

FIG. 44 shows a device for collecting bodily fluids from a patient during and after childbirth having a permanent collection bag connected with the mat prepared in accordance with certain aspects of the present disclosure.

Figure 45A:
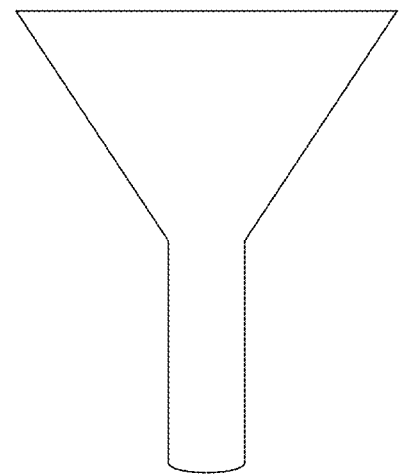
Figure 45B:
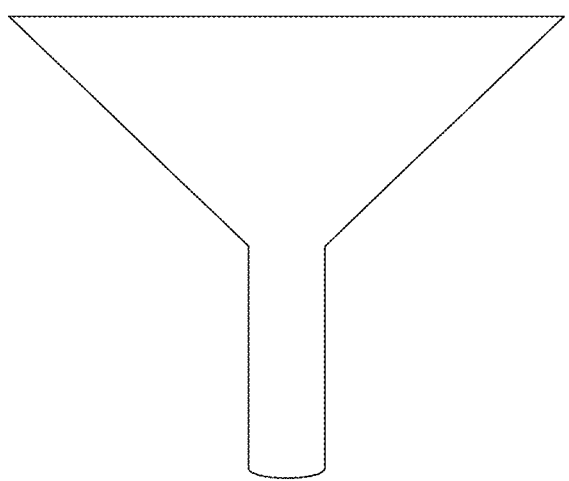
Figure 45C:
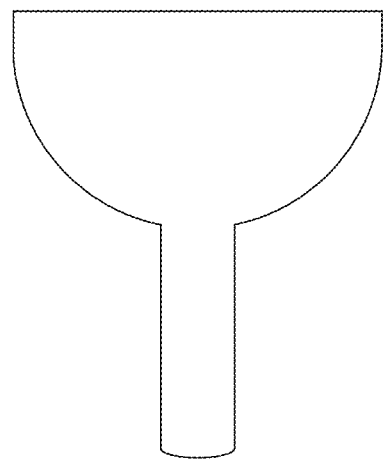
Figure 45D:
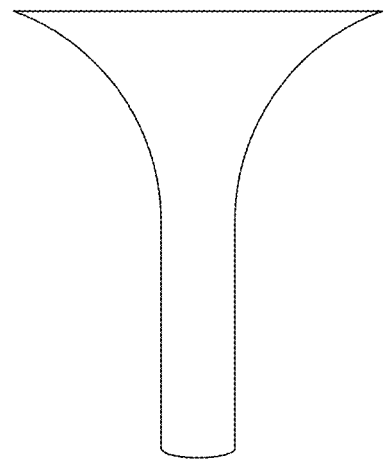

FIGS. 45A-45D show several variations of designs for a second collection bag for a device according to the present disclosure having an upper region that transforms to a rectangular (cylindrical) lower region to measure volume of fluids collected. The graduated cylinder shape in the lower region in the second collection bag can provide more accurate measurement. FIG. 45A shows a triangular (or conical) upper region with shorter sides and thus having a smaller volume that transitions to a cylindrical lower region. FIG. 45B shows another variation of a wider triangular (or conical) upper region with longer sides and a greater volume that transitions to a cylindrical lower region. FIG. 45C shows another variation of a hemispherical upper region that transitions to a cylindrical lower region. FIG. 45D shows a fluted or tulip upper region that transitions to a cylindrical lower region.

FIGS. 46A-46E show successive steps for use of a device for collecting bodily fluids from a patient during and after childbirth having a concurrent tear away and prop open drapes and a first collection bag having a closure mechanism in the form of a cinching mechanism prepared in accordance with certain aspects of the present disclosure.

Figure 47:
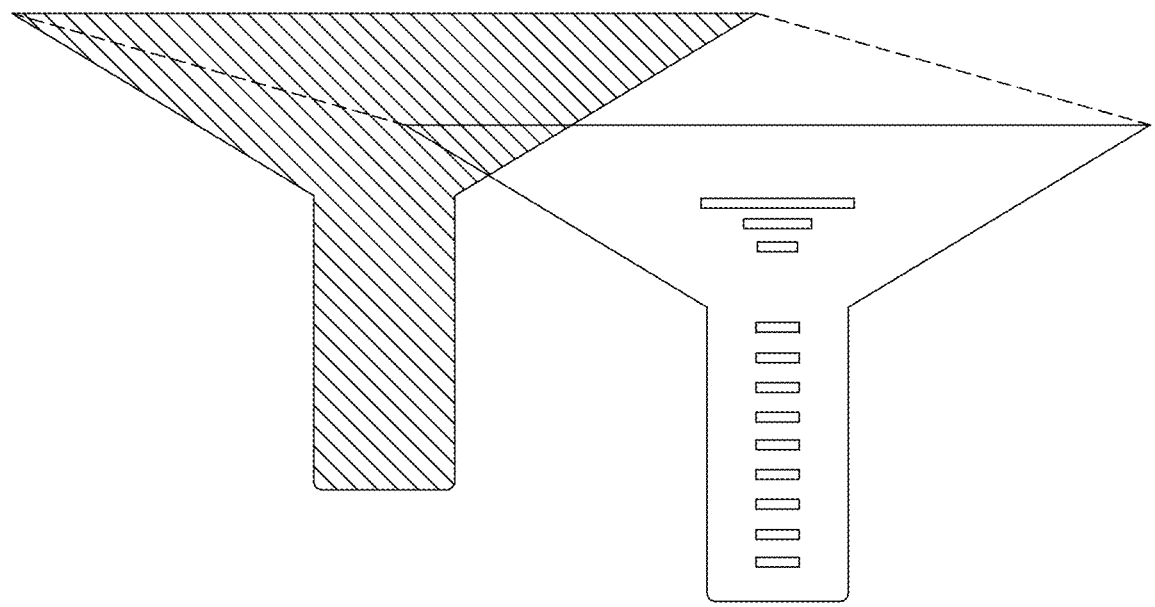

FIG. 47 shows a design for a second collection bag for a device for collecting bodily fluids from a patient during and after childbirth having a dark background on a back wall of a second collection bag and a transparent front wall of the second collection bag according to certain aspects of the present disclosure.

Figure 48:
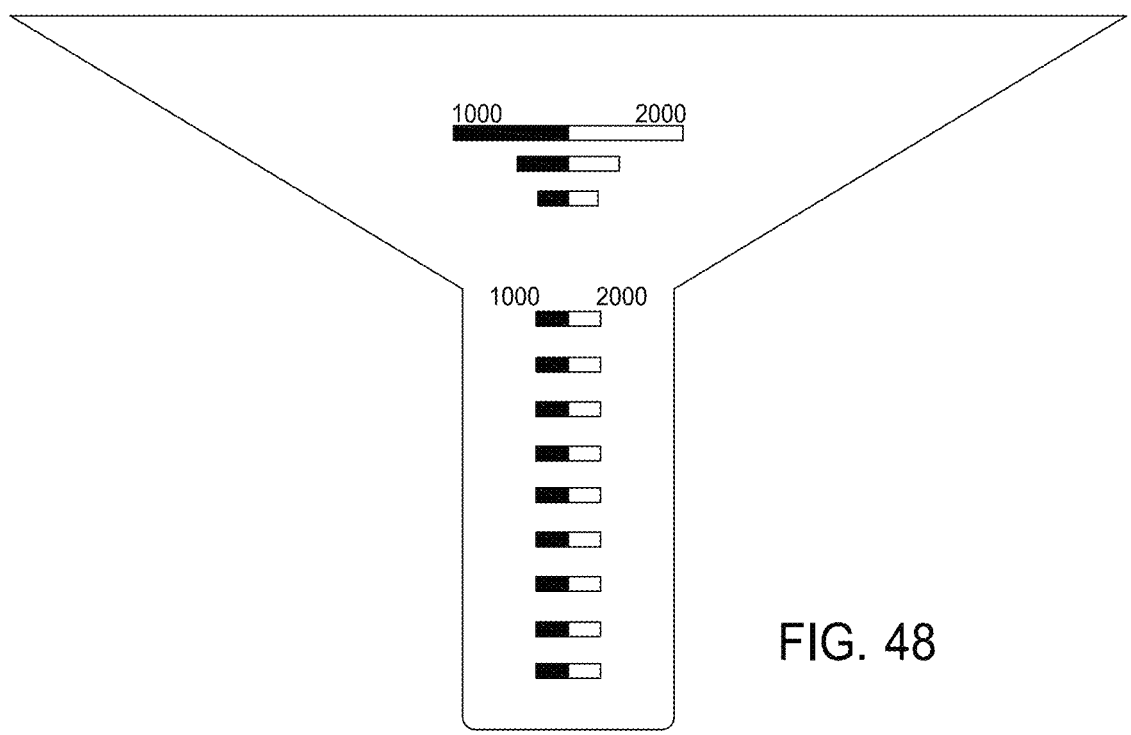

FIG. 48 shows a design for a second collection bag for a device for collecting bodily fluids from a patient during and after childbirth according to certain aspects of the present disclosure where the second collection bag has enhanced visibility by providing half of each indicia in a light color and half in a dark color.

Figure 49A:
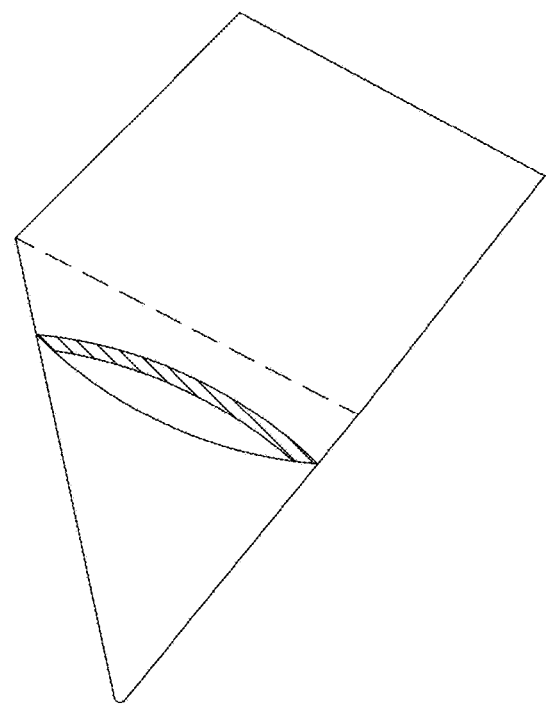
Figure 49B:
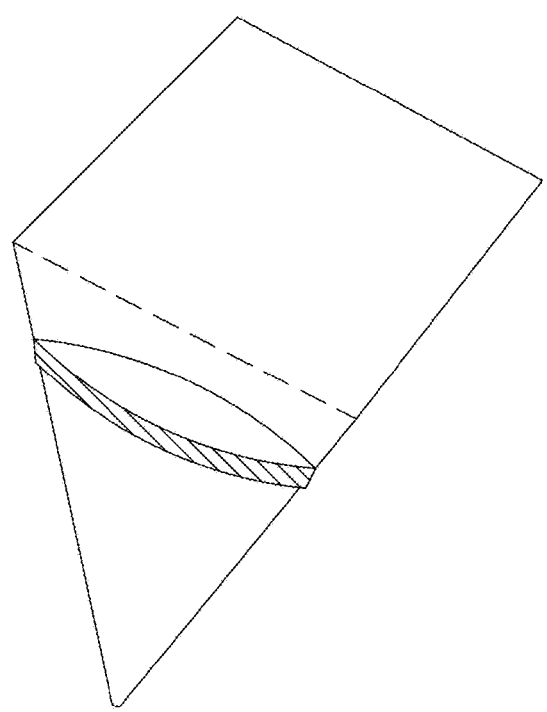
Figure 49C:
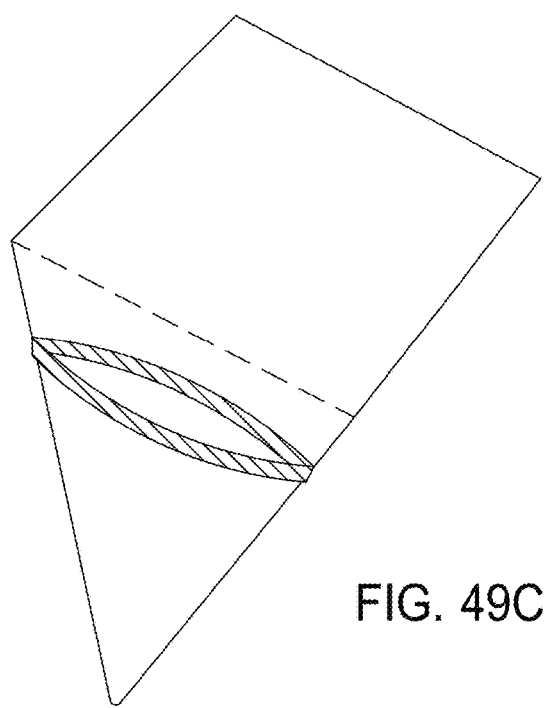

FIGS. 49A-49C show yet other variations of a device for collecting bodily fluids from a patient during and after childbirth prepared in accordance with certain aspects of the present disclosure. The first collection bag and/or the second collection bag have a closure mechanism in the form of a double-side tape that can seal each side of the upper region of the collection bag to one another and thus seal the opening closed. As shown in FIG. 49A, a double-sided tape/adhesive is provided on a back surface of the opening to the collection bag. In FIG. 49B, a double-sided tape/adhesive is provided on a front surface of the opening to the collection bag. In FIG. 49C, a double-sided tape/adhesive is provided on both a front and a back surface of the opening to the collection bag and are capable of adhering to one another to seal the opening of the collection bag.

Figure 50A:
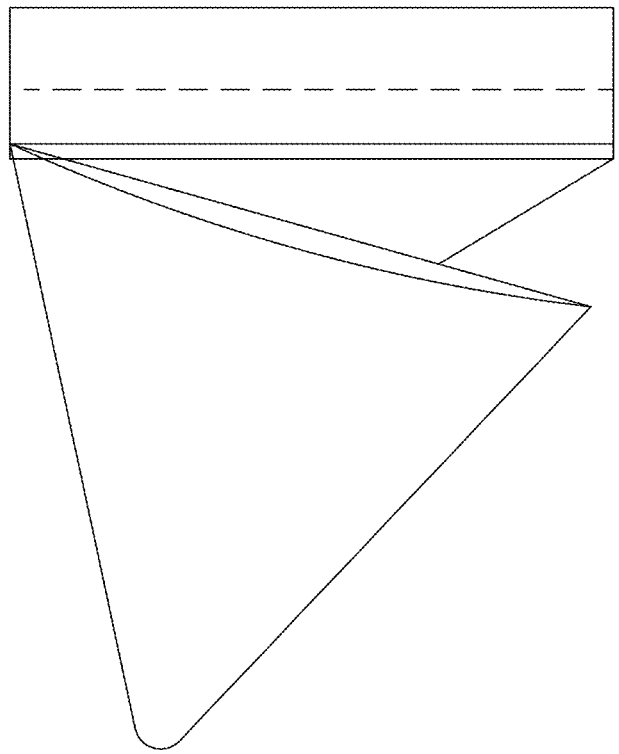
Figure 50B:
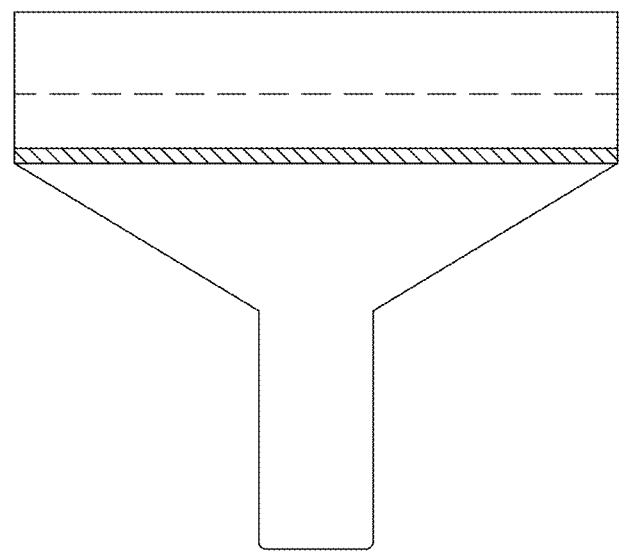
Figure 50C:
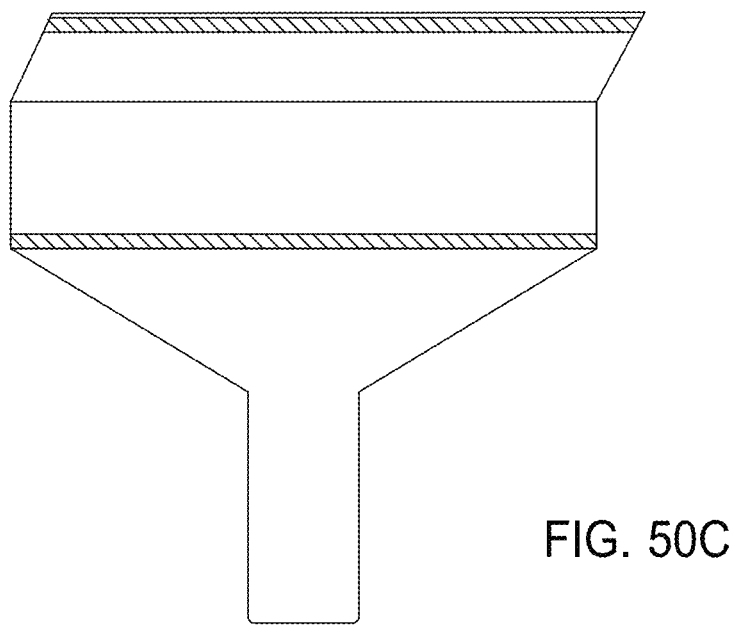
Figure 50D:
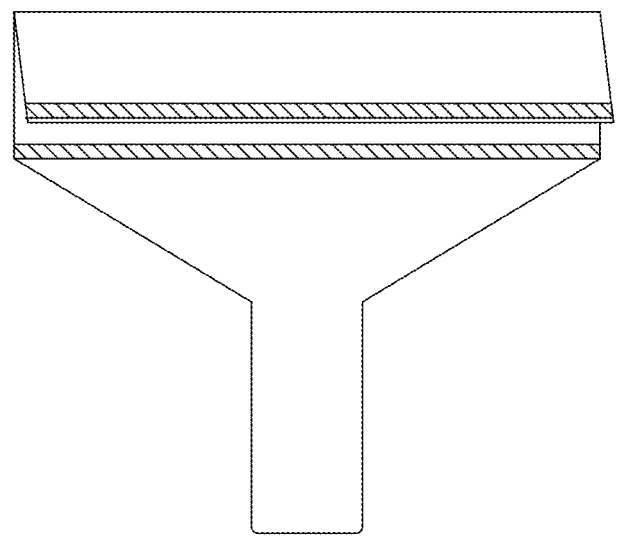

FIGS. 50A-50D show yet other variations of a device for collecting bodily fluids from a patient during and after childbirth prepared in accordance with certain aspects of the present disclosure, where a portion of polymeric material remains on the distal area of the mat device near the tongue after removing the first detachable collection bag and using the remaining portion as a cover and seal for the second collection bag. In FIG. 50A, a first collection bag is removed by tearing along a perforated region, where an extra portion of the polymeric material remains. In FIG. 50B, a closure mechanism of the second collection bag is a double-sided tape. The underside portion of polymeric material remaining in the distal region of the mat/upper region of the second collection bag is dry and has minimal or no contact with fluid as it passes into the second collection bag, so it can be lifted up to provide a dry surface as shown in FIG. 50C. Backing can be removed from the double-sided tape on the front of the opening of the second collection bag as shown in FIG. 50D, so that the double-sided tape sticks to the dry underside of the extra portion of the polymeric material and thus forms a superior seal for extra protection.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

In various aspects, the present disclosure contemplates a device for detecting postpartum hemorrhage in a patient. More specifically, the device may be a collection device, such as collection device 20 shown in FIGS. 1A-1B, 2A-2D, and 3. The device 20 may comprise a drape region or mat 30 that defines a proximal end 32 and a distal end 34. The mat 30 is configured to be disposed between a support 40 for a patient 42. The mat 30 hangs off the edge of the support 40. In FIGS. 2A-2D, the support 40 is shown to be a substantially horizontal hospital bed on which the patient sits or lies. The collection devices described herein are compatible with various hospital bed shapes and heights. As will be described further below, the mat 30 is formed of a polymer and comprises a surface 44 defining a fluid flow region 46 configured to direct flow of bodily fluids 48 from the patient 42 towards the distal end 34 of the mat 30. Use of the term bodily fluids is intended to include various substances generated by the body, including solids, semi-solids, and liquids. By way of non-limiting example, examples of bodily fluids may include amniotic fluid, blood, blood clots, tissue, urine, feces, and the like. As shown, the distal end 34 of the mat 30 extends over a terminal edge 38 of the support 40.

Figure 1A:
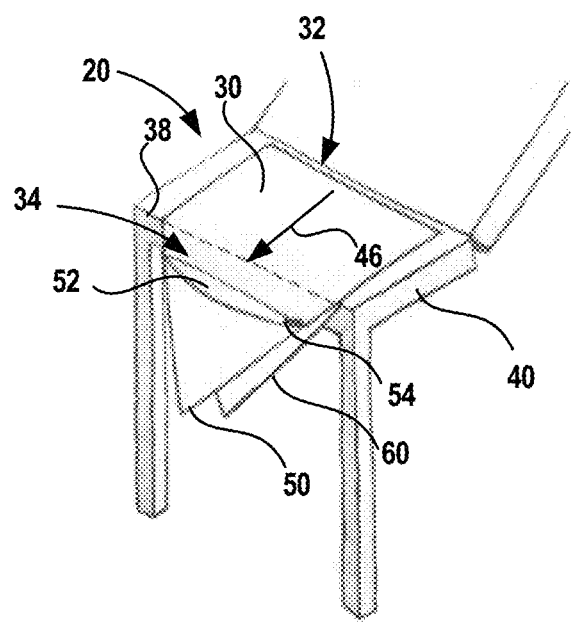
Figure 1B:
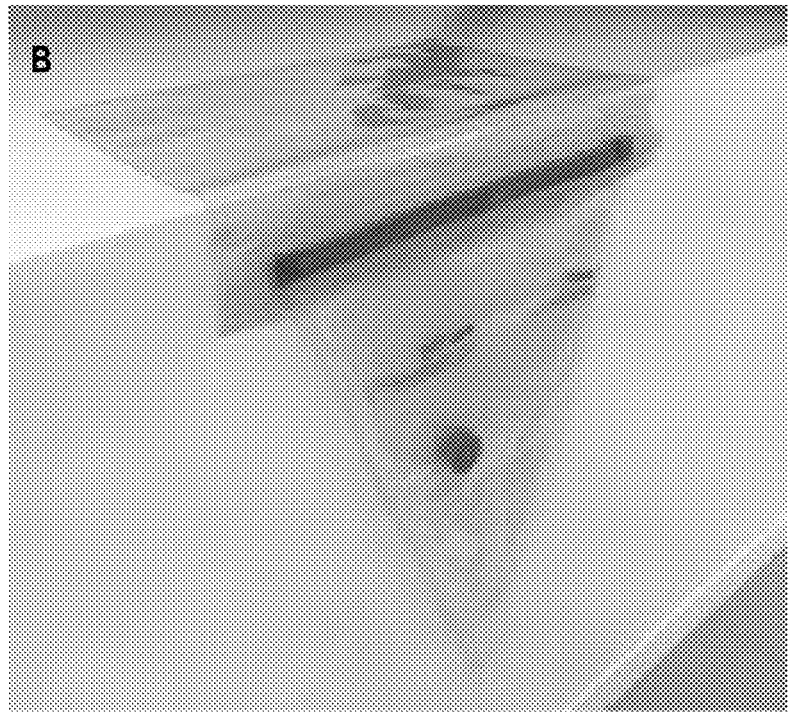

The device 20 also includes a first detachable and sealable bag 50 having a first opening 52 in fluid communication with the distal end 34 of the fluid flow region 48 and configured to receive the bodily fluids 48 from the patient 42 in a first operational mode of the device. As will be described further below, the first detachable and sealable bag 50 is formed of a polymeric material. Thus, the first detachable and sealable bag 50 may be disposable. Notably, as shown in FIG. 1B, the first detachable and sealable bag 50 may also comprise a port, for example, a suction port that can be attached to a vacuum system.

Figures 2A, 2B, 2C, 2D:
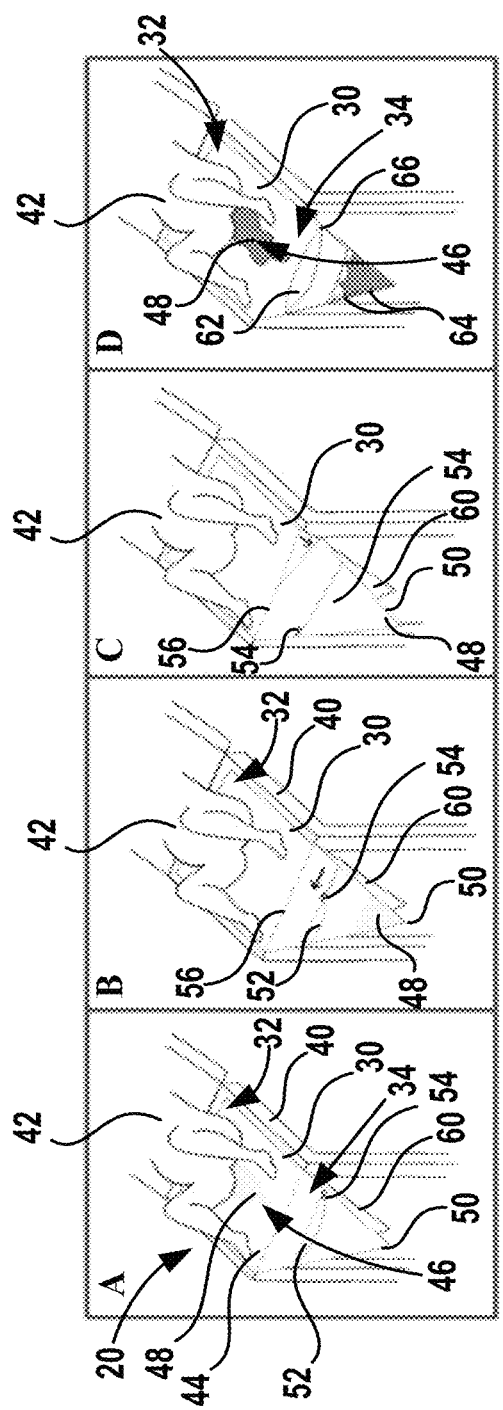
Figures 3A, 3B, 3C, 3D:
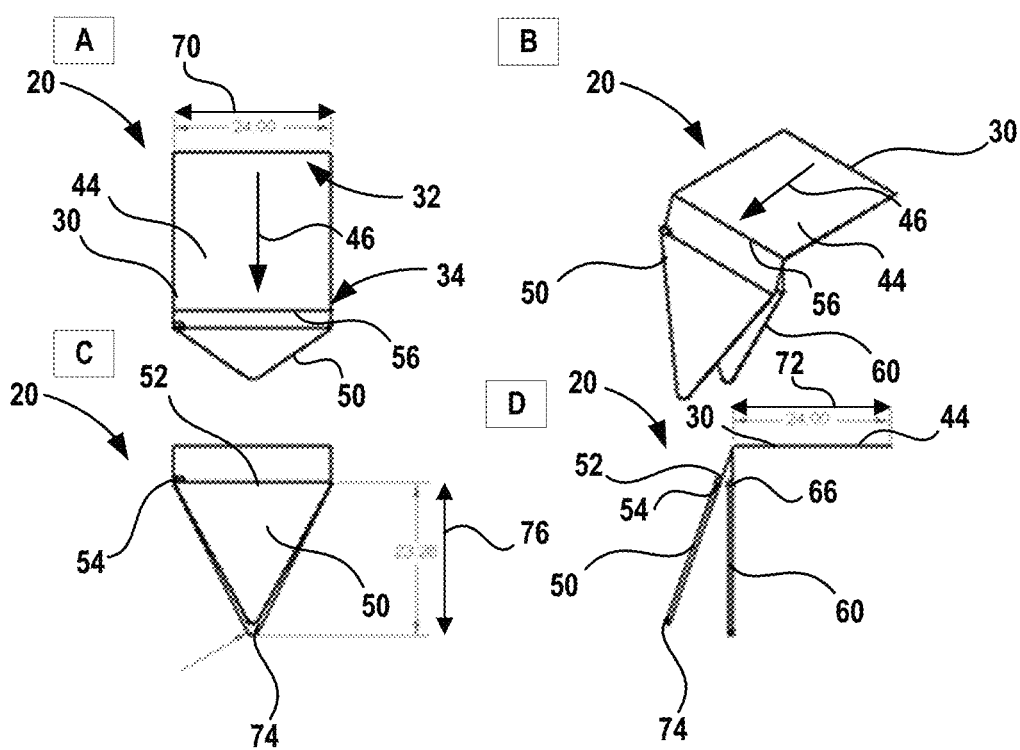

As best shown in FIGS. 2A-2B, in the first operational mode of the device 20, the first detachable and sealable bag 50 collects the bodily fluids 48 from the patient 42. The first detachable and sealable bag 50 includes a closure mechanism 54 that can seal the opening 52 and the bodily fluids within the first detachable and sealable bag 50. Suitable closure mechanisms include by way of non-limiting example, a zipper, a slide, an adhesive, or a cinching string. While not shown, the closure mechanism may further be disposed in a protective sleeve to shield it from exposure to bodily fluids. Further, the first detachable and sealable bag 50 has a weak region or tear line 56 (e.g., defined by perforations). Notably, the weak region or tear line 56 is strong enough to support the weight of each bag when filled to capacity with bodily fluids. Thus, once the first detachable and sealable bag 50 is sealed by the closure mechanism 54, the first detachable and sealable bag 50 may be removed at the tear line 56 are separated from the device 20A, as shown in FIG. 2C. The first detachable and sealable bag 50 is thus disposed over a second sealable bag 60.

The first operational mode for the device 20 generally corresponds to childbirth up to stage 2 and optionally through stage 3 where the placenta is delivered. Thus, in the first operational mode, the first detachable and sealable bag 50 collects bodily fluids 48 (e.g., delivery fluids, amniotic fluid, urine, fecal matter, disinfectant solution, tissues, and the like) during the stages of delivery prior to when the placenta is delivered. The first detachable and sealable bag 50 may be detached from the device after stage 2 of delivery, as shown in FIG. 2D. Notably, the device 20 does not interfere with or impede access to the patient during the delivery process and can be disposed under the patient before delivery, yet remain intact afterwards.

Thus, as shown in FIG. 2D, the second operational mode of device 20 begins after the baby and optionally after the placenta are delivered (transitioning to the second operational mode when delivery stages 2 and 3 are completed). The device 20 also includes the second sealable bag 60 having a second opening 62 in fluid communication with the distal end 34 of the fluid flow region 46 and configured to receive the bodily fluids 48 from the patient 42 in a second operational mode of the device 20. As will be described further below, the second sealable bag 60 is formed of a polymeric material. Thus, the second sealable bag 60 may be disposable. The second sealable bag 60 may optionally comprise a port (shown in FIG. 1B), for example, a suction port. The second sealable bag 60 may optionally be detachable from the mat 30, although in the embodiment shown it is not detachable. The second sealable bag 60 may have a visual volume indicator 64 having marked gradations to measure a volume of the bodily fluids 48 collected in the second sealable bag 60. The second sealable bag 60 also may have a closure mechanism 66. During the second operational mode of the device 20, where the second sealable bag 60 collects bodily fluids 48, the bodily fluids 48 tend to be blood and are most indicative of a potential postpartum hemorrhage. As will be described further below, a period of about 4 hours after the child is delivered is the most important period for observation of excessive blood loss from the patient to detect postpartum hemorrhage. The accurate measurement of blood loss is an important tool in order to diagnose PPH and initiate appropriate treatment, such as blood transfusions.

In this manner, the present disclosure provides a foldable, soft film obstetric device that can be disposed under the patient's buttocks. The device has a bifold two-compartment or bag collection mechanism, which are attached to the drape or mat and that provide the capability of separating blood from pre-delivery and delivery fluids by using temporal relationship of vaginal delivery. Thus, the device provides a first operational mode and a second operational mode, where blood loss is measured in the second sealable bag 60 during the second operational mode. The second sealable bag 60 with marked volume gradations collects and quantifies hemorrhaging blood accurately after the placenta is delivered.

FIGS. 3A-3D shows representative and non-limiting dimensions of one embodiment of a device 20, which may be formed of thermoplastic polyurethane (TPU), by way of example. The mat may have a width 70 of about 24 inches and a length 72 of about 24 inches. The first detachable and sealable bag 50 and/or the second sealable bag 60 may have a collection portion (e.g., from opening 52 to a terminal end 74 of the bag 50) with a length 76 between about 23 and 24 inches.

A collection device like 20 shown in FIGS. 1A-1B, 2A-2D, and 3 can assist medical care providers in accurately measuring blood loss of postpartum patients. As noted above, the design includes a drape or mat portion attached to two flexible plastic collection bags, with one laying on top of the other. One bag is for the collection of pre-delivery fluids (amniotic fluid, urine, fecal matter, and disinfectant solution) and one is for the collection of blood. Once the baby is delivered, the first bag can be sealed and torn away, allowing largely blood product to collect in the second bag.

In various aspects, the collection device provided by various aspects of the present disclosure provides one or more of the following advantages. The device allows the user (e.g., healthcare provider) to distinguish hemorrhage blood from other fluids and objects during delivery, provides for accurate quantification of the hemorrhage blood that is easily visualized, does not impose a greater burden on clinical staff than current processes, directs all fluids from the patient to the fluid collection portions of the device, robustly contains the fluids, does not obstruct access to the vaginal area and abdomen throughout labor, delivery, and recovery, in other words, does not infringe on care of the patient, is formed of a material compatible with patient skin, fluid, and cleaning solutions, is comfortable and widely accommodates women of different sizes (e.g., 95% of women), is sterile and hygienic, is inexpensive, and is easy to store under a variety of environmental conditions. In certain variations, the entire device may be disposable.

As noted above, the device prepared in accordance with certain aspects of the present disclosure provides the ability to distinguish blood from other fluids involved in labor, such as amniotic fluid, urine, feces, and cleaning products, like savlon. Thus, it is desirable that about 97.5% of the total postpartum blood lost is separated from any other fluids collected. This number was defined based on the maximum blood typically lost by a woman during labor, which is about 2 L. If 97.5% of this maximum value is captured, then the reading will be within ±50 mL of the true amount of blood loss, which provides accurate measurement. Capturing≥about 97.5% of the blood lost would also minimize uncontrolled spillage of blood, thus alleviating the cleaning process for midwives and patients and prevent contamination of the beds and floors. The devices provided by certain aspects of the present disclosure are capable of providing accuracy of measurements within +50 mL of the true amount of blood loss from the patient. In certain aspects, the first detachable and sealable bag has a first volumetric capacity, while the second sealable bag has a second volumetric capacity. The first volumetric capacity may be the same as or different from the second volumetric capacity. In certain variations, the first volumetric capacity and the second volumetric capacity are the same, which may be less than or equal to about 2,000 mL (or each first volumetric capacity and the second volumetric capacity may be about 1,000 mL). In certain variations, a total capacity of the device, including the first volumetric capacity and the second volumetric capacity may be less than or equal to about 1,000 mL (or each first volumetric capacity and the second volumetric capacity may be about 500 mL).

In certain aspects, the second bag has a minimum volumetric unit of 50 mL, optionally about 100 mL, and in certain variations, 200 mL. While various gradations of volume may be used for the visual volume indicator on the second bag, in certain variations, the second bag has a minimum volumetric unit of 250 mL. Empirical testing indicates that graduations every 250 mL is optimal to increase interpretability of the measurements of volume. Furthermore, differences of 250 mL can be more significant for health care providers for PPH treatment than lover volumetric measurements. In certain other variations, the second bag may have a minimum volumetric unit of 500 mL.

In certain aspects, the first detachable and sealable bag has a first shape and the second sealable bag has a second shape. The first shape and the second shape may be the same. In one variation, like that shown in FIGS. 1A-1B, the first shape and the second shape are a triangle and more specifically, an isosceles triangle. In another variation like that shown in FIG. 4, the first shape and the second shape are a trapezoid, for example, an isosceles trapezoid. In other variations, the first shape and the second shape may differ from one another, as will be described in greater detail below.

Figures 4A, 4B, 4C:
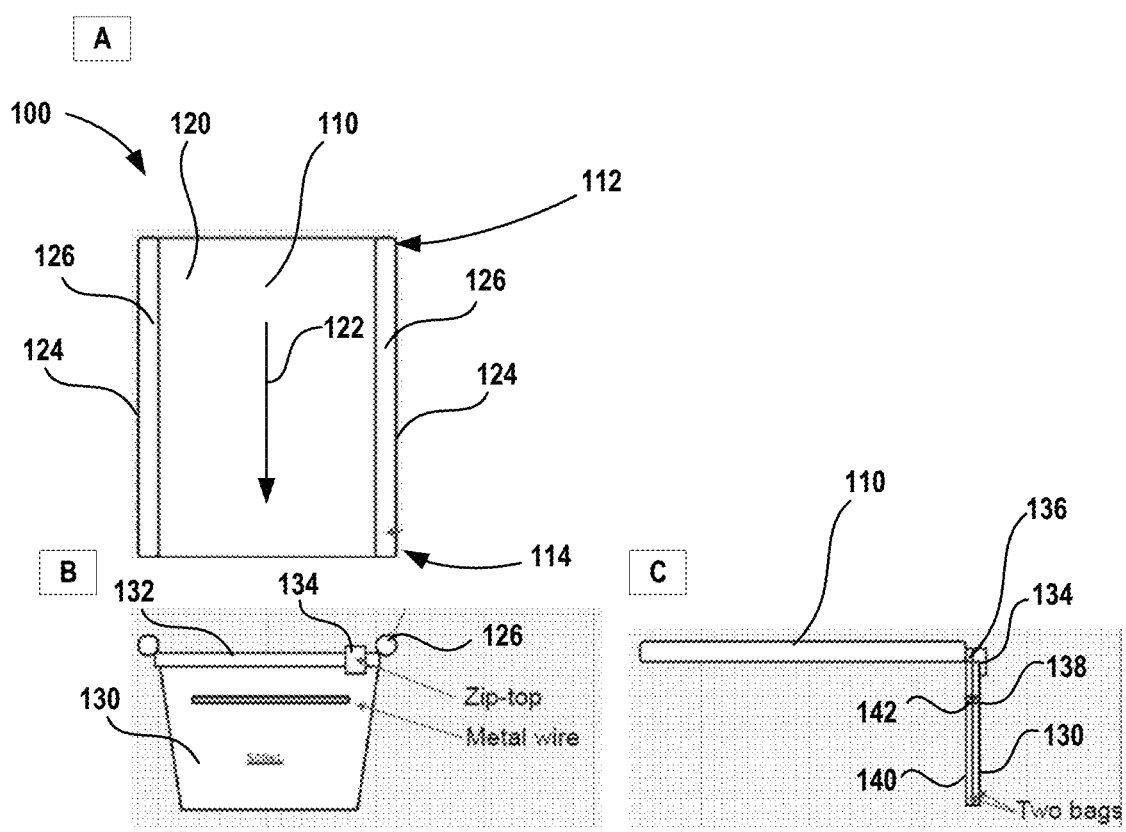

FIGS. 4A-4C show a device 100 for collecting bodily fluids from a patient to detect postpartum hemorrhage after delivery of a child. The device 100 may comprise a drape region or mat 110 that defines a proximal end 112 and a distal end 114. The mat 100 has a surface 120 defining a fluid flow region 122 configured to direct flow of bodily fluids from a patient 42 towards the distal end 114 of the mat 110. As shown, the mat 110 has two peripheral edges 124 with raised edges 126. In this manner, the raised edges 126 help to define the fluid flow region 122 on surface 120 of the mat 110.

The device 100 also includes a first detachable and sealable bag 130 and a second sealable bag 140 disposed beneath the first detachable and sealable bag 130. Notably, the first detachable and sealable bag 130 and second sealable bag 140 have an isosceles trapezoidal shape. A first opening 132 in fluid communication with the distal end 114 of the fluid flow region 122 is configured to receive the bodily fluids from the patient in a first operational mode of the device 100. The first detachable and sealable bag 130 includes a closure mechanism 134 shown in the form of a zip top that can seal the first opening 132 to seal bodily fluids within the first detachable and sealable bag 130. Further, the first detachable and sealable bag 130 may have a tear line (e.g., defined by perforations) or other release mechanism 136 so that it can be removed from the device 100.

After removal of the first detachable and sealable bag 130, the device 100 is then in a second operational mode, where the second sealable bag 140 is collecting bodily fluids excreted from the patient that move from the fluid flow region 122 on surface 120 of the mat 110. Thus, the second sealable bag 140 is in fluid communication with the distal end 114 of the fluid flow region 122 and configured to receive the bodily fluids from the patient in a second operational mode of the device 100. The second sealable bag 140 may have features like those previously described in the context of the second sealable bag 60 in FIGS. 1A-1B and 2A-2D, which for brevity will not be repeated herein.

Notably, in the design of the first detachable and sealable bag 130 and the second sealable bag 140 shown in FIG. 4, each of the bags includes a first reinforcement member 138 or second reinforcement component 142. The first reinforcement member 138 or second reinforcement component 142 may be an internally disposed wire or other rigid member that helps to retain a shape and maintain patency of the first opening 132 and/or the second opening (not shown). Because the bags are attached tautly to the mat, in certain embodiments, it can be difficult to hold open the openings or at least open them widely. To address this, the first reinforcement member 138 or second reinforcement component 142 in the form of a wire can be used around the rim of the bag's opening to hold it open.

With regard to the shape of each bag, it should be noted that in certain contexts, it may be more difficult to observe volume changes when the shape of the bag is a triangle so that a conical shape is formed when the fluid fills the bag. For a conical shape, a difference in fluid height between the 200 mL gradation and the 500 mL gradation is much more significant than the difference in height between the 500 mL gradation and the 1000 mL gradation with the conical shape. This could decrease clarity of the fluid loss and potentially be misleading in ascertaining accurate blood loss measurement values quickly. However, a trapezoidal shape for the first detachable and sealable bag 130 and the second sealable bag 140, as shown in FIG. 4 can address this issue. The shape of the collection bags can be a straight bottom or terminal edge rather than a tip. With such a collection bag design, the trapezoidal shape exhibits decreased differences in heights for volumetric measurements as compared to the triangular or conical bag design design.

As shown in FIGS. 5A-5F, a device for collecting bodily fluids from a patient during and after childbirth prepared in accordance with certain aspects of the present disclosure may have a variety of distinct mat portion shapes or sizes. In certain variations that will be described further herein, the mat has a shape selected from a rectangle, a trapezoid, or a hemisphere. For example, in FIG. 5A, a first device 150 may include a mat portion 152 having a rectangular shape and a collection bag 154 (only one of two shown in FIGS. 5A-5F) having a representative and non-limiting triangular shape. The mat portion 152 has a first width 156 that is the same as a second width 158 of the collection bag 154.

Figures 5A, 5B, 5C, 5D, 5E, 5F:
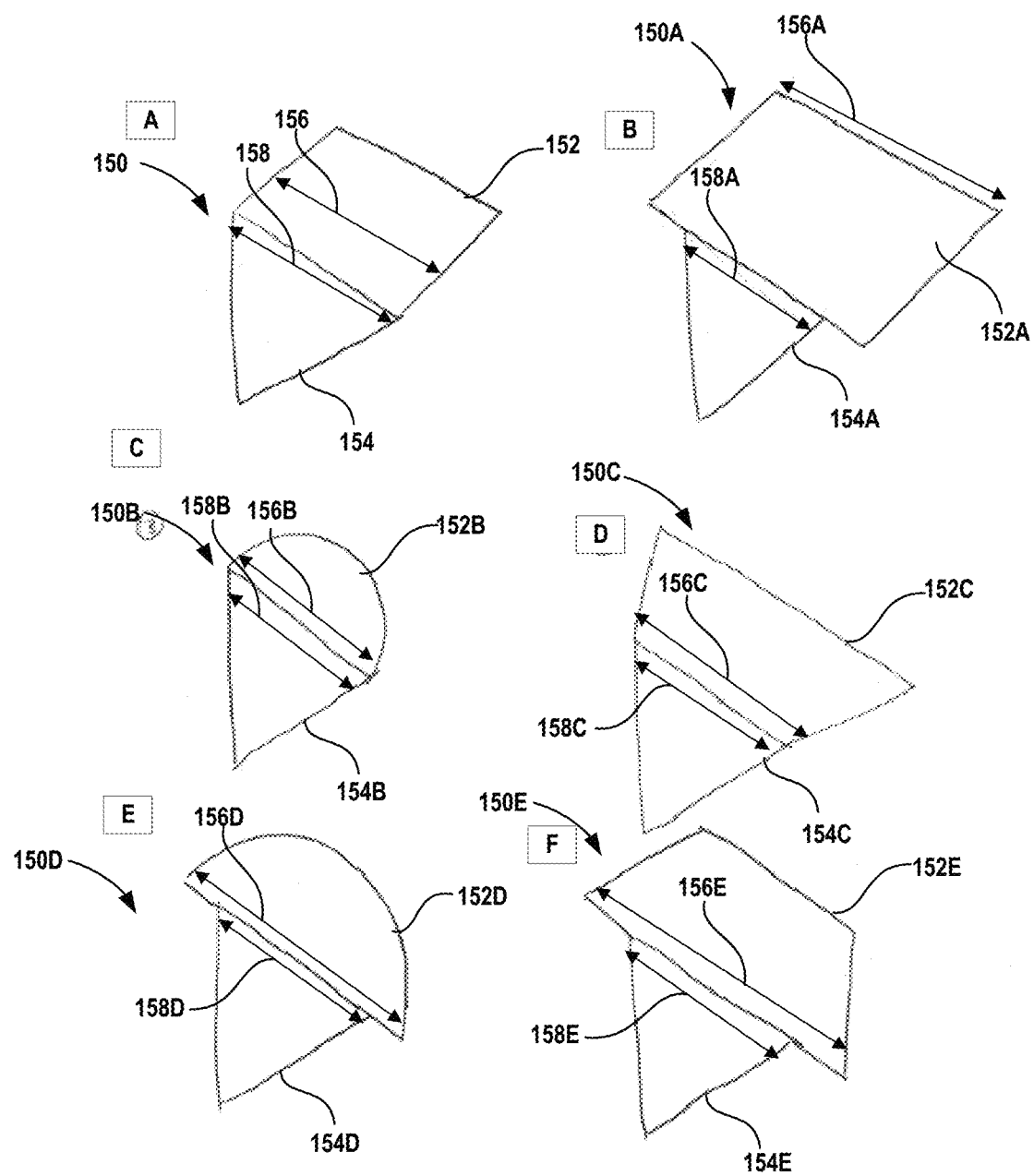
FIGS. 5A-5F are illustrations of various representative examples of devices for collecting bodily fluids from a patient during and after childbirth prepared in accordance with certain aspects of the present disclosure, where a mat portion may have different sizes or shapes.

Another device 150A in FIG. 5B may include a mat portion 152A having a rectangular shape and a collection bag 154A (only one of two shown) having a representative and non-limiting triangular shape. The mat portion 152A has a first width 156A that is larger than a second width 158A of the collection bag 154A. Notably, this larger mat portion 152A many provide the capability for the mat to be at least partially wrapped or adhered to the underlying support surface.

Yet another device 150B in FIG. 5C may include a mat portion 152B having a hemispherical shape and a collection bag 154B (only one of two shown) having a representative and non-limiting triangular shape. The mat portion 152B has a first width 156B that is the same as a second width 158B of the collection bag 154B.

Device 150C in FIG. 5D may include a mat portion 152C having a trapezoidal shape and a collection bag 154C (only one of two shown) having a representative and non-limiting triangular shape. The mat portion 152C has a first width 156C that is the same as a second width 158C of the collection bag 154C.

Yet another device 150D in FIG. 5E may include a mat portion 152D having a hemispherical shape and a collection bag 154D (only one of two shown) having a representative and non-limiting triangular shape. The mat portion 152D has a first width 156D that is greater than a second width 158D of the collection bag 154D.

Finally, device 150E in FIG. 5F may include a mat portion 152E having a trapezoidal shape and a collection bag 154E (only one of two shown) having a representative and non-limiting triangular shape. The mat portion 152E has a first width 156E that is greater than a second width 158E of the collection bag 154E.

As described above, to assist with defining a flow field region on a surface of the mat portion of the device, the polymeric mat defines two peripheral edges that may have a protruding feature or a channel feature configured to prevent egress of bodily fluids beyond the two peripheral edges. Thus, in certain aspects, the feature at the peripheral edge may be selected from one of a bumper, such as an inflatable bumper or a solid material, a raised portion or ridge, a roll (for example, rolled material forming the mat), or a groove or channel. By way of example, the edges of the mat flanking the patient's body can be rolled to act as a barrier to prevent fluid from spilling off the side or peripherals edges of the mat. In one example, a two-inch portion of the sides of the mat can be rolled to form the rolled edge portions.

In certain other variations, a device 200 for collecting bodily fluids from a patient during and after childbirth prepared in accordance with certain aspects of the present disclosure may have a fastener 202 to couple a polymeric mat 204 to the support (as shown in FIGS. 1A and 2A-2D). In certain aspects, the fastener 202 may be a belt or a strap that extends around a circumference of the support and may be mechanically secured.

Figure 7C:
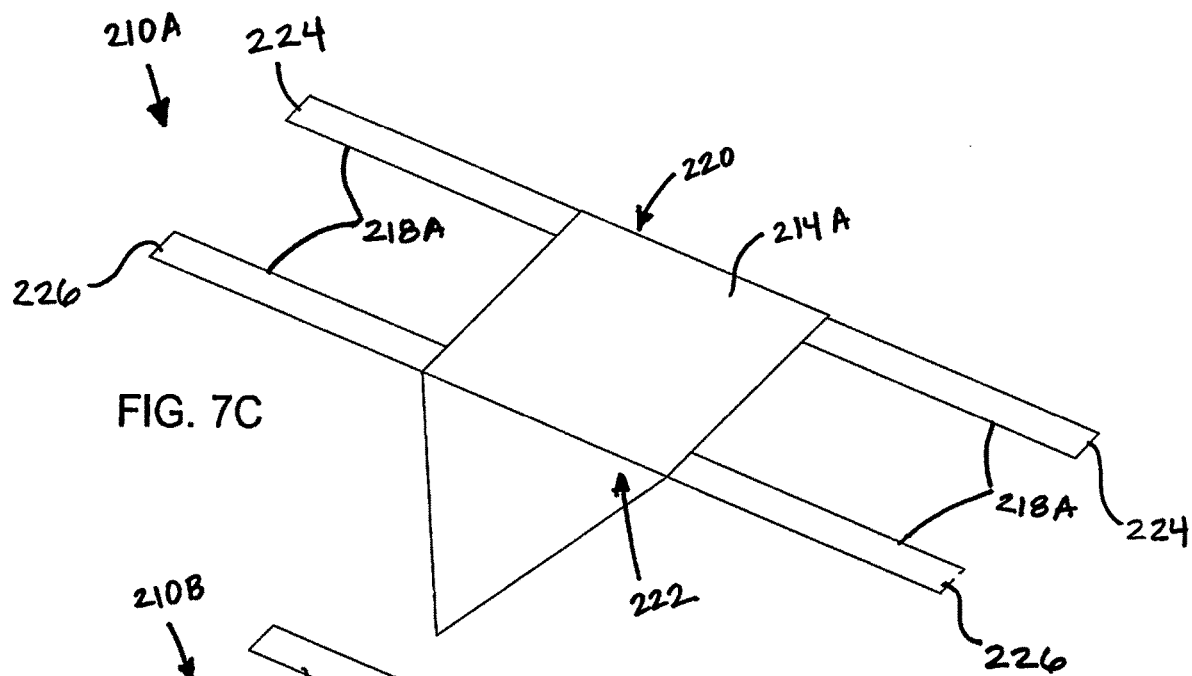
Figure 7D:
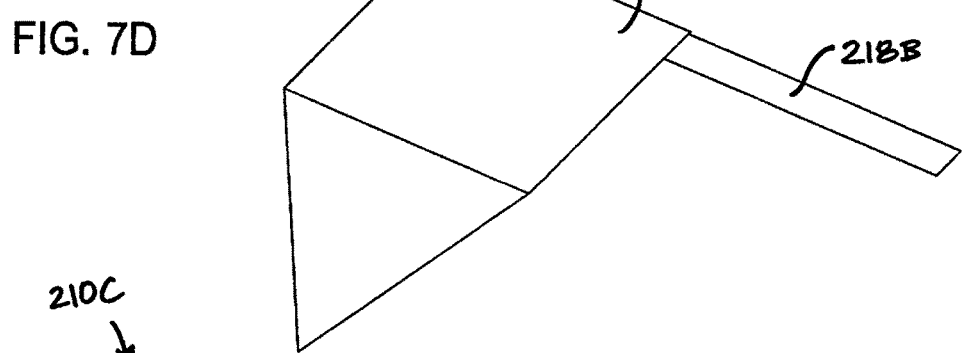
Figure 7E:
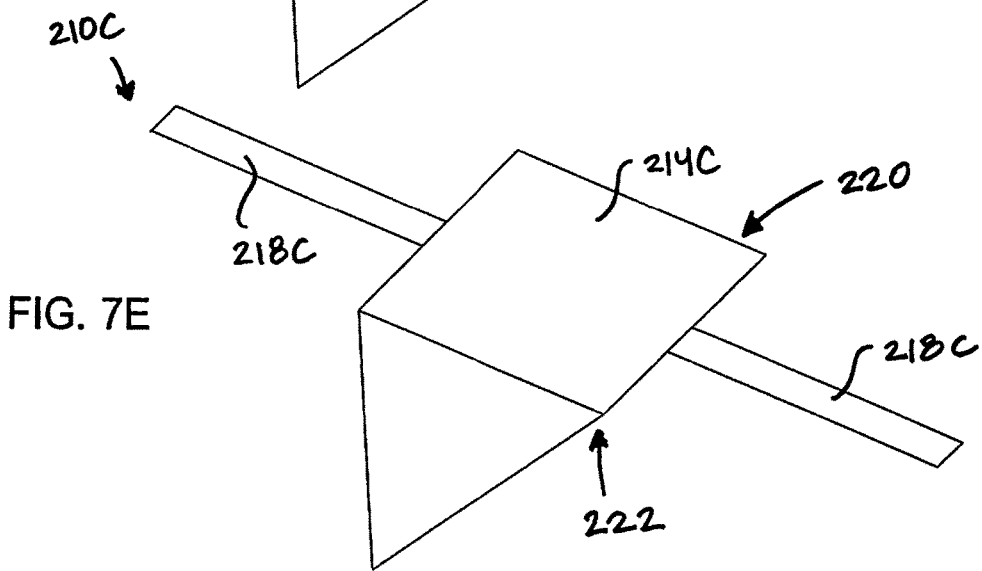

In alternative variations, a device for collecting bodily fluids from a patient during and after childbirth prepared in accordance with certain aspects of the present disclosure may have a fastener to couple the polymeric mat to the patient. FIGS. 7A-7B show such a device 210 where peripheral edge regions 212 of a mat portion 214 of are perforated along perforation lines 216 and may be torn to create straps 218 that can be tied and secured around the support structure or a patient. Thus, the device 210 includes at least two straps 218 as fasteners. The location, number of strips, material, length and width of the strips 218 may be varied. For example, as shown in device 210A in FIG. 7C, there are four straps 218A, including a first pair 224 of straps at a proximal end 220 and a second pair of straps 226 at a distal end 222 of the mat 214A. Another device 210B in FIG. 7D has two straps 218B forming a single pair of straps at the proximal end 222 of mat 214B. Another embodiment of device 210C is shown in FIG. 7E having a single pair of two straps 218C attached at a mid-point of the mat 214C disposed between the proximal end 220 and the distal end 222.

Figure 8:
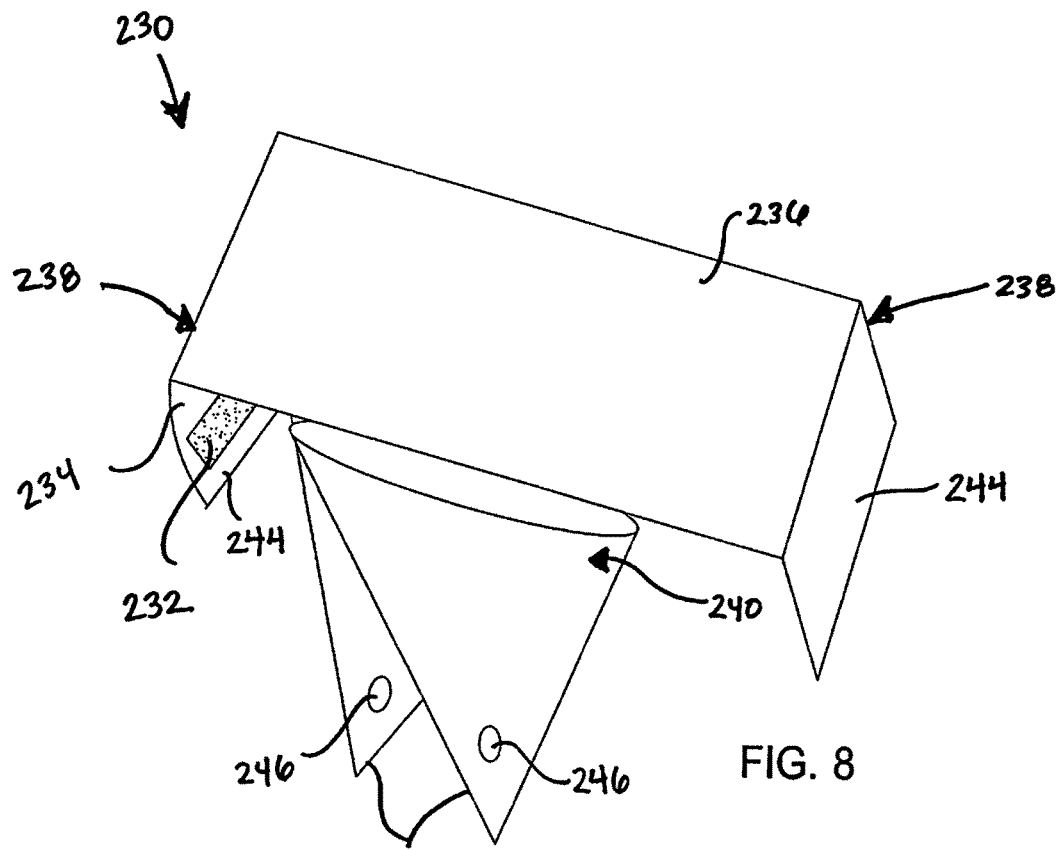
FIG. 8 is an illustration of a device for collecting bodily fluids from a patient during and after childbirth prepared in accordance with certain aspects of the present disclosure that includes an adhesive on peripheral sides of a mat that can adhere to a surface of a support and mechanically secure the device to the support structure.

In other aspects, the fastener may be an adhesive that adheres to a surface of the support, such as that shown in device 230 in FIG. 8. One or more adhesive strips 232 may be disposed on a bottom surface 234 of a mat portion 236 along peripheral edge regions 238 so that it adheres to an underlying support structure (not shown in FIG. 8). The adhesive need not be an entire strip, but rather may also be applied in discrete regions to establish sufficient contact with the underlying support structure, for example, at corners of the peripheral edge regions 238 of the mat. This is particularly suitable for mat designs where a width of the mat 236 is greater than a width of an upper region 240 of collection bags 242. Suitable non-limiting examples of adhesives for the strips 232 include acrylics, posies, silicones, styrene block copolymers, pressure sensitive adhesives (PSAs), and the like. Thus, in FIG. 8, the mat 236 defines two peripheral edges 244 that each extend over lateral edges of the support (not shown). Notably, in FIG. 8, the device 230 also includes two collection bags 242 each with a port 246 to connect to external suction or vacuum (not shown). Other suitable fasteners include by way of non-limiting example, buttons to couple to a surface of the support (where the support may have a slot or button and the mat has the other of the slot or button), magnets to couple to a surface of the support (where the mat portion has a magnet with a first polarity and the support has a magnet with an opposite polarity), a hook and eye material (VELCRO® straps) on the bottom surface of the mat portion to couple to a surface of the support to the mat portion, a snap having mating pieces on the mat and surface of the support to couple to a surface of the support, sticky putty and the like.

In certain variations, each of the first detachable and sealable bag, the second sealable bag, and the polymeric mat may be independently formed of a polymer selected from the group consisting of: polypropylene, polyethylene, polyetheretherketone (PEEK), polyvinylchloride (PVC), polyurethane (PU), metallocene catalyzed thermoplastic polymers, siloxane, elastomers, shape memory elastomers, and combinations thereof. Examples of types of polymeric materials thus include PEEK/PVC/PP/PU, thermoplastics, metallocene catalyzed thermoplastics, formed silicone or urethane, shape memory elastomer, thermoplastic elastomer, thermoset elastomer, thermoplastic urethane (TPU), and VersiFlex™ PVC.

As noted above, in certain variations, the first detachable and sealable bag is disposable and the second sealable bag may also be disposable. In other variations, the second sealable bag may be permanently affixed to the device, while the first detachable bag is either reusable or disposable. Notably, the first detachable and sealable bag and the second sealable bag may be formed of the same material or of different polymeric materials. In certain variations, the plastic used may have a thickness of less than or equal to about 0.020 inches.

In certain variations, the mat may be reusable and the first detachable and sealable bag and the second sealable bag comprises at least one connector to reversibly couple and physically connect the first and second bags with the mat. Notably, the at least one connector is strong enough to support the weight of each bag when it is filled to capacity with bodily liquids.

Figure 9:
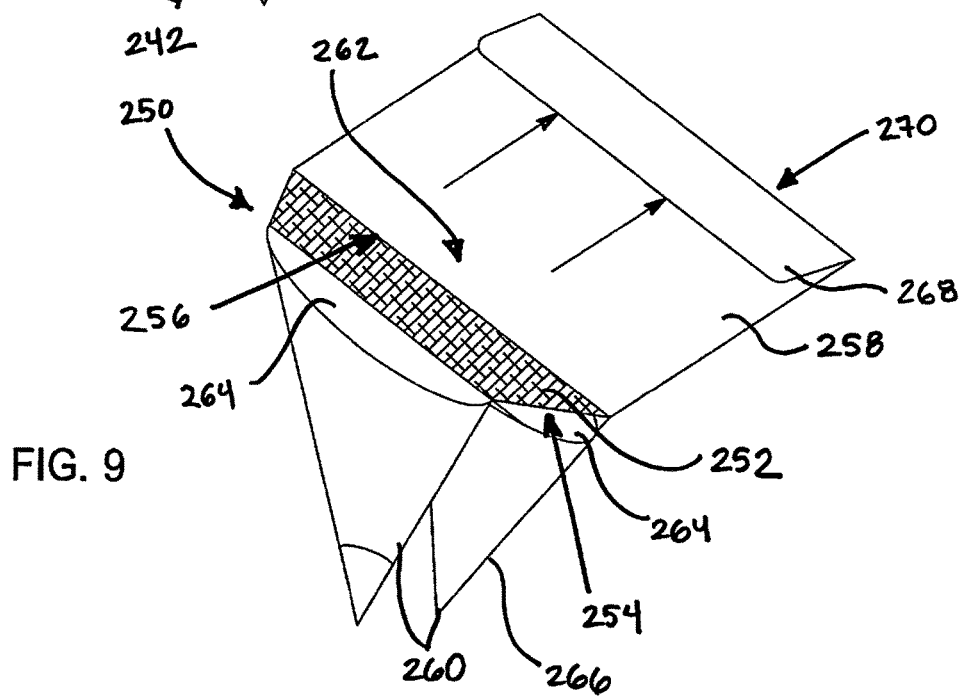
FIG. 9 is an illustration of another variation of a device for collecting bodily fluids from a patient during and after childbirth prepared in accordance with certain aspects of the present disclosure that has a filter for filtering materials generated by the body in a distal end of a mat.

In yet other embodiments like that shown in FIG. 9, a device 250 for collecting bodily fluids from a patient during and after childbirth prepared in accordance with certain aspects of the present disclosure may have a filter 252 in a tongue region 254 at a distal end 252 of a mat 258 as shown in FIG. 9, or alternatively, the filter 252 may be disposed in one or more of the first and second collection bags 260 (not shown). The filter 252 in FIG. 9 is in the tongue region 254 between a flow field region 262 of the distal end 256 of the mat 258 and openings 264 in the first and second collection bags 260. In this manner, the filter 252 may advantageously filter bodily substances, such as the debris and bodily fluids, so only blood, blood clots, or desired substances are collected in a second collection bag 266. Notably, in FIG. 9, either of the first collection bag and/or second collection bag 260 optionally has a blood thinner for any clots. By way of example, the collection bag(s) 260 may include an anti-coagulant coating on at least one surface, such as ethylenediaminetetraacetic acid (EDTA) used to break up clots. The device 250 in FIG. 9 further includes a flap or folded region 268 in a proximal end 270 of the mat portion 258. The flap or folded region 268 is configured for a user to use hands to tuck the device 250 under the patient.

Figure 10:
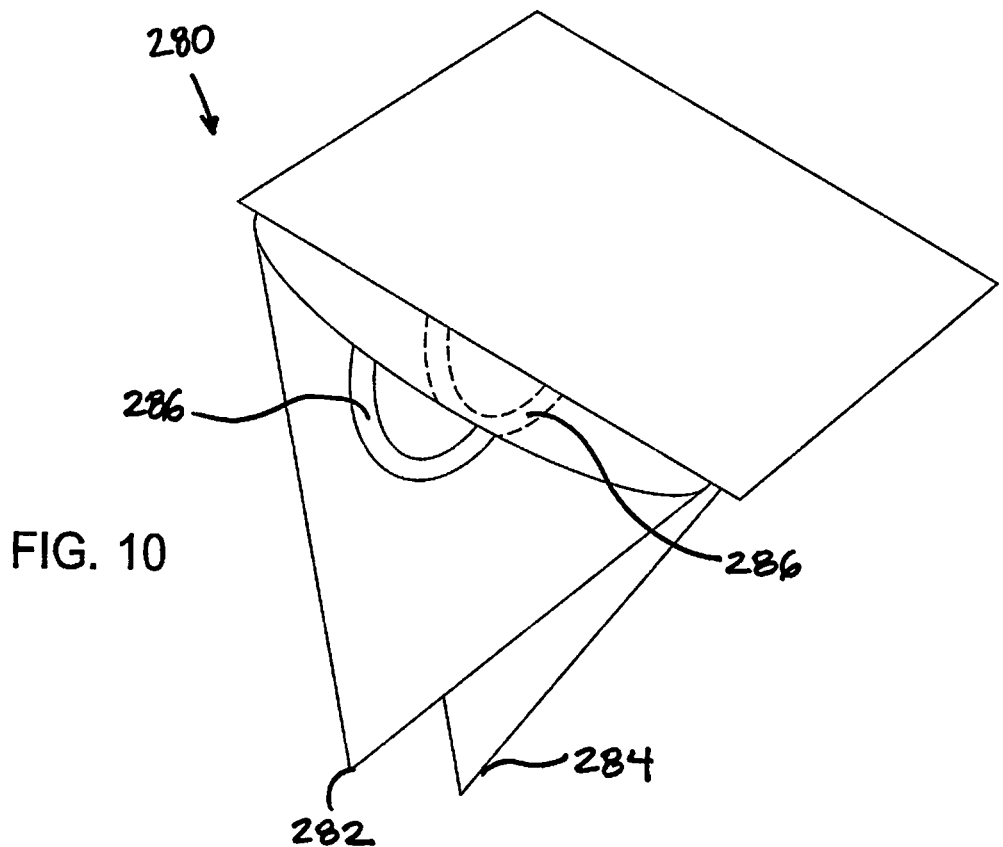
FIG. 10 is an illustration of another variation of a device for collecting bodily fluids from a patient during and after childbirth prepared in accordance with certain aspects of the present disclosure where each of a first detachable and sealable bag and a second sealable bag comprises a handle to facilitate removal of each bag after it has been sealed and will be removed.

A device 280 shown in FIG. 10 for collecting bodily fluids from a patient during and after childbirth prepared in accordance with certain aspects of the present disclosure may have a first detachable and sealable bag 282 and a second sealable bag 284 that each comprise a handle 286 to facilitate removal of each bag after it has been sealed and will be removed.

Figure 11A:
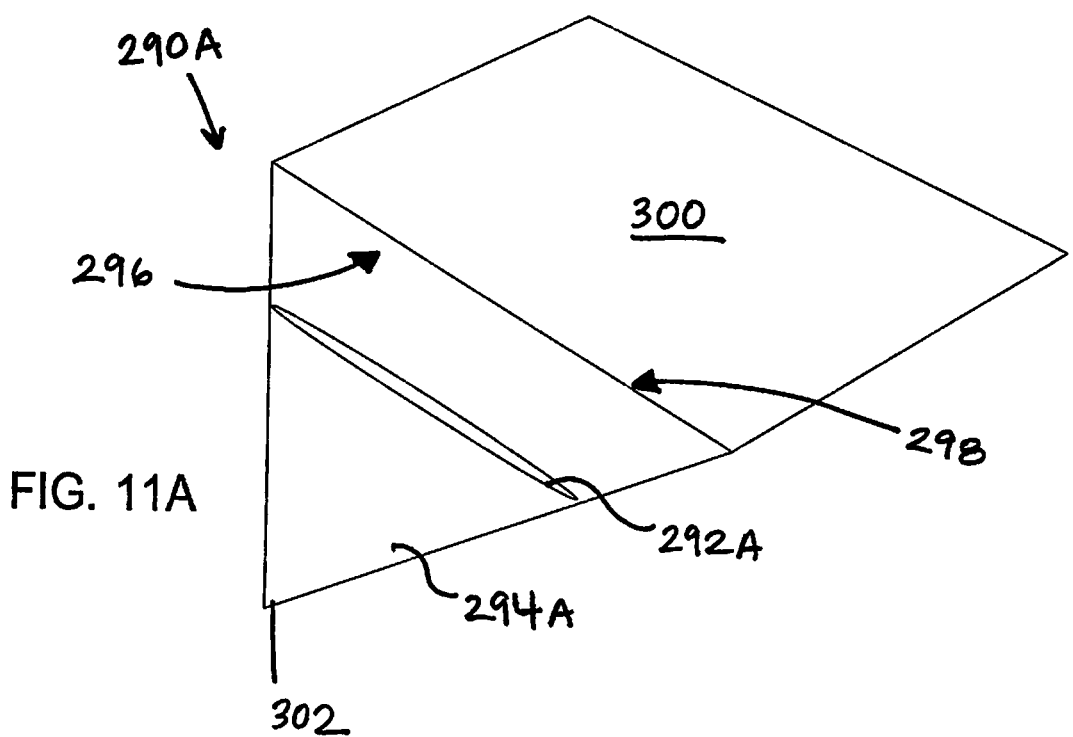
FIGS. 11A-11H are illustrations of various representative examples of devices for collecting bodily fluids from a patient during and after childbirth prepared in accordance with certain aspects of the present disclosure, showing different placement and sizes of openings in collection bags.
Figure 11B:
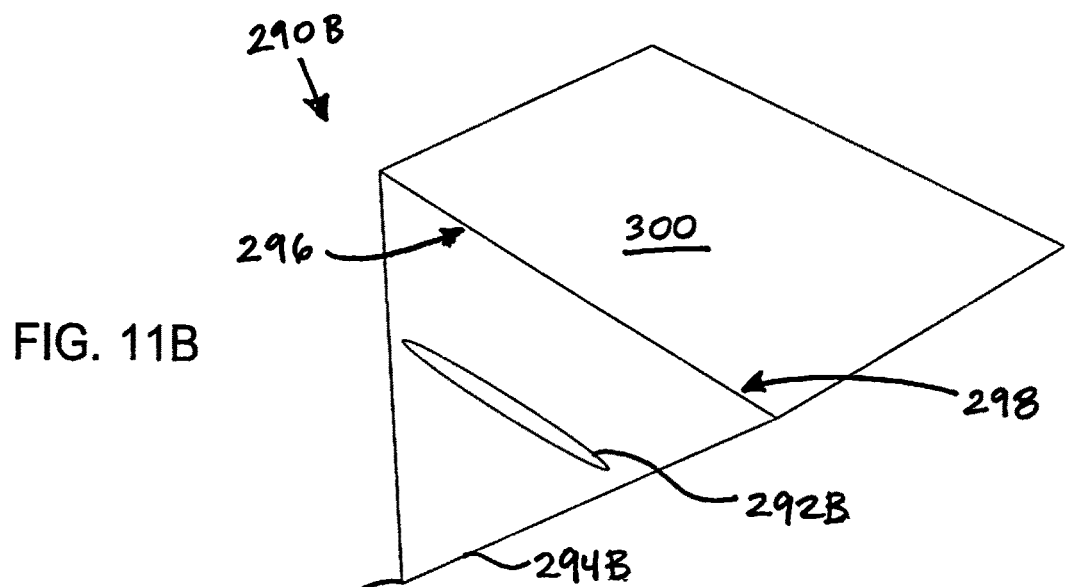
Figure 11C:
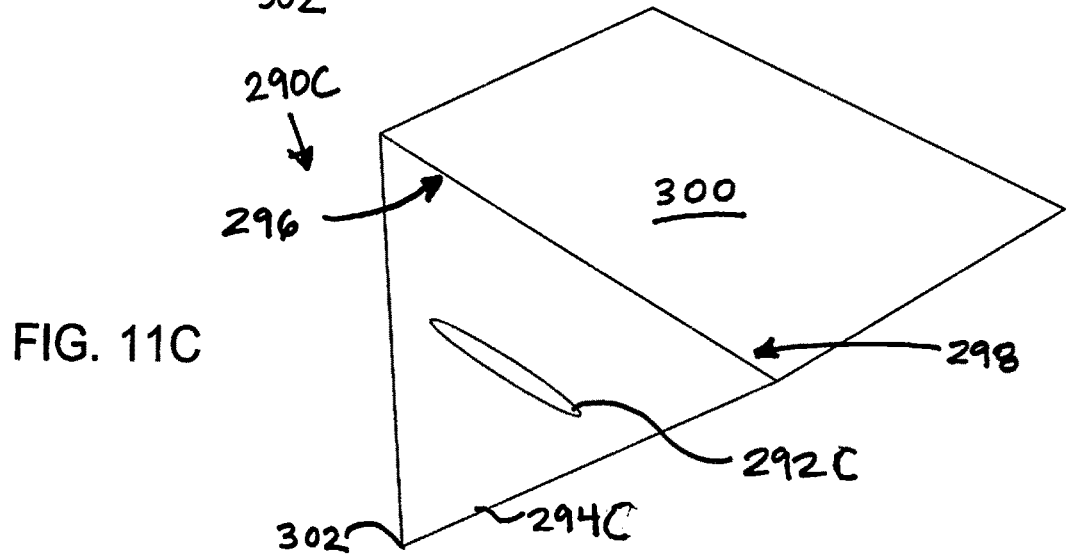
Figure 11D:
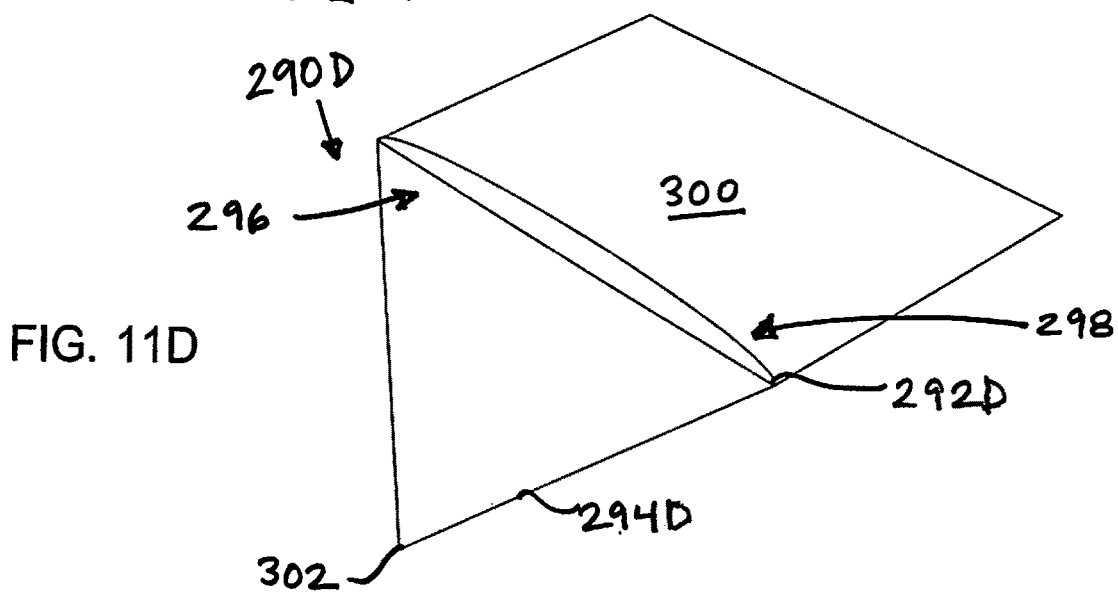
Figure 11E:
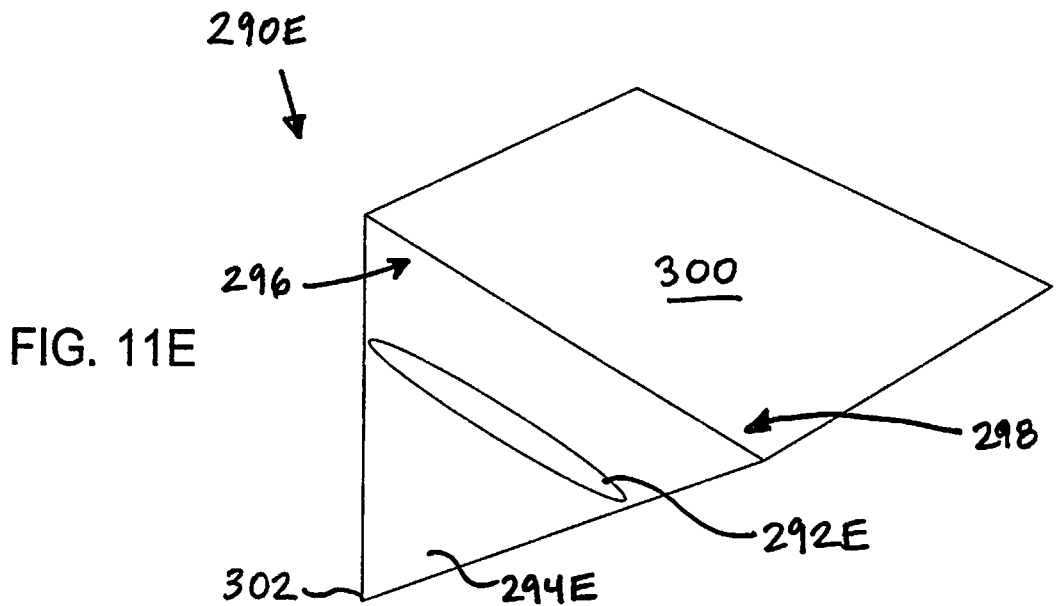
Figure 11F:
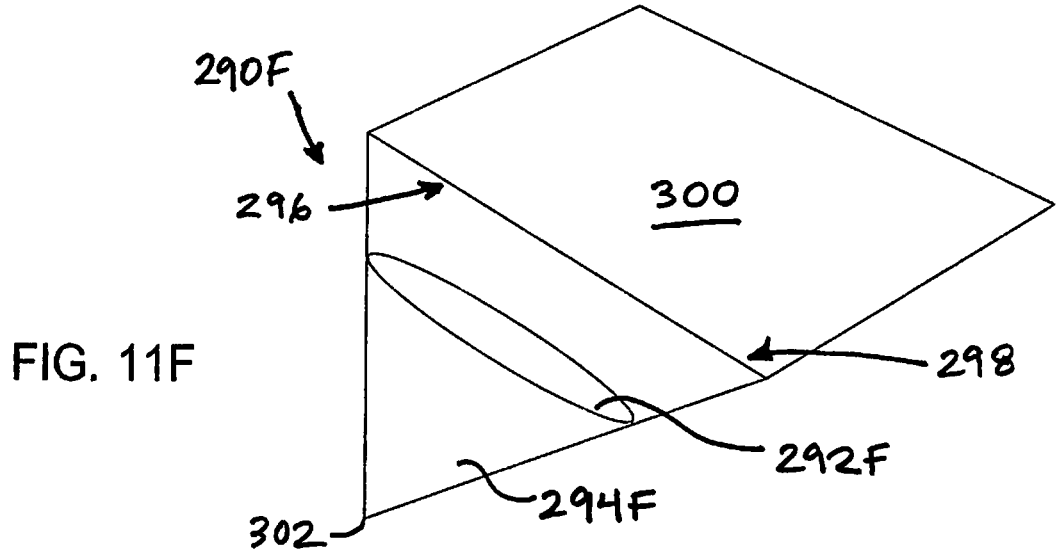
Figure 11G:
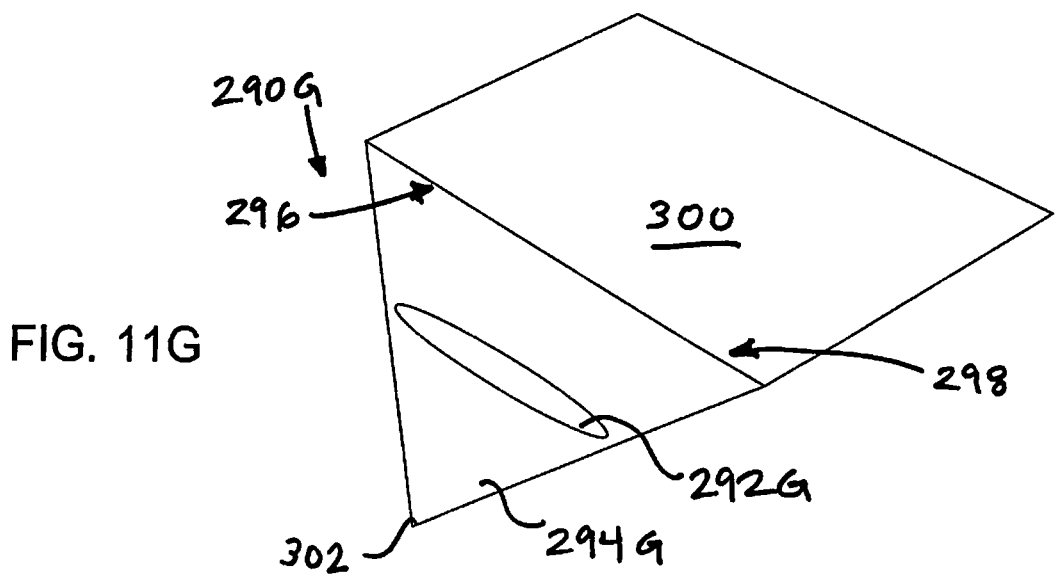
Figure 11H:
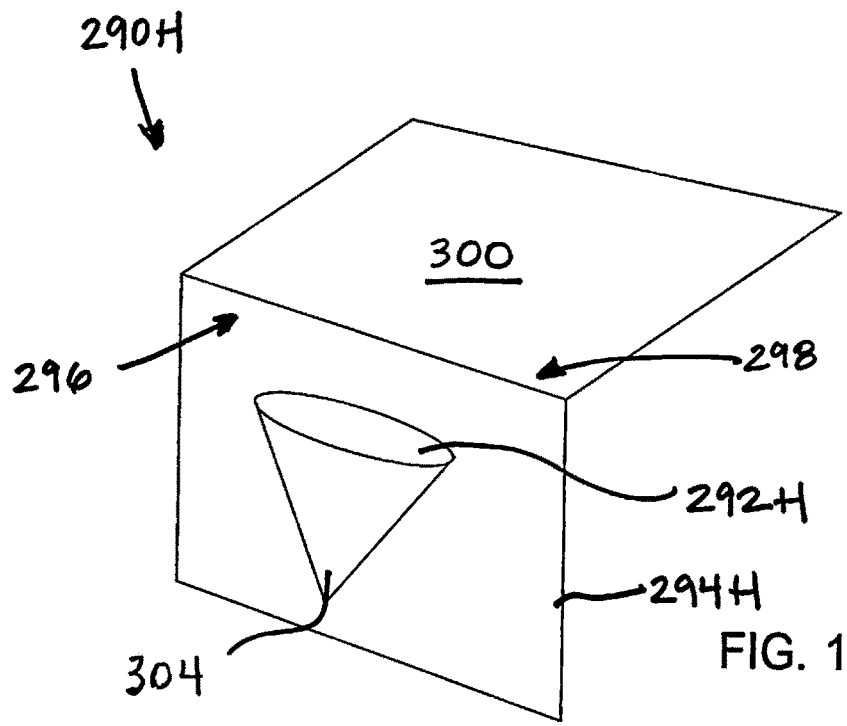

FIGS. 11A-11H respectively show devices 290A-290H with different placement and sizes of openings 292A-292H in collection bags 294A-294H contemplated for use in accordance with certain aspects of the present disclosure. As can be seen, a slit forming the openings 292A-292H may be large and extend fully across from one edge to the other (see e.g., openings 292A, 292D, and 292F in the designs in FIGS. 11A, 11D, and 11F) or may be intermediate (see e.g., openings 292B, 292E in the designs in FIGS. 11B, and 11E) or small (see e.g., openings 292C, 292G, and 292H in the designs in FIGS. 11C, 11G, and 11H), so that the slit only extends over a portion of the span of the bag 294C, 294G, and 294H. Further, the slit may be placed in different vertical positions along the collection bag. The slit or opening may be high up near a tongue region 296 of a distal end 298 of a mat portion 300 of the device so that it is longer (see e.g., the designs in FIGS. 11A, 11D, 11E, and 11G), or may be moved down vertically closer to an apex or terminal region of the triangle of the bag shape (see e.g., the designs in FIGS. 11B, 11C, and 11H). For a triangular bag, the slit length decreases as the slit is moved down vertically towards the apex of the triangle. FIG. 11F shows an opening with a cone shape 304. Methods for securing the mat 300 to the support (not shown) include hook and loop fasteners, magnets, straps, such as 2 straps or 4 straps that can be tied to the patient, buttons, adhesive, sticky putty, and the like.

Figure 12:
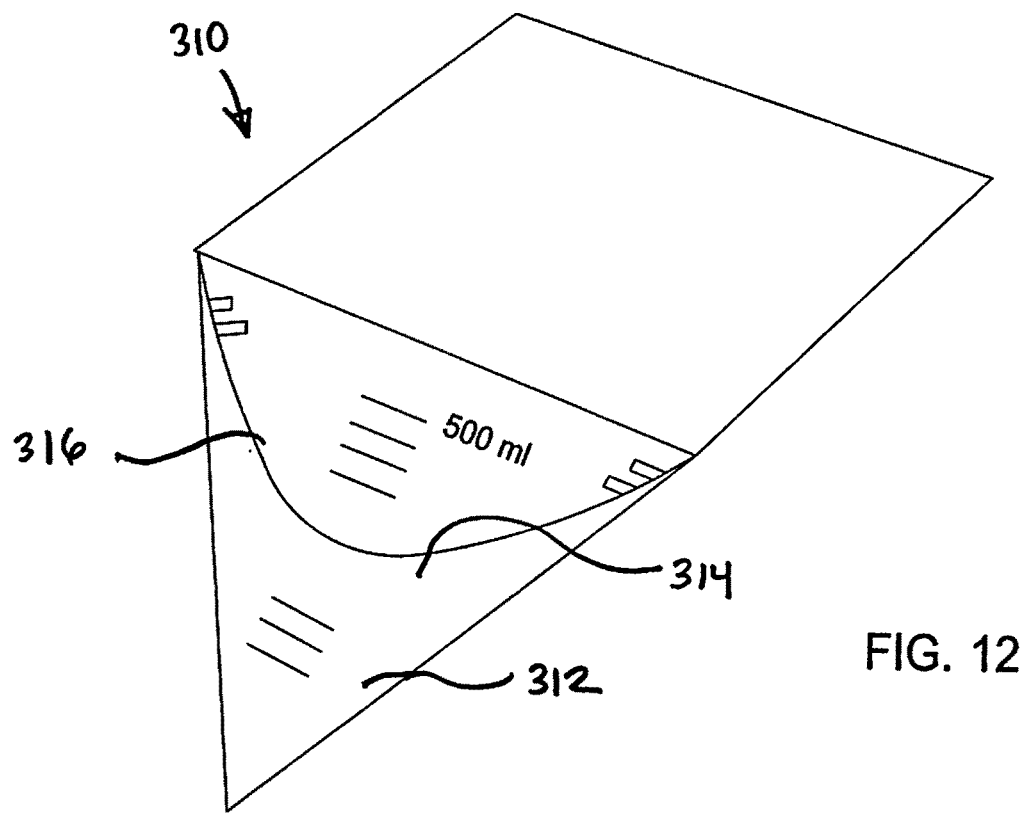
FIG. 12 is an illustration of a variation of a device for collecting bodily fluids from a patient during and after childbirth prepared in accordance with certain aspects of the present disclosure where a collection bag has an overflow chamber.

FIG. 12 is an illustration of a variation of a device 310 for collecting bodily fluids from a patient during and after childbirth prepared in accordance with certain aspects of the present disclosure where a collection bag 312 has an overflow chamber 314. As shown, there is a second collecting chamber 316 associated with the collection bag 312 that can collect overflow of bodily fluids from the main chamber.

Figure 13:
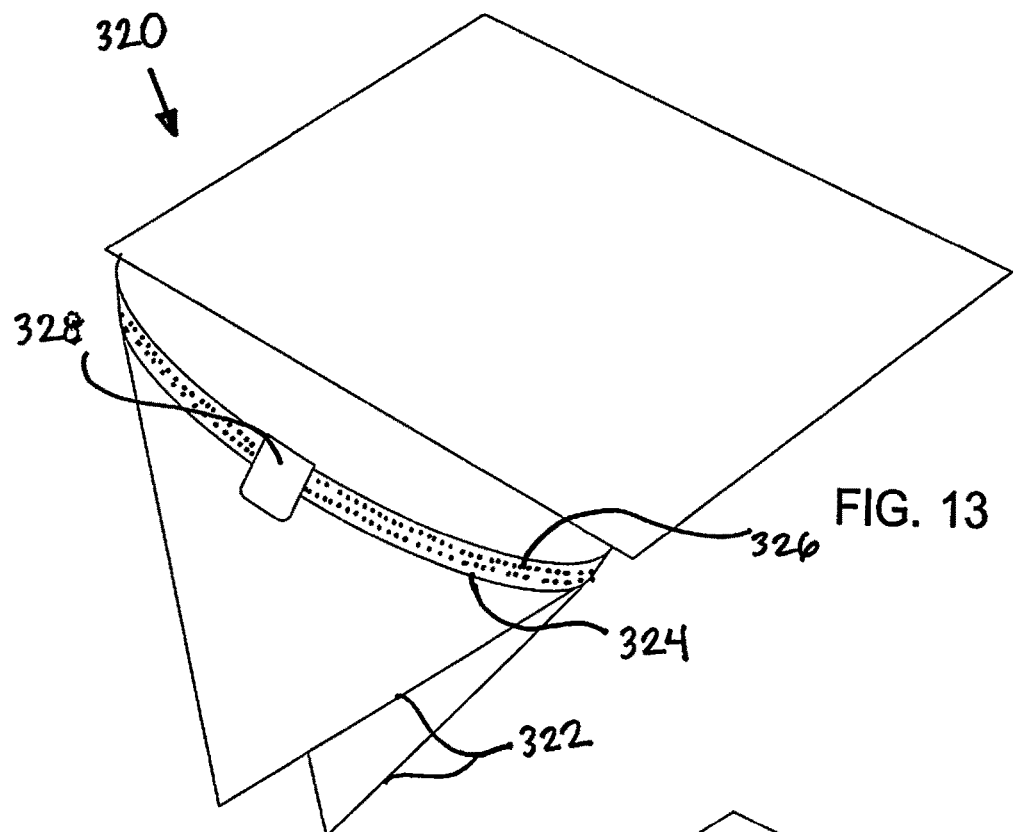
FIG. 13 is an illustration of a variation of a device for collecting bodily fluids from a patient during and after childbirth prepared in accordance with certain aspects of the present disclosure where a collection bag has a protective sleeve or pocket.

FIG. 13 is an illustration of a variation of a device 320 for collecting bodily fluids from a patient during and after childbirth prepared in accordance with certain aspects of the present disclosure where at least one collection bag 322 has a protective sleeve or pocket 324. The protective pocket 324 can protect a closure mechanism 326 beneath the protective pocket 324, such as a thermoplastic adhesive. There may also be a clip or tie 328 for releasing the protective sleeve 324 when the closure mechanism 326 needs to be activated after use of the collection bag 322.

Figure 14A:
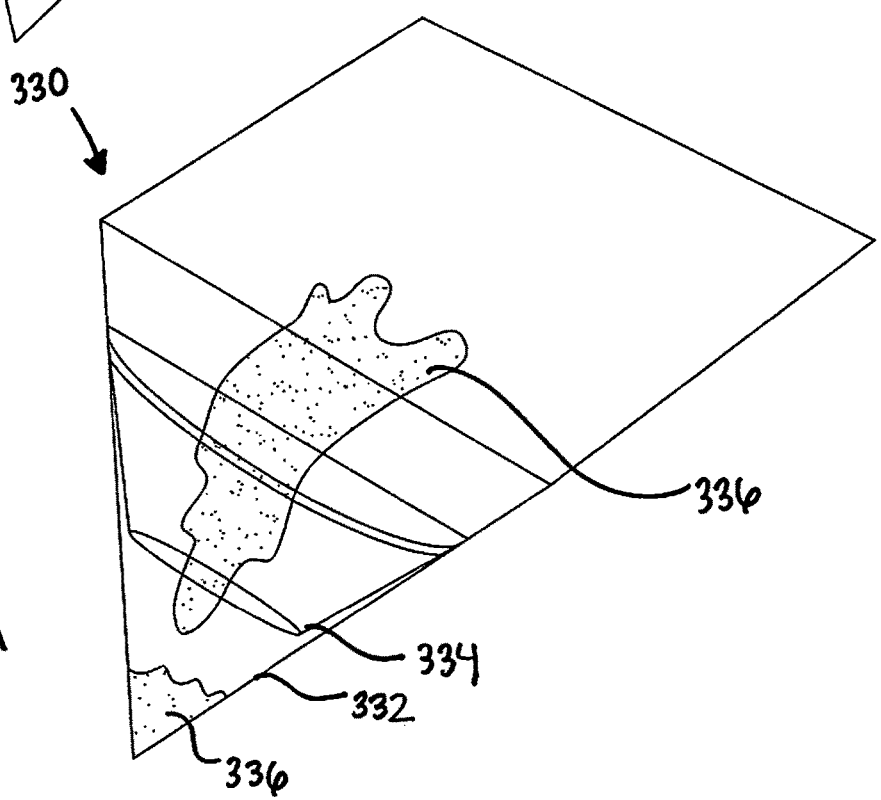
FIGS. 14A-14B show illustrations of yet another variation of a device for collecting bodily fluids from a patient during and after childbirth prepared in accordance with certain aspects of the present disclosure where a first collection bag is disposed within a second collection bag.
Figure 14B:
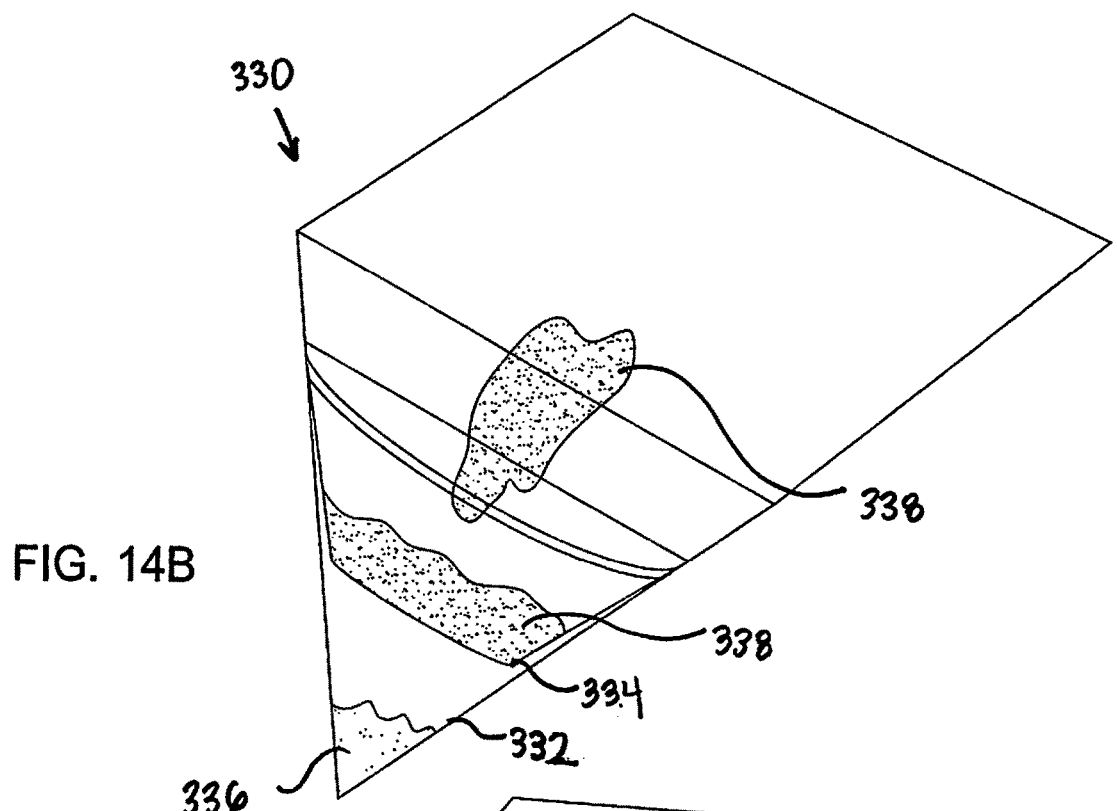

FIGS. 14A-14B show an illustration of yet another variation of a device 330 for collecting bodily fluids from a patient during and after childbirth prepared in accordance with certain aspects of the present disclosure where a first collection bag 332 is disposed within (or nested within) another second collection bag 334. In a first operational mode, the first collection bag 332 may be open during the first stages of delivery and collect initial bodily fluids 336. Then, in a second operational mode, the first collection bag 332 may be closed between the second and third stages of labor, while the second collection bag 334 is open so that the second bag then collects subsequent bodily fluids 338, including blood.

FIGS. 15A-15B are illustrations of variations of a device 340 for collecting bodily fluids from a patient during and after childbirth prepared in accordance with certain aspects of the present disclosure where a collection bag 342 has two distinct compartments, a first compartment 344 and a second compartment 346. In FIG. 15A, a slider mechanism 348 can be used to create an opening 350 to the first compartment 344 during a first operational mode to collect fluids in the first compartment 344, while the second compartment 346 is closed. Then, in a second operational mode, the slider mechanism 348 can be adjusted to close the first opening 350 to the first compartment 344, while second opening 352 to the second compartment 352 is accessible. In this manner, the second compartment 346 collects bodily fluid in the second operational mode. In FIG. 15B, a device 340B includes a sliding or folding lid 354 can be used to create an opening 350B to the first compartment 344 during a first operational mode to collect fluids in the first compartment 344, while the second compartment 346 is closed. Then, in a second operational mode, the sliding or folding lid 354 is adjusted to close the first opening 350B to the first compartment 344, while the second opening 352B to the second compartment 346 is open. In this manner, the second compartment 346 collects bodily fluid in the second operational mode.

FIGS. 16A-16B are an illustration of a variation of a device 360 for collecting bodily fluids from a patient during and after childbirth prepared in accordance with certain aspects of the present disclosure where a collection bag 362 has a filter device 364 at an opening 366. When blood 368 is collected during the second operational mode shown in FIG. 16B, extra blood clots can fall through the filter 364 to an internal tube 370 in the collection bag 362 to be collected.

FIG. 17 is an illustration of another variation of a device 380 for collecting bodily fluids from a patient during and after childbirth prepared in accordance with certain aspects of the present disclosure. The device 380 includes two detachable and sealable collection bags 382. Thus, there is a first detachable and sealable bag 384 for collecting initial bodily fluids 386 in the first operational mode and a second detachable and sealable bag 388 for collecting subsequent bodily fluids 390 in the second operational mode.

FIGS. 18A-18B show illustrations of one variation of a device 400 for collecting bodily fluids from a patient during and after childbirth prepared in accordance with certain aspects of the present disclosure where a distal end 402 of a mat 404 has a specialized material 406 disposed within a flow field 408 for the bodily fluids. The specialized material 406 soaks non-blood fluids 410 as shown in FIG. 18A and disintegrates, so that as shown in FIG. 18B, blood 412 flows through the material and into the collection bag below (not shown) for measurement (e.g., during the second operational mode).

In certain variations, a distal end of a mat of a device for collecting bodily fluids from a patient during and after childbirth prepared in accordance with certain aspects of the present disclosure defines a shape selected from a trapezoid, a triangle, and a rectangle. This distal region of the mat that defines a terminal end of the flow field leading into the opening of a collection bag may be considered a tongue. By way of example, FIGS. 19A and 19B show a first device 420A and a second device 420B, each having a distal region 422 of a mat 424 having a triangular shaped tongue 426. Second collection bags 428A and 428B, respectively have two shapes, including a diamond shape in second collection bag 428A in FIG. 19A and a triangular shape in second collection bag 428B FIG. 19B. The triangular shaped tongue 426 is thus capable of connecting to each collection bag, whether having a diamond shape in first collection bag 428A or a triangular shape in second collection bag 428B.

Figure 20H:
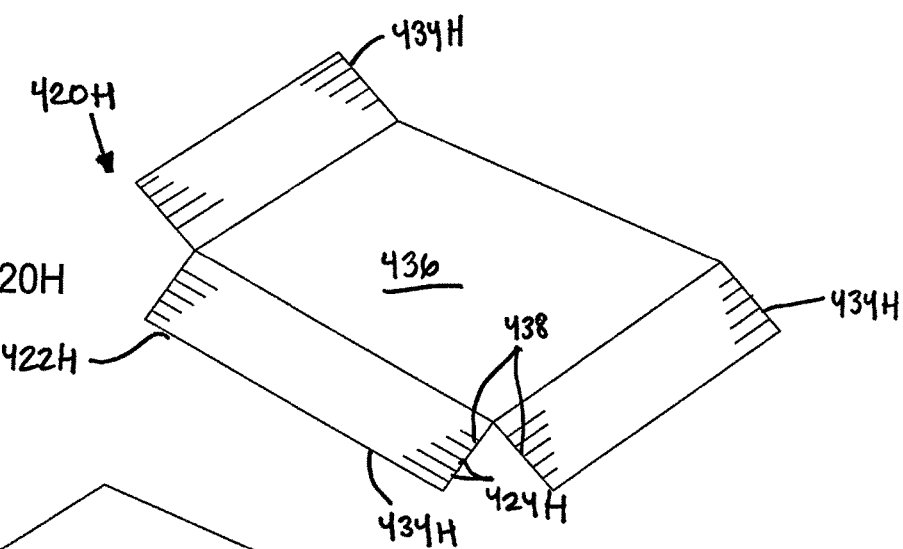
Figure 20I:
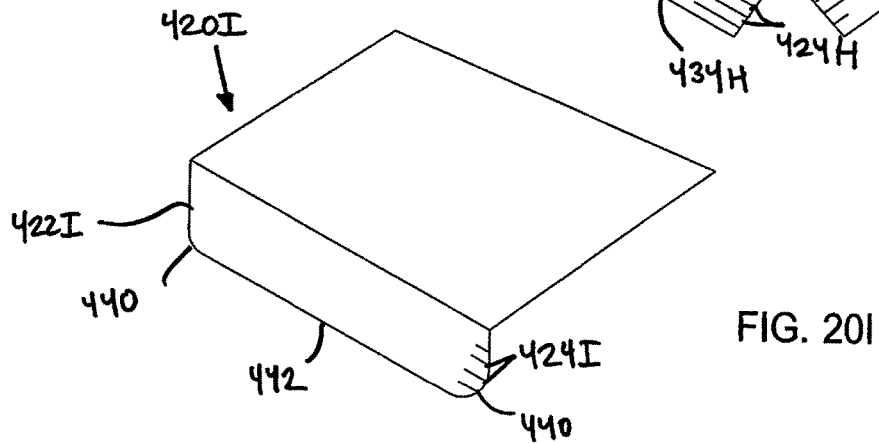

FIGS. 20A-20I are illustrations of various representative examples of devices 420A-420I for collecting bodily fluids from a patient during and after childbirth prepared in accordance with certain aspects of the present disclosure, where a second collecting bag 422A-422I for a second operational mode may have a variety of different shapes or designs. Notably, the first collection bags (not shown) may also have the same shape. FIGS. 20A-20I show volume indicators 424A-424I used in the second collection bag 422A-422I. In the device 420A of FIG. 20A, the second collection bag 422A has a triangular shape with a pointed apex 426. In the device 420B of FIG. 20B, the second collection bag 422B has a trapezoidal shape. In the device 420C of FIG. 20C, the second collection bag 422C has a triangular shape with a rounded apex 428. In the device 420D of FIG. 20D, the second collection bag 422D has a trapezoidal shape with rounded corners at the bottom edge 430. In the device 422E of FIG. 20E, the second collection vessel 422E is in the form of a cylinder 432, which provides a high level of accuracy. In the device 420F of FIG. 20F, the second collection bag 422F has a rectangular shape. In the device 420G of FIG. 20G, the second collection bag 422G has a rectangular shape and there are rectangular collection bags 434 that extend around multiple sides of a mat portion 436 of the device 420G. Thus, a first rectangular collection bag is in fluid communication with the distal end of the flow region of the mat, while second and third rectangular collection bags 434 are disposed on the peripheral sides of the mat 436, so that they would hang off each side of the support structure (e.g., hospital bed). The edges of the first, second, and third collection bags 434 are connected to one another. The device 420H shown in FIG. 20H is similar to that shown in FIG. 20G, but edges 438 of the three collection bags 434H are disconnected from one another. Finally, in the device 420I shown in FIG. 20I, the second collection bag 422I has a rectangular shape with rounded corners 440 at the bottom edge 442. As will be appreciated by those of skill in the art, these collection bag shapes are representative, but other shapes may likewise be feasible.

FIGS. 21A-21C show various representative examples of devices 450A-450C for collecting bodily fluids from a patient during and after childbirth prepared in accordance with certain aspects of the present disclosure, where a collecting bag 452A-452C for either the first or second operational modes are triangular, but have different sizes. In other words, the triangles may have a greater side length or a shorter side length to form collection bags of different sizes. FIG. 21A shows a collection bag 452A having a larger triangle with relatively longest sides 454A. FIG. 21B shows a collection bag 452B having a triangular shape with medium length sides 454B. FIG. 21C shows a collection bag 452C a shorter side 454C creating a triangular shape with a relatively small triangle.

FIG. 22 illustrates another example of a device 460 for collecting bodily fluids from a patient during and after childbirth prepared in accordance with certain aspects of the present disclosure, where a collecting bag 462 has a wine glass shape to direct fluids from an upper portion 464 to a lower portion 466 of the collecting bag 462. As shown, at an opening 468, the collecting bag 462 is wider defining a rounded hemispherical cone or bowl 470 that funnels into a narrower stem portion 472 that leads to a cylindrical shape 474 that may have volume indicator markings 476. The cylindrical shape 474 may be similar to a graduated cylinder style of collection vessel.

FIGS. 23A-25E illustrate various examples of devices for collecting bodily fluids from a patient during and after childbirth prepared in accordance with certain aspects of the present disclosure, where a closure mechanism for a collecting bag involves cinching. In FIGS. 23A-23F, two distinct devices 480A in FIGS. 23A-23C and 480B in FIGS. 23D-23F are provided, where a collecting bag 482A or 482B has a cinching string 484 disposed around a circumference of a top 486 of the collecting bag 482A or 482B. In FIG. 23A, the collecting bag 482A may be attached to a distal end 488 of a mat portion 490 via a perforated tear line 492 and may have an adhesive strip 494 attaching the bag 482A to the mat 490. When the first or second operation mode is completed and the bag 484A is to be removed as shown in FIG. 23B, the adhesive strip 494 can be lifted off and the cinching string 484 pulled to cinch or draw an opening 496 closed as shown in FIG. 23C.

Figure 23E:
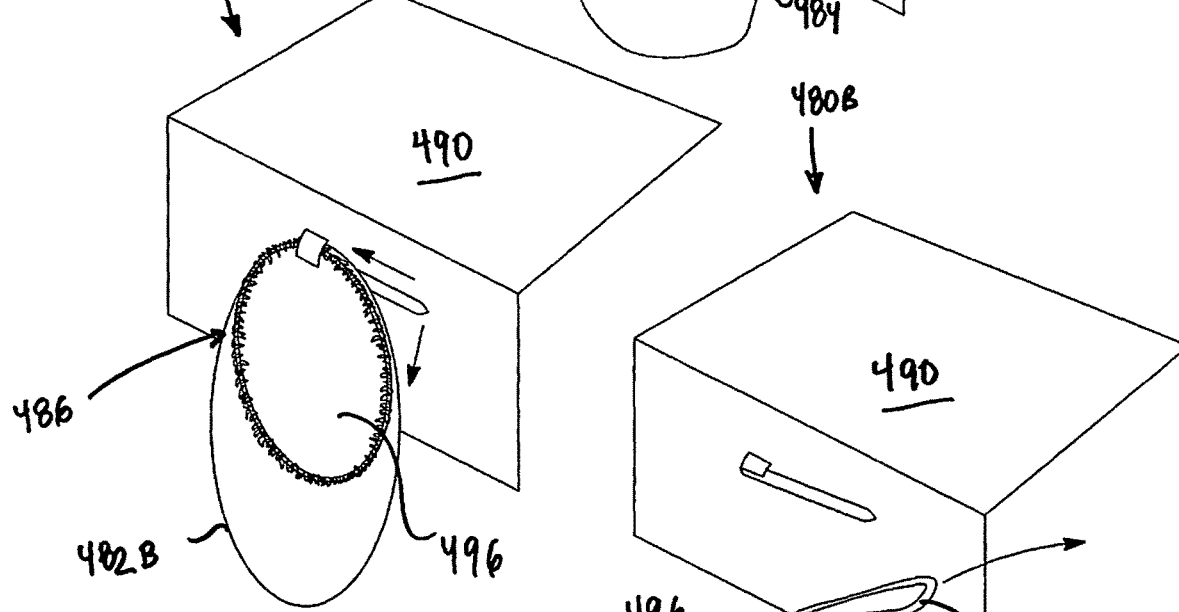
Figure 23F:
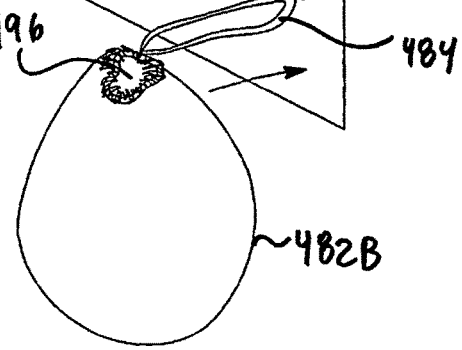

In another variation in FIGS. 23D-23F, the collecting bag 482B may be attached to the distal end 488 of the mat portion 490 via a zipper 500, as shown in FIG. 23C. Thus, when the first or second operational mode is completed and the bag 482B is to be removed, the zipper 500 can be unzipped as shown in FIG. 23D to tear the collection bag away and the cinching string 484 pulled to cinch or draw the opening 496 closed. The bag 482B can then be removed as shown in FIG. 23F.

In FIGS. 24A-24C, a device 510 includes a collecting bag 512 that may be attached to a distal end 514 of a mat portion 516 via a perforated tear line 518, but in this variation does not have an adhesive strip attaching the bag 512 to the mat 516 like in FIGS. 23A-23C. The collecting bag 512 has a cinching string 518 disposed around a circumference of a top 520 of the collecting bag 512 as shown in FIG. 24A. When the first or second operation mode is completed and the collecting bag 512 is to be removed, the bag 512 can be torn away from the mat portion 516 along the perforated tear line 518 as shown in FIG. 24B and then the cinching string 518 pulled to cinch or draw an opening 522 closed as shown in FIG. 24C.

In FIGS. 25A-25E, a device 530 includes at least one collecting bag 532 may be attached to a distal end 534 of a mat portion 536 via a perforated tear line 538 and may comprise side tabs or straps 540 as shown in FIG. 25A. The tabs or straps 540 can be used to pull the collection bag 532 away from the perforated tear line 538 and remove the collection bag 532 from the mat 536, as shown in FIGS. 25B-25C. After the removal in FIG. 25D and detachment of the collection bag 532, the tabs or straps 540 can be cinched and tied to pull an opening 542 closed as shown in FIG. 25E.

FIGS. 26A-26B illustrate another variation of a device 550 for collecting bodily fluids from a patient during and after childbirth prepared in accordance with certain aspects of the present disclosure, where a collection region 552 includes two distinct collection chambers, a first collection chamber 554A and a second collection chamber 554B and a valve or funnel 556 is used to switch between the distinct collection chambers (554A) in a first operational mode versus a second operational mode (554B) of the device 550. In a first operational mode in FIG. 26A, the initial bodily fluids 558, such as amniotic fluid, are directed towards the first collection chamber 554A. In a second operational mode shown in FIG. 26B, the funnel or valve 556 is diverted to direct fluid flow towards the second collection chamber 554B. The subsequent bodily fluids 560, such as blood, are directed to the second collection chamber 554B, which has a volume indicator 562 for a user to be able to measure the volume of bodily fluids. The valve or funnel 560 of some variations is a manually manipulated valve or funnel such that a user can manually switch the device from the first operational mode to the second operational mode. In other variations, movement of the valve or funnel 560 may be automated with standard equipment not shown here.

In FIGS. 27A-27B, a device 570 for collecting bodily fluids from a patient during and after childbirth prepared in accordance with certain aspects of the present disclosure has a collecting bag 572 with a visual volume indicator 574 to measure the bodily fluids collected in the second sealable bag. The visual volume indicator 574 is a ring 576 disposed inside the transparent collecting bag 572 that has angled gradations, allowing an observer to discern measurements from any viewing angle.

In FIG. 28, a device 580 for collecting bodily fluids from a patient during and after childbirth prepared in accordance with certain aspects of the present disclosure has a mat portion 582 with inflatable dams 584 along peripheral edges 586 to define bumpers. Thus, each peripheral edge 586 has an inflatable dam 584 or may be formed of a solid lightweight material (such as closed foam) to help define a flow field region 588 of the surface of the mat 582 and prevent egress of bodily fluids over the peripheral sides 586 of the mat 582. The inflatable dam 584 may have closable ports (not shown) so that the dams 584 can be inflated with air when the device 580 is to be used.

In FIGS. 29A-29D, variations of a device for collecting bodily fluids from a patient during and after childbirth prepared in accordance with certain aspects of the present disclosure has a mat portion incorporating a shape memory material, such as a shape memory polymer. Thus, in one variation in FIG. 29A, a device 590A includes a distal region 592 of a mat 594 that defines a terminal end 596 of a flow field 598 leading into an opening 600 of a collection bag 602 that may be considered a tongue. This region may be formed of a shape memory material 604 that has a trained shape. When the material 604 reverts to its trained shape (for example, by application of heat) as shown in FIG. 29B, it can be placed within the opening 600 of the collection bag 602 to better direct flow of fluids from the flow field 598 into the bag 602. In another variation in FIGS. 29C-29D, a device 590B includes a mat 594B having peripheral sides 606 formed of a shape memory material 608, which when activated (in FIG. 29D) can direct bodily fluid flow from the flow field 598B towards the distal end 592 over the terminal edge 596 of the mat 594B and prevent undesirable flow over the peripheral edges 606 of the mat 594B.

In FIG. 30, a device 610 for collecting bodily fluids from a patient during and after childbirth prepared in accordance with certain aspects of the present disclosure has a mat portion 612 with recessed channels 614 formed along and near peripheral edges 616 to define fluid flow channels. Thus, each peripheral edge 616 has a recessed groove or channel 614 to help direct bodily fluids towards a distal end 618 of the mat 612 and prevent egress of bodily fluids over the peripheral sides 616 of the mat 612.

FIG. 31 illustrates an example of a closure mechanism 620 for a device for collecting bodily fluids from a patient during and after childbirth prepared in accordance with certain aspects of the present disclosure, where the closure mechanism 620 for a collecting bag 622 is capable of both sealing and tearing the collecting bag 622 from a mat portion 624. Like previous embodiments, there may be a perforated tear line (not shown), so that when the closure mechanism 620 has a slide and cutter 626, as it is drawn over an opening of the bag 622 for sealing, it likewise cuts or physically removes the bag 622 so that it can be detached.

FIG. 32 illustrates another variation of a device 630 for collecting bodily fluids from a patient during and after childbirth prepared in accordance with certain aspects of the present disclosure. In this variation, only one single sheet of plastic 632 may be used during manufacturing. The manufacturing process may involve heat sealing. Thus, two ends of the plastic sheet 632 are folded upon one another to define a mat portion 634 and two collection bags 636 nested over one another at a distal end 638 of the device 630. A fastener 648 may be provided to secure the pieces of the sheet together in one variation. The sheet 632 is heat sealed at the distal end 638 of the mat 634 to join the pieces of the sheet 632 together. Each collection bag 636 may have a closure mechanism 640 and optionally a shape memory material 642. A tear tab or tear line 644 may be defined above at least the first collection bag 636 for the first operational mode. Further, as in the previous embodiment, when the closure mechanism 640 is a slide and cutter, it can be drawn over an opening 646 of the bag 636 for sealing and cutting or physically removing the bag 636 so that it can be detached.

FIG. 33 illustrates another variation of a device 650 for collecting bodily fluids from a patient during and after childbirth prepared in accordance with certain aspects of the present disclosure, where a collection bag 652 comprises an opening 654 to receive bodily fluids and a port 656 for drawing fluids out of the collection bag or container 652. Thus, the bodily fluids travel down the fluid flow region towards the collection bag or container 652. A port 656 in the bag 652 can be connected to another component or device to draw suction or to transfer the fluid in the compartment to another component. Thus the port 656 ensures the device 650 is compatible with a suction machine. After the fluid or bodily substances are transferred away from the collection bag or container 652, it can be further processed, for example, separated or filtered.

Another device 660 for collecting bodily fluids from a patient during and after childbirth prepared in accordance with certain aspects of the present disclosure shown in FIGS. 34A-34C can be used to capture blood. An absorbent material 662 may be disposed in a collection bag 664 as shown in FIG. 34A (e.g., the second collection bag used in a second operational mode of the device) to absorb the blood or other bodily fluids 666 received, as shown in FIG. 34B. The absorbent material 662 may remove liquid waste and avoid spillage. The absorbent material 662 is then be removed from the collection bag 664 in FIG. 34C and optionally weighed on a scale 668 to provide additional quantification of blood loss.

FIG. 35 is another variation of a device 670 for collecting bodily fluids from a patient during and after childbirth prepared in accordance with certain aspects of the present disclosure, where a collection bag 672 has a stiffening or rigid component 674 on a back side 676 of the second collection bag 672, which makes a visual volume indicator 678 more visible to a user of the device 670. In such a variation, the bag 672 may have a high diameter.

Figure 36A:
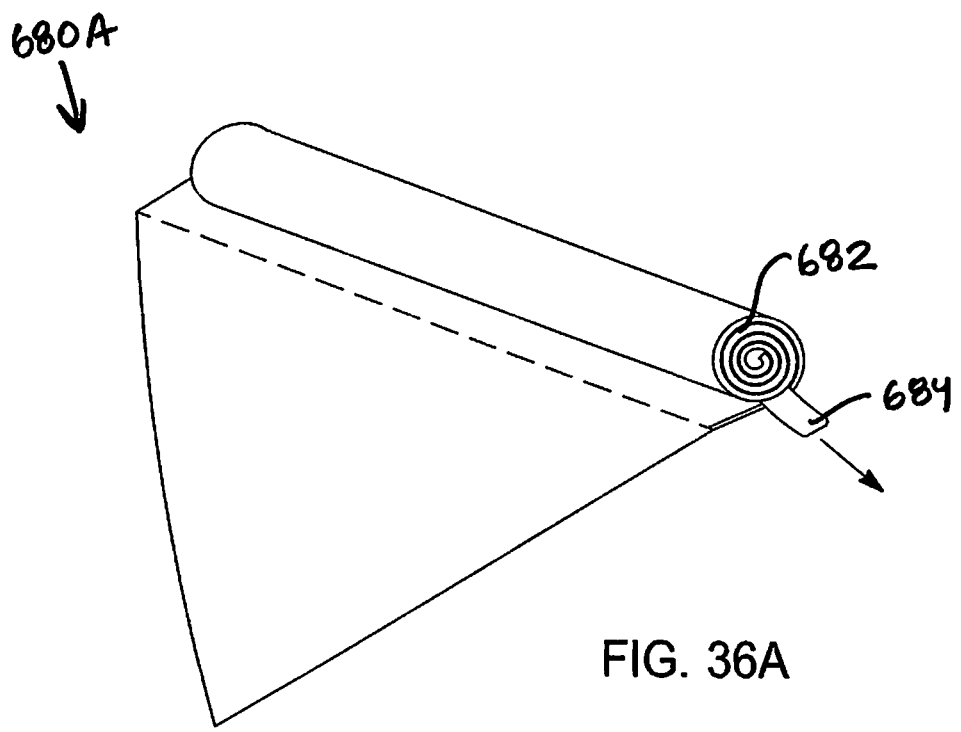
Figure 36B:
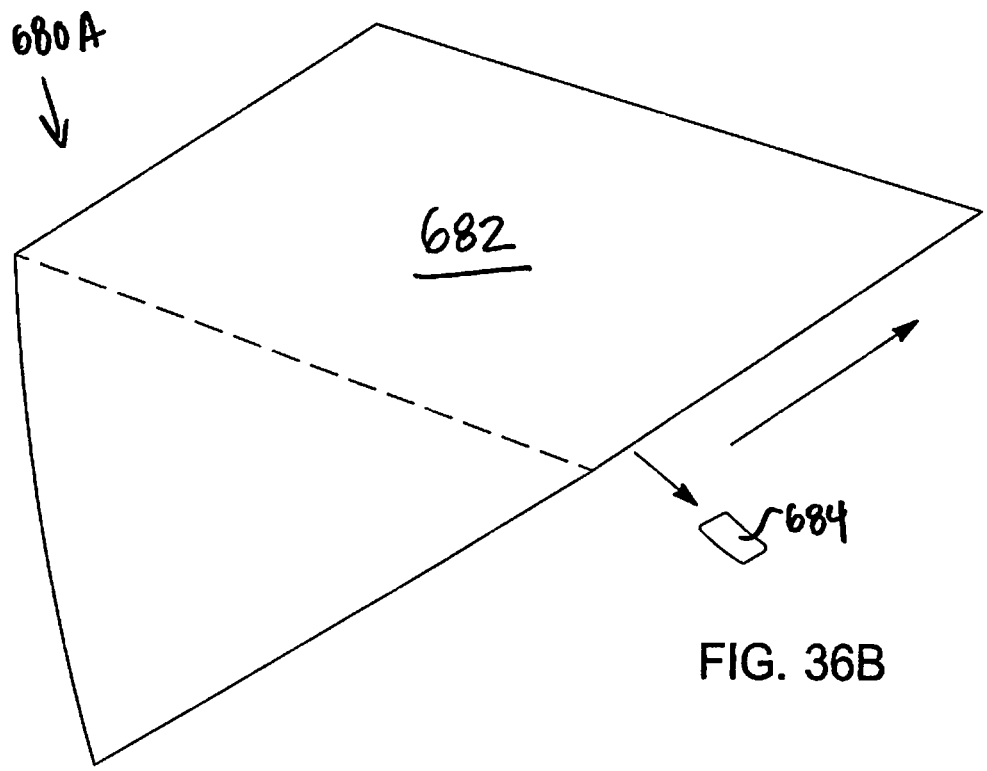
Figure 36C:
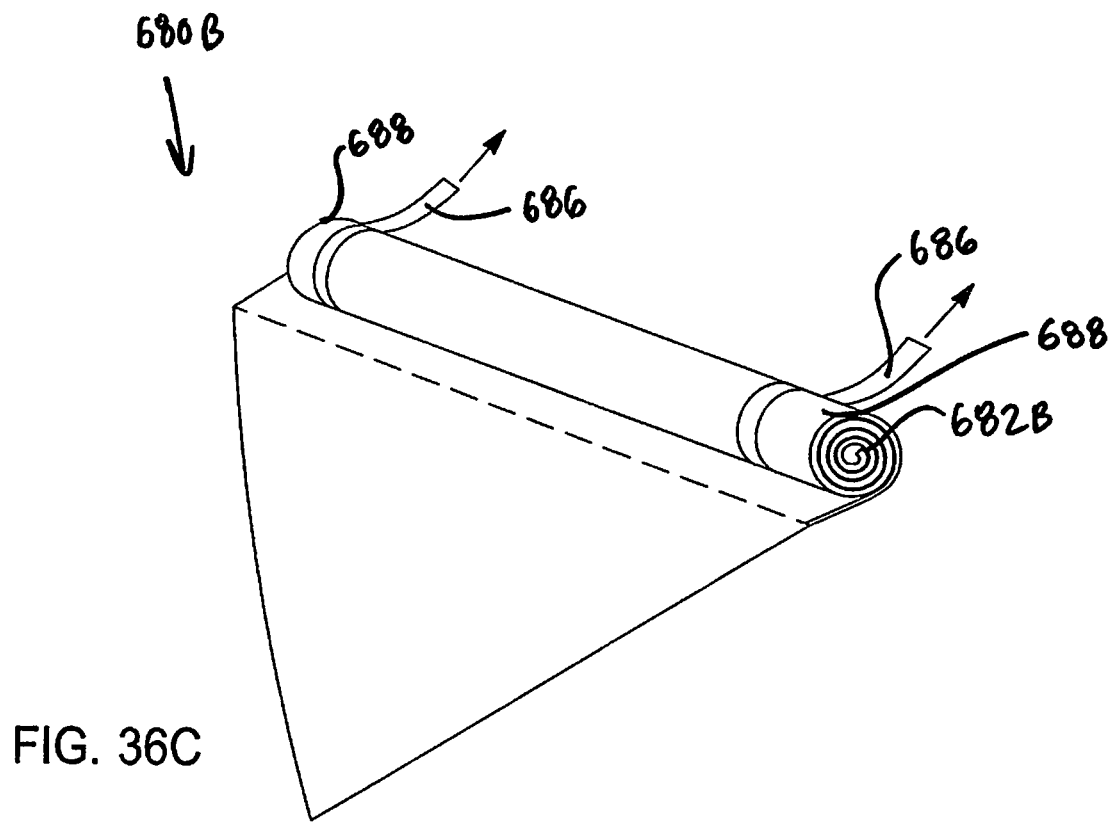
Figure 36D:
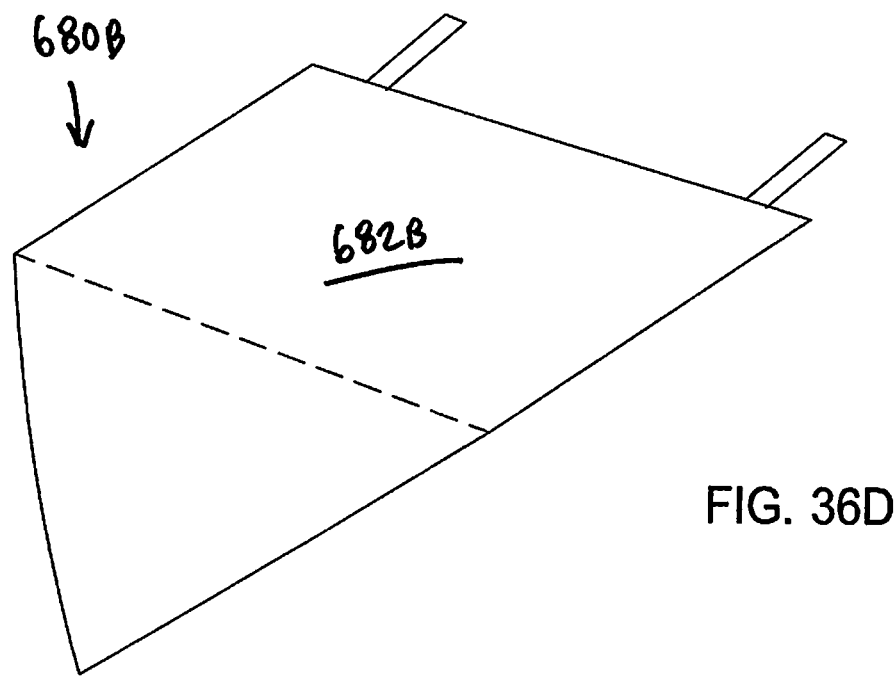

In FIGS. 36A-36B, a first device 680A for collecting bodily fluids from a patient during and after childbirth prepared in accordance with certain aspects of the present disclosure has a mat portion 682 that can enhance ease of use. In FIG. 36A, the mat portion 682 is rolled and has a tab 684 that can be pulled. When a patient lifts above the support (not shown), the tab 684 can be pulled to activate the mat portion 684 to unroll beneath the patient as shown in FIG. 36B. Likewise, FIG. 36C also shows another similar device 680B where a rolled portion of the mat 682B has two strips 686 near terminal edges 688 of the rolled mat portion 682B. The strips 686 can be pulled apart to unroll the mat portion 682B beneath a patient as shown in FIG. 36D.

FIGS. 37A-37B show yet other variations of devices 690A and 690B, respectively, for collecting bodily fluids from a patient during and after childbirth prepared in accordance with certain aspects of the present disclosure, where a mat portion 692A and 692B is reusable and first and second collection bags 694 (only shown as a single bag) are disposable. Thus, in certain variations, the mat 692A may be reusable as shown in FIG. 37A and the first detachable and sealable bag and the second sealable bag 694 comprises at least one connector 696 to reversibly couple and physically connect the first and second bags 694 with the mat 692A. Notably, the at least one connector is strong enough to support the weight of each bag when it is filled to capacity with bodily liquids. In the variation shown in FIG. 37A, the connector 696 may be a loop, button, or snap with two mating sides that is disposed on a distal end 698 of the mat portion 692A and on an upper region 700 of the collection bag 694. As shown, there are two buttons on each side of the distal end 698 of the mat portion 692A and on the upper region 700 of each bag 694. The first bag 694 may thus be detached, disposed of and replaced with the second bag via use of the reusable connectors in the second operational mode. FIG. 37B shows another variation of a device 690B with disposable compartments or bags 694 attached to the reusable mat 692B. In other variations, the device 694 may be reusable or disposable, and one or both of the first detachable and sealable bag and the second sealable bag may be detachably attached to the distal end of the mat via a plurality of snaps, clips, or buttons, a zipper, and/or a perforated seam.

Where components are reusable, in certain aspects, it may last up to about 3 years and may be able to withstand greater than or equal to about 7,000 total uses. In certain variations, the reusable mat portion of the device can be thoroughly and easily cleaned with the available sanitation methods. By way of example, sterilization procedures within the labor wards may include soaking any contaminated nonmetal tool in a 10% bleach solution for 10 minutes for up to 12 hours. In certain variations, the reusable portions of the device like the mat portion do not degrade after being left in a 10% bleach solution for up to 12 hours. Furthermore, the reusable portions of the device are safe, for example, being defined as there being less than or equal to 6.7% risk of patient transmission of infection after cleaning and/or sterilizing. Thus, the device does not increase a risk of transmission of blood borne pathogens from patient-to-patient or patient-to-provider through use of the device and does not create any additional routes for patient-to-patient transmissibility of infectious or blood borne diseases. Moreover, the healthcare provider advantageously does not come into contact with the blood collected.

In FIG. 38, a device 710 for collecting bodily fluids from a patient during and after childbirth prepared in accordance with certain aspects of the present disclosure has a mat portion 712 with a proximal end 714 including a flap or folded region 716. The flap or folded region 716 is configured for a user to use hands 718 to tuck the device 710 under a patient and position the device 710. The flap 716 may be sealed on three of four edges 718, leaving a single side 720 open for insertion of hands 718.

FIGS. 39A-39E, 41A-41F, and 42A-42B illustrate examples of a device for collecting bodily fluids from a patient during and after childbirth prepared in accordance with certain aspects of the present disclosure, where a first detachable collection bag has a triangular (or conical) shape for a first operational mode of the device, while the second collection bag for a second operational mode may have a different shape from the first collection bag. For example, as best seen in FIGS. 39A-39E, 41E, and 42A, the second collection bag has a wineglass shape similar to that shown in FIG. 22. Thus, the upper region of the second collection bag near the distal end of the mat is wider and defines a rounded cone or bowl that funnels into a narrower stem portion that has a cylindrical shape, which has volume indicator markings (e.g., into a graduated cylinder vessel) To the extent that the device in FIGS. 39A-39E share the same components or features as those shown in FIGS. 2A-2D, they will not be reintroduced or discussed for brevity. FIGS. 39A-39C show device 20A being used in the first operational mode, while FIG. 39D shows the second operational mode where the first detachable and sealable bag 50 is detached from the device 20A after stage 2 of delivery. Thus, as shown in FIG. 2D, the second operational mode of device 20A begins after the baby and optionally after the placenta are delivered (transitioning to the second operational mode when delivery stages 2 and 3 are completed). In FIGS. 39A-39C, the first detachable and sealable bag 50 is disposed over a second sealable bag 60A that has a different shape. Once the first detachable and sealable bag 50 is sealed by the closure mechanism 54, the first detachable and sealable bag 50 may be removed at the tear line 56 are separated from the device 20A, as shown in FIG. 2C.

The second sealable bag 60A has a second opening 62A in fluid communication with the distal end 34 of the fluid flow region 46 and configured to receive the bodily fluids 48 from the patient 42 in a second operational mode of the device 20A. The second sealable bag 60A may define an entry region that has a triangular shape, which in three dimensions create a cone-shape. This entry region may alternatively be hemispherical or have other shapes that direct fluid towards a lower region of the second sealable bag 60A. As described above, the second sealable bag 60A is formed of a polymeric material and may be disposable. The second sealable bag 60A may optionally be detachable from the mat 30, although in the embodiment shown it is not detachable. The second sealable bag 60A may have indicia that are a visual volume indicator 64 (best seen in FIGS. 39E, 41F, 42A-42B) having marked gradations to measure a volume of the bodily fluids 48 collected in the second sealable bag 60. The second sealable bag 60 also may have a closure mechanism 66. During the second operational mode of the device 20, where the second sealable bag 60 collects bodily fluids 48, the bodily fluids 48 tend to be blood and are most indicative of a potential postpartum hemorrhage. As will be described further below, a period of about 4 hours after the child is delivered is the most important period for observation of excessive blood loss from the patient to detect postpartum hemorrhage. The accurate measurement of blood loss is an important tool in order to diagnose PPH and initiate appropriate treatment, such as blood transfusions.

In this manner, the present disclosure provides a foldable, soft film obstetric device that can be disposed under the patient's buttocks. The device has a bifold two-compartment or bag collection mechanism, which are attached to the drape or mat and that provide the capability of separating blood from pre-delivery and delivery fluids by using temporal relationship of vaginal delivery. Thus, the device provides a first operational mode and a second operational mode, where blood loss is measured in the second sealable bag 60 during the second operational mode. The second sealable bag 60 with marked volume gradations collects and quantifies hemorrhaging blood accurately after the placenta is delivered.

FIG. 40 shows another example of a device 730 for collecting bodily fluids 740 from a patient during and after childbirth prepared in accordance with certain aspects of the present disclosure, where at least one of the collection bags 732 (here shown to be a non-limiting second collection bag like that shown in FIGS. 22, 39E, and 42A) has an additional component 734 that can hold dry waste 736, such as gauze, absorbent pads, and the like.

FIGS. 41A-41G show a device for collecting bodily fluids from a patient during and after childbirth prepared in accordance with certain aspects of the present disclosure. In FIG. 41A-41G, a first detachable collection bag has a triangular (or conical) shape for a first operational mode of the device, while a second collection bag for a second operational mode may have a distinct shape having a triangular (conical) upper region that transforms to a rectangular (cylinder) lower region having indicia to measure volume of fluids collected. FIG. 41A is a perspective view of the device for collecting bodily fluids from a patient during and after childbirth prepared in accordance with certain aspects of the present disclosure, including details of a first collection bag having a first triangular shape and a second collection bag having a distinct shape disposed behind the first collection bag. FIG. 41B is a perspective view of the device showing the first collection bag and visible regions of the second collection bag disposed behind the first collection bag. FIG. 41C is a top view of the device showing the first collection bag. FIG. 41D is a bottom view of the device showing the second collection bag visible and separated from the first collection bag. FIG. 41E is a front planar view of the first collection bag and second collection bag disposed behind the first collection bag. FIG. 41F is a back planar view of the second collection bag disposed behind the first collection bag. FIG. 41G is a side view of the device for collecting bodily fluids from a patient during and after childbirth prepared in accordance with certain aspects of the present disclosure. In certain aspects, the present disclosure contemplates a new, original and ornamental design for a device for blood loss measurement following childbirth to detect postpartum hemorrhage, as shown in FIGS. 41A-41G, of which the above description forms a part of the specification.

More specifically, FIGS. 41A-41G show a collection device 750 that includes a mat region 752 that defines a proximal end 754 and a distal end 756. The mat 752 is configured to be disposed between a support and patient, as previously described. The mat 752 comprises a surface 758 defining a fluid flow region 760 configured to direct flow of bodily fluids from the patient towards the distal end 756 of the mat 752. Use of the term bodily fluids is intended to include various substances generated by the body, including solids, semi-solids, and liquids. By way of non-limiting example, examples of bodily fluids may include amniotic fluid, blood, blood clots, tissue, urine, feces, and the like. As shown, the distal end 756 of the mat 752.

The device 750 also includes a first detachable and sealable bag 770 having a triangular shape with a first opening 774 in fluid communication with the distal end 756 of the fluid flow region 760 and configured to receive the bodily fluids from the patient in a first operational mode of the device. As will be described further below, the first detachable and sealable bag 770 is formed of a polymeric material. Thus, the first detachable and sealable bag 770 may be disposable. The first detachable and sealable bag 770 includes a closure mechanism 776 that can seal the opening 774 and the bodily fluids within the first detachable and sealable bag 770. Suitable closure mechanisms 776 include by way of non-limiting example, a zipper, a slide, an adhesive, or a cinching string. While not shown, as with previous embodiments, the closure mechanism 776 may further be disposed in a protective sleeve to shield it from exposure to bodily fluids. Further, the first detachable and sealable bag 770 has a weak region or tear line 778 (e.g., defined by perforations). Once the first detachable and sealable bag 770 is sealed by the closure mechanism 776, the first detachable and sealable bag 770 may be removed at the tear line 778 and separated from the device 750. The first detachable and sealable bag 770 is thus disposed over a second sealable bag 772.

In the first operational mode, the first detachable and sealable bag 770 collects bodily fluids (e.g., delivery fluids, amniotic fluid, urine, fecal matter, disinfectant solution, tissues, and the like) during the stages of delivery prior to when the placenta is delivered. The first detachable and sealable bag 770 may be detached from the device 750 after stage 2 of delivery. Notably, the device 750 does not interfere with or impede access to the patient during the delivery process and can be disposed under the patient before delivery, yet remain intact afterwards.

The second operational mode of device 750 begins after the baby and optionally after the placenta are delivered (transitioning to the second operational mode when delivery stages 2 and 3 are completed). The device 750 also includes the second sealable bag 772 having a second opening 780 in fluid communication with the distal end 756 of the fluid flow region 760 and configured to receive the bodily fluids from the patient in a second operational mode of the device 750. As will be described further below, the second sealable bag 772 is formed of a polymeric material. Thus, the second sealable bag 772 may be disposable. The second sealable bag 772 has a distinct shape from the first bag 770.

The second sealable bag 772 may optionally be detachable from the mat 752. The second sealable bag 772 may have a distinct shape from the first sealable bag 770, for example having an upper region 784 in a triangular (conical) shape and a lower region 786 in a rectangular (cylindrical) shape. The second sealable bag 772 may have a visual volume indicator 782 having marked gradations to measure a volume of the bodily fluids collected in the second sealable bag 772. The second sealable bag 772 also may have a closure mechanism 788. During the second operational mode of the device 750, where the second sealable bag 772 collects bodily fluids, the bodily fluids tend to be blood and are most indicative of a potential postpartum hemorrhage.

FIGS. 42A-42B show a variation of a design of a second collection bag for a device according to the present disclosure having a triangular (or conical) upper region that transforms to a cylinder lower region having indicia to measure volume of fluids collected. FIG. 42B shows a detailed view of the indicia to measure volume of fluids, including one half of each marking and volumetric amount being a light color (e.g., white text and lines) and one half of each marking and volumetric amount being a dark color (e.g., black text and lines). The second collection bag with marked gradations can be collected and can quantify hemorrhaging blood accurately after the placenta is delivered. In certain aspects, the present disclosure contemplates a new, original and ornamental design for a device for blood loss measurement following childbirth to detect postpartum hemorrhage, as shown in FIGS. 42A-42B, of which the above description forms a part of the specification.

FIGS. 43A-43B show a device for collecting bodily fluids from a patient during and after childbirth prepared in accordance with certain aspects of the present disclosure where a distal region of the mat can be used to distinguish and separate fluids. As shown in FIG. 43A, a hinged wall or other material extending along the distal region can obstruct the blood-collection bag to force non-blood fluid to flow into side compartments on each lateral side of the mat. However, as shown in FIG. 43B, blood can flow over the wall or other material into the tongue and second collection bag, thus serving to separate blood from other fluids.

FIG. 44 shows a device for collecting bodily fluids from a patient during and after childbirth having one or more collection bags permanently connected with the mat prepared in accordance with certain aspects of the present disclosure. Such a device can be produced in multiple parts or integrally fabricated together—securely and permanently attaching the parts together, for example, by adhesive, tape, heat welding, and the like.

FIGS. 45A-45D show different variations of designs for a second collection bag for a device according to the present disclosure having an upper region that transforms to a cylinder lower region to measure volume of fluids collected. FIG. 45A shows a triangular (or conical) upper region that transitions to a cylindrical lower region. FIG. 45B shows another variation of a wider triangular (or conical) upper region that transitions to a cylindrical lower region. FIG. 45C shows another variation of a hemispherical upper region that transitions to a cylindrical lower region. FIG. 45D shows a fluted or tulip upper region that transitions to a cylindrical lower region.

Figure 46A:
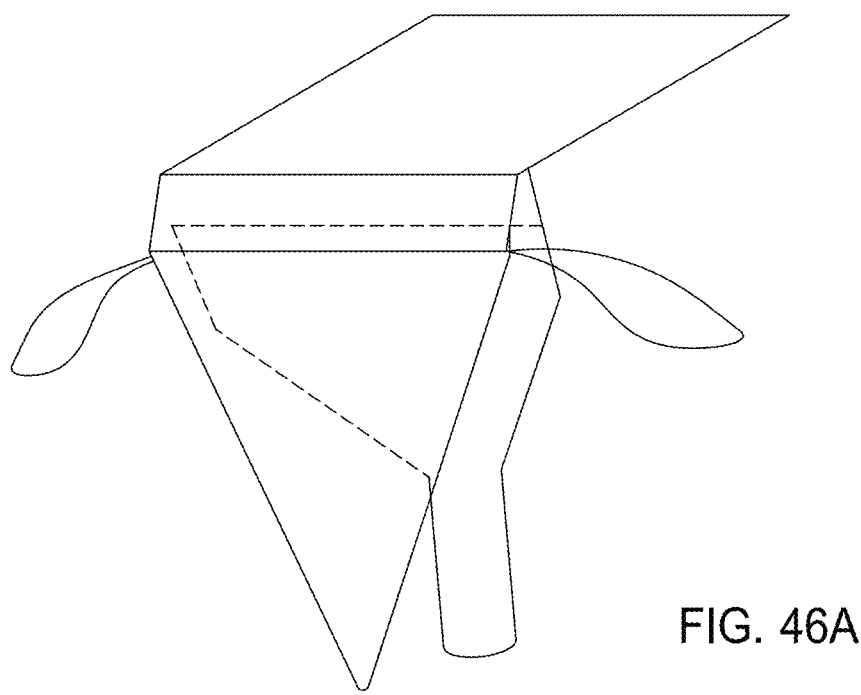
Figure 46B:
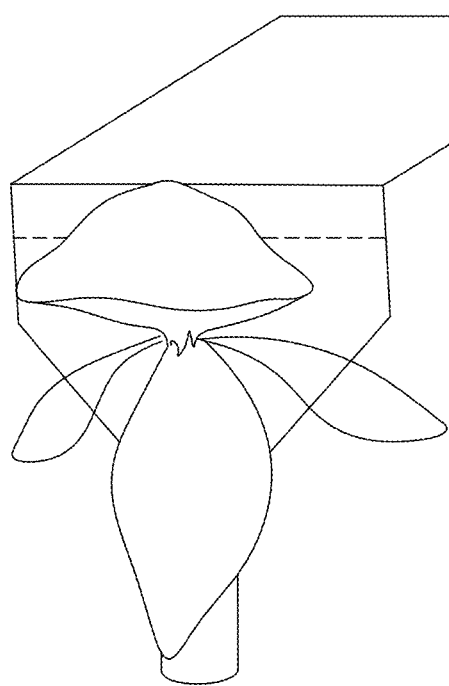
Figure 46C:
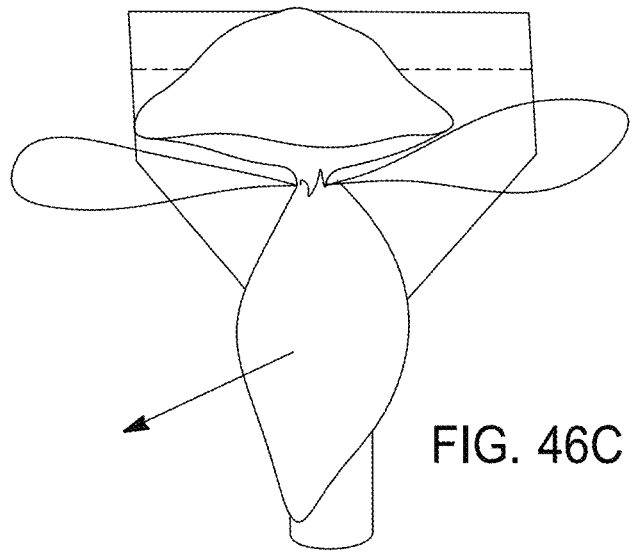
Figure 46D:
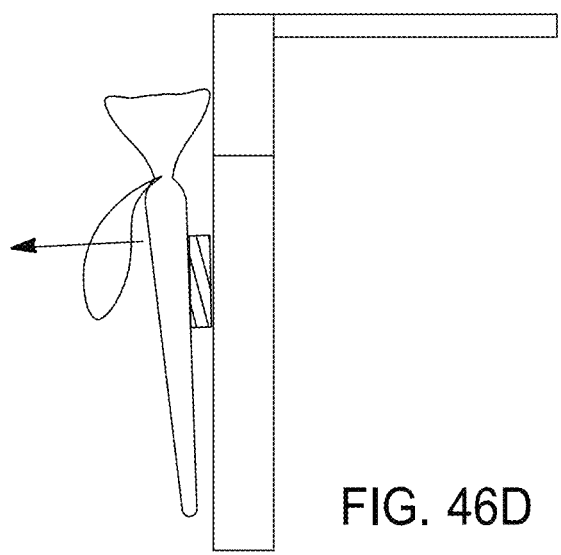
Figure 46E:
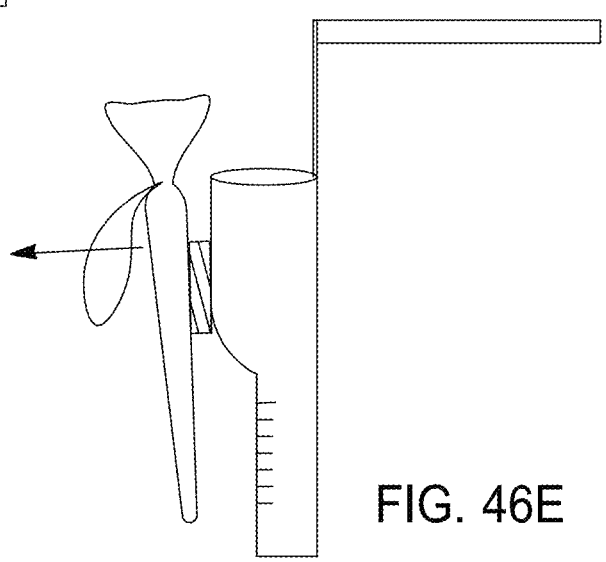

FIGS. 46A-46E show successive steps for use of a device for collecting bodily fluids from a patient during and after childbirth having a concurrent tear away and prop open drapes prepared in accordance with certain aspects of the present disclosure. In a first step shown in FIG. 46A, there are two collection bags, where the first collection bag has a closure mechanism in the form of a drawstring that is capable of cinching the collection bag pouch closed. A first drape/collection bag props open the second drape/collection bag as it is being teared away and removed. The second collection bag props open when the first collection bag is torn away from tape on the second collection bag. A second collection bag is permanently adhered to the mat/drape (for example, as shown in FIG. 44). In FIG. 46B, the drawstring is pulled and cinched in the first collection bag. In FIG. 46C, the first collection bag is pulled away from the device to remove it. As shown in the side views from FIGS. 46D and 46E, initially the first collection bag and second collection bag are adjacent to one another, but as the first collection bag is pulled away from the device, the second collection bag props open.

FIG. 47 shows a design for a second collection bag for a device according to the present disclosure having a dark background, for example, a back wall of the second collection bag is dark or black, while the front wall of the second collection bag is transparent. In this design, the indicia showing volume levels and text can be more visible. By way of example, the indicia including markers of volume levels or text on the front wall may be a light color (e.g., white).

FIG. 48 shows another design for a second collection bag for a device according to the present disclosure, where half of each indicia provided on the second collection bag is in a light color and half is in a dark color. For example, the volume level indicator/gradation lines may be dark colored (e.g., black text or lines), while the other half of each volume level indicator/gradation lines may be light colored (e.g., white text or lines). Such a design enhances visibility for different colored fluids that may be stored in the second collection bag, including in a variety of ambient lighting conditions.

FIGS. 49A-49C show yet other variations of a device for collecting bodily fluids from a patient during and after childbirth prepared in accordance with certain aspects of the present disclosure. The first collection bag and/or the second collection bag have a closure mechanism in the form of a double-side tape that can seal each side of the upper region of the collection bag to one another and thus seal the opening closed. As shown in FIG. 49A, a double-sided tape/adhesive is provided on a back surface of the opening to the collection bag. In FIG. 49B, a double-sided tape/adhesive is provided on a front surface of the opening to the collection bag. In FIG. 49C, a double-sided tape/adhesive is provided on both a front and a back surface of the opening to the collection bag and are capable of adhering to one another to seal the opening of the collection bag.

FIGS. 49A-49C show yet other variations of a device for collecting bodily fluids from a patient during and after childbirth prepared in accordance with certain aspects of the present disclosure. The first collection bag and/or the second collection bag may have a closure mechanism in the form of a double-side tape that can seal each side of the upper region of the collection bag to one another and thus seal the opening closed. As shown in FIG. 49A, a double-sided tape/adhesive is provided on a back surface of the opening to the collection bag. In FIG. 49B, a double-sided tape/adhesive is provided on a front surface of the opening to the collection bag. In FIG. 49C, a double-sided tape/adhesive is provided on both a front and a back surface of the opening to the collection bag and are capable of adhering to one another to seal the opening of the collection bag.

FIGS. 50A-50D show yet another variation of a device for collecting bodily fluids from a patient during and after childbirth prepared in accordance with certain aspects of the present disclosure, where a portion of polymeric material remains on the distal area of the mat device near the tongue after removing the first detachable collection bag and using the remaining portion as a cover and seal for the second collection bag. In FIG. 50A, a first collection bag is removed by tearing along a perforated line, where an extra portion of the polymeric material remains. Thus after the perforation of the first collection bag, there is still a lip of extra plastic material left over on the distal end of the mat. This plastic piece may have an adhesive and is adhered to the second collection bag. Attaching the extra plastic from the first collection bag via an adhesive can prevent or minimize any fluid flowing over the plastic from spilling out of the collection bag, which would have occurred if it was not adhered to the second collection pouch. In FIG. 50B, a closure mechanism of the second collection bag is a double-sided tape. A concern with using a double-sided tape sealing mechanism for the second collection bag is that as the fluid flows down into the second collection bag, the plastic may have fluid droplets which make it difficult to seal. However, in the embodiment shown, the underside portion of polymeric material remaining in the distal region of the mat/upper region of the second collection bag is dry in that it is protected and has minimal or no contact with fluid as it passes into the second collection bag. The underside portion can be lifted up to provide a dry surface as shown in FIG. 50C. Thus, the plastic can be peeled and lifted to reveal dry plastic to which the double-sided tape will adhere and seal the opening of the second collection bag. Backing can be removed from the double-sided tape as shown in FIG. 50D, so that the double-sided tape sticks to the dry underside of the extra portion of the polymeric material and thus forms a superior seal for extra protection. After the second collection bag is sealed, the extra plastic piece remaining from the first collection bag can be attached to the outside of the sealed second collection bag, in an envelope like form, to improve the sealing of the second collection bag.

In various aspects, the devices for collecting bodily fluids from a patient during and after childbirth prepared in accordance with the present disclosure allow laboring women mobility to change positions while using the device, because labor and delivery can be extensive and patient movement may help with pain management. Therefore, the patient is able to move between and maintain the supine, prone, lateral and sims positions, as these are the most common positions for laboring patients. In addition, the device is not invasive and thus does not cause additional discomfort for the patient or increase the risk of infection.

Once the baby is delivered, a first bag can be sealed and torn away, allowing mostly blood product to collect in the second bag. These features enable the devices provided by the present disclosure to distinguish blood from other fluids, so that the fluid being measured is solely blood. A combination of the pre-delivery fluids and blood product will result in an inaccurate blood loss measurement. Moreover, it is extremely difficult to separate the other fluids from blood once they are mixed. In the first operational mode, the pre-delivery fluids are collected. In a second operational mode, fluids expelled as the baby is being born and afterwards are collected. In certain aspects, the transition between the first operational mode and the second operational mode (where the top bag is removed) occurs immediately prior to the delivery of the baby. After the delivery of the baby, approximately 90% of the fluid lost is blood, allowing the second bag to collect predominantly blood products. Furthermore, the blood lost at this point is the most important in diagnosing postpartum hemorrhage and is collected in the second operational mode of the device by the second collection blood.

In addition to the device's ability to distinguish blood from other fluids, it also provides a simple design with lower barriers to implementation in low resource settings, including its low-cost, disposable nature in certain aspects.

During manufacturing, RF welding of the polymeric starting materials can be used to create sealed collection bags, for example, having a trapezoidal shape, to create the perforations, and to join the bags to the base plastic sheet that forms the mat portion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for measuring postpartum blood loss, the device comprising:
    a mat defining a proximal end and a distal end, the mat being configured to be disposed between a support and a patient, and the mat comprising a surface defining a fluid flow region configured to direct flow of bodily fluids from the patient towards the distal end of the mat;
    a first detachable bag having a first opening in fluid communication with the distal end of the fluid flow region and configured to receive the bodily fluids from the patient in a first operational mode of the device; and
    a second sealable bag having a second opening in fluid communication with the distal end of the fluid flow region and configured to receive the bodily fluids from the patient in a second operational mode of the device, wherein the second sealable bag comprises a visual volume indicator to measure the bodily fluids collected in the second sealable bag.

2. The device of claim 1, wherein the first detachable bag is disposed over the second sealable bag.

3. The device of claim 1, wherein the first detachable bag has a first volumetric capacity and the second sealable bag has a second volumetric capacity, wherein the first volumetric capacity and the second volume capacity are equal to one another and the first volumetric capacity and the second volume capacity are each less than or equal to about 2,000 mL.

4. The device of claim 1, wherein the visual volume indicator comprises a minimum volumetric unit of 250 mL.

5. The device of claim 1, wherein the first detachable bag has a first shape and the second sealable bag has a second shape, wherein the first shape and the second shape are the same and selected from one of an isosceles triangle and an isosceles trapezoid.

6. The device of claim 1, wherein the mat defines two peripheral edges that define a region selected from one of a bumper, a raised portion, a roll, or a channel to create the fluid flow region and configured to prevent egress of bodily fluids beyond the two peripheral edges.

7. The device of claim 1 further comprising a fastener to couple the mat to the support.

8. The device of claim 7, wherein the fastener is selected from one or more of:
    a belt or a strap that extends around a circumference of the support;
    an adhesive that adheres to a surface of the support;
    buttons to couple to a surface of the support;
    magnets to couple to a surface of the support;
    hook and eye material to couple to a surface of the support; or
    a snap to couple to a surface of the support.

9. The device of claim 1, wherein the distal end of the mat extends over a terminal edge of the support.

10. The device of claim 1 further comprising fasteners to couple the mat to the patient, wherein the fasteners comprise at least two straps.

11. The device of claim 1, wherein the mat defines two peripheral edges that each extend over lateral edges of the support.

12. The device of claim 1, wherein the first detachable bag and the second sealable bag comprise a closure mechanism selected from one or more of a zipper, a slide, an adhesive, or a cinching string.

13. The device of claim 12, wherein the closure mechanism is disposed in a protective sleeve.

14. The device of claim 1, wherein the first detachable bag, the second sealable bag, and the mat are independently formed of a polymer selected from the group consisting of: polypropylene, polyethylene, polyetheretherketone (PEEK), polyvinylchloride (PVC), polyurethane (PU), metallocene catalyzed thermoplastic polymers, siloxane, elastomers, shape memory elastomers, and combinations thereof.

15. The device of claim 1, wherein the first detachable bag and the second sealable bag are disposable.

16. The device of claim 1, wherein the mat is reusable and the first detachable bag and the second sealable bag comprises at least one connector to reversibly couple with the mat.

17. The device of claim 1, wherein the second sealable bag further comprises a filter configured to filter blood from other bodily fluids.

18. The device of claim 1, wherein the mat has a shape selected from a rectangle, a trapezoid, or a hemisphere.

19. The device of claim 1, wherein the first detachable bag and the second sealable bag comprise a handle.

20. The device of claim 1, wherein the first detachable bag and/or the second sealable bag further each comprises an internally disposed reinforcement to retain a shape and maintain patency of the first opening and/or the second opening.

21. The device of claim 1, wherein the distal end of the mat defines a shape selected from a trapezoid, a triangle, and a rectangle.

22. The device of claim 1, wherein at least one of the first detachable bag and the second sealable bag comprises a port.

23. The device of claim 1, wherein the proximal end of the mat comprises a flap or folded region.

24. The device of claim 1, wherein the first detachable bag has a first shape and the second sealable bag has a second shape, wherein the first shape is selected from one of an isosceles triangle and an isosceles trapezoid and the second shape comprises a portion in the form of a graduated cylinder.

25. The device of claim 24, wherein the second shape further includes an entry region defining a triangular, quadrilateral, or pentagon shape connected to the graduated cylinder.

26. The device of claim 1, wherein the second sealable bag has a back wall that is dark and a front wall that is transparent and the visual volume indicator is on the front wall.

27. The device of claim 1, wherein the visual volume indicator includes a portion indicated in a dark color and a portion indicated in a light color.

28. The device of claim 1, wherein the first detachable bag is also sealable.

\* \* \* \* \*